(12) United States Patent
Otani et al.

(10) Patent No.: US 9,303,248 B2
(45) Date of Patent: Apr. 5, 2016

(54) POLYPEPTIDES HAVING LIPASE ACTIVITY AND POLYNUCLEOTIDES ENCODING SAME

(71) Applicants: Novozymes, Inc., Davis, CA (US); Novozymes A/S, Bagsvaerd (DK)

(72) Inventors: Suzanne Otani, Elk Grove, CA (US); Debbie Yaver, Davis, CA (US); Haiyan Ge, Davis, CA (US); Janine Lin, Davis, CA (US); Christopher Amolo, West Sacramento, CA (US); Kim Borch, Birkerød (DK); Shamkant Anant Patkar, Lyngby (DK); Michael Lamsa, Woodland, CA (US); Barbara Cherry, Winters, CA (US)

(73) Assignees: NOVOZYMES A/S, Bagsvaerd (DK); NOVOZYMES, INC., Davis, CA (US)

(*) Notice: Subject to any disclaimer, the term of this patent is extended or adjusted under 35 U.S.C. 154(b) by 0 days.

(21) Appl. No.: 13/747,184

(22) Filed: Jan. 22, 2013

(65) Prior Publication Data

US 2013/0123163 A1    May 16, 2013

Related U.S. Application Data

(62) Division of application No. 12/696,676, filed on Jan. 29, 2010, now Pat. No. 8,377,675, which is a division of application No. 11/241,677, filed on Sep. 30, 2005, now Pat. No. 7,666,630.

(60) Provisional application No. 60/614,508, filed on Sep. 30, 2004, provisional application No. 60/621,304, filed on Oct. 21, 2004, provisional application No. 60/621,222, filed on Oct. 21, 2004.

(51) Int. Cl.
    *C12N 9/20*    (2006.01)

(52) U.S. Cl.
    CPC .................................... *C12N 9/20* (2013.01)

(58) Field of Classification Search
    CPC .......................................... C12N 9/20
    See application file for complete search history.

(56) References Cited

U.S. PATENT DOCUMENTS

| 6,103,505 | A  | 8/2000 | Clausen et al. |
| 6,852,346 | B2 | 2/2005 | Soe |

FOREIGN PATENT DOCUMENTS

| WO | 9826057 | A1 | 6/1998 |
| WO | 9953001 | A1 | 10/1999 |
| WO | 0183773 | | 11/2001 |
| WO | 03012071 | A2 | 2/2003 |
| WO | 03060112 | A1 | 7/2003 |

OTHER PUBLICATIONS

Surfactants: the ubiquitous amphiphiles, http://www.rsc.org/chemistryworld/issues/2003/july/amphiphiles.asp, retrieved Mar. 13, 2014.*
Saponins. http://www.ecologicalsurfactants.com/saponin/, retrieved Mar. 13, 2014.*
Fickers et al., 2003, UNIPROT Access No. Q872L5.
Bigey et al, 2003, UNIPROT Access No. Q875HO.
Thines et al, 2000, Plant Cell 12(9), 1703-1718.
WO 1998-026057 A1—EBI Access No. AAW51765.
WO 1999-053001 A1—EBI Access No. AAY32085.
WO 2003-012071 A2—EBI Access No. AA024083.
WO 2003-060112 A1—EBI Access No. ABB80176.
Bigey et al. 2003, Yeast 20 (3), 233-248.
El-Shahed et al., 1988, Egypt. J. Microbiol. 23: 537-547.
Mayordomo et al., 2000, J. Agric. Chem. 48: 105-109.
S.M. Mohawed et al., 1988, Egypt. J. Microbiol. 23: 357-372.
Galagan et al., 2003 UNIPROT Access No. Q7SEP2, XP-002369012.
V.W. Ogundero, Hydrolysis of vegetable oils and triglycerides by thermotolerant and zoopathogenic species of *Aspergillus* from Nigerian palm produce, Mycopathologia, v. 77, 1982, pp. 43-46.
Galagan, James E. et al., The genome sequence of the filamentous fungus *Neurospora crassa*, Nature, vol. 422, Apr. 24, 2003, pp. 859-868.
Birren et al., 2003, GenBank: XM_364994.
Birren et al., 2003, GenBank: XM_370519.
Birren et al., 2003, GenBank: XM_362110.

* cited by examiner

*Primary Examiner* — Rebecca Prouty
(74) *Attorney, Agent, or Firm* — Kristin McNamara

(57) ABSTRACT

The present invention relates to isolated polypeptides having lipase activity and isolated polynucleotides encoding the polypeptides. The invention also relates to nucleic acid constructs, vectors, and host cells comprising the polynucleotides as well as methods for producing and using the polypeptides.

19 Claims, 24 Drawing Sheets

```
              M  L  H  K  Y  S  L  F  C  L  T  I  F  S  C  L  F  V  V  S
   1   ATGCTTCACAAGTATAGCCTGTTCTGTCTCACTATTTTCTCCTGCCTCTTCGTTGTGAGC
          V  D  G  A  I  L  G  R  D  D  E  G  R  Q  Q  I  P  D  E  L
  61   GTGGATGGGGCAATACTCGGTAGGGATGATGAAGGCCGACAGCAGATACCTGATGAACTC
          F  E  S  L  E  E  L  S  R  I  V  D  V  S  Y  C  V  G  T  T
 121   TTTGAATCACTCGAAGAGCTCTCACGTATCGTTGATGTTTCGTACTGTGTTGGGACCACT
          E  I  R  K  P  F  K  C  L  S  H  C  S  E  F  Q  G  F  E  L
 181   GAAATTCGGAAGCCATTCAAGTGTCTCAGTCATTGTAGTGAATTCCAGGGCTTCGAACTG
          V  T
 241   GTCACCGTATGTTGAAAGCCTCTCACTTATATGTTGTCTTTCTGTCCAAGCTTGATGGCT
                   T  W  N  T  G  P  F  L  S  D  S  C  G  Y  V
 301   TAGATCGTCTCCAGACATGGAATACCGGTCCTTTCCTTTCCGATTCCTGTGGCTATGTAA
          T  L  S  H  E  P  S  P  K  R  I  I  V  A  F  R  G  T  Y  S
 361   CCCTCTCCCACGAACCATCTCCGAAGCGGATCATCGTTGCCTTTCGCGGCACTTACTCGA
          I  A  N  T  I  I  D  L  S  A  Y  P  Q  A  Y  V  P  Y  H  P
 421   TCGCCAACACGATCATCGATCTATCCGCCTATCCTCAGGCCTATGTACCGTATCATCCG
          E  D  G  K  V  S  D  H  L  Q  C  L  N  C  T  V  H  A  G  F
 481   AGGATGGAAAAGTGTCCGACCATTTACAATGTCTGAACTGCACAGTTCATGCGGGGTTTT
          L  A  S  W  S  N  A  R  A  I  V  L  E  H  V  A  V  A  R  A
 541   TGGCCTCGTGGAGCAATGCTCGCGCCATAGTACTCGAGCACGTAGCTGTGGCAAGGGCCC
          R  Y  P  D  Y  S  L  V  L  T  G  H  S  L  G  G  A  V  A  A
 601   GGTACCCGGATTACAGCTTGGTTTTGACCGGCCACTCGCTTGGCGGCGCCGTCGCCGCTC
          L  A  G  V  E  M  Q  L  R  G  W  E  P  Q  V  T  T  F  G  E
 661   TTGCCGGGGTCGAAATGCAACTGCGCGGGTGGGAGCCACAAGTGACCACTTTCGGAGAGC
          P  R  I  G  N  K  A  F  V  E  F  L  D  R  I  F  D  L  D  G
 721   CAAGAATCGGAAACAAGGCTTTTGTGGAATTTCTTGATCGGATCTTTGATCTAGATGGCT
          L  G  A  D  A  Q  D  T  R  F  R  R  V  T  H  I  N  D  P  V
 781   TGGGAGCTGATGCCCAGGACACCAGATTTCGAAGAGTCACACATATCAACGATCCGGTCC
          P  L  L  P  L  S  E  W  G  Y  E  M  H  A  G  E  I  F  I  A
 841   CCCTACTCCCATTGTCAGAATGGGGTTATGAGATGCATGCGGGAGAGATCTTTATCGCTA
          K  E  E  L  S  P  L  H  D  I  R  L  C  Q  G  D  N  D  A
 901   AGGAGGAGCTCTCGCCTCTACCCCATGATATCAGACTGTGCCAGGGCGACAACGATGCGC
          R  C  I  A  G  T  D  G  A  V  T  R  M  L  N  E  L  D  D  T
 961   GATGCATTGCAGGAACGGATGGAGCTGTAACGCGCATGCTGAACGAGTTGGATGATACCG
          V  L  P  K  Q  P  L  A  K  R  V  Q  S  P  H  Q  A  V  L  A
1021   TTTTGCCCAAGCAGCCTCTAGCGAAACGAGTCCAGTCACCCCATCAGGCCGTTTTGGCAG
          D  V  D  P  H  S  S  A  D  V  D  E  Q  V  Q  T  P  F  S  L
1081   ACGTGGATCCTCATAGTAGTGCAGATGTCGACGAGCAAGTACAGACGCCATTCAGCCTGC
          P  W  H  L  I  P  S  R  Y  R  L  W  E  L  F  F  A  H  R  D
1141   CTTGGCATCTTATTCCCTCCAGATACCGACTGTGGGAGCTGTTCTTCGCTCATCGTGATT
          Y  F  W  R  L  G  L  C  V  P  G  G  D  P  T  G  K  I  I  *
1201   ATTTCTGGCGGCTTGGGCTTTGTGTACCAGGCGGTGATCCGACTGGCAAGATAATCTGA
```

Fig. 2

```
        M   F   H   P   D   I   S   A   G   L   L   A   N   L   T   L   F   S   E   Y
  1     ATGTTTCACCCAGATATTTCGGCTGGGCTTCTAGCCAATCTAACACTATTTTCTGAATAT
        A   A   A   S   T   C   A   A   N   F   N   S   H   T   L   S   K   V   V   C
 61     GCCGCTGCCTCGACGTGTGCAGCAAACTTCAACTCACATACATTATCGAAGGTAGTGTGT
        D   P   G   V   C   P   T   L   E   Q   T   D   T   N   V   M   V   G   F   M
121     GATCCAGGTGTATGCCCAACCCTGGAGCAGACAGACACAAATGTCATGGTTGGGTTCATG
        G                                                           I   H   H   P
181     GGGTATGATTCCATCAACAGGGCATGAACTGAAAAGCTAACGCCAAGTATACATCATCCG
        G   N   V   T   G   F   V   A   I   D   N   T   N   Q   L   I   V   L   S   F
241     GGTAACGTCACTGGCTTCGTGGCAATTGACAACACAAATCAATTGATCGTTCTGTCATTC
        R   G   S   R   T   L   G   N   Y   I   T   D   S   K   Y   Q   Q   V   P   A
301     CGCGGTAGCCGGACCCTAGGCAACTATATCACTGATTCCAAATACCAGCAGGTGCCTGCT
        I   C   P   G   C   Q   V   H   K   G   Y   Y   W   A   W   G   N   F   S   A
361     ATTTGCCCAGGTTGCCAAGTGCATAAAGGCTATTACTGGGCCTGGGGAAACTTTTCAGCA
        F   I   M   Q   P   I   N   Q   L   A   A   I   Y   P   S   Y   Q   I   V   F
421     TTTATAATGCAACCTATAAACCAGCTTGCTGCTATATATCCAAGCTATCAGATTGTCTTC
        T   G   H   S   F   G   G   A   L   A   T   L   G   A   A   L   E   G   G   N
481     ACTGGCCACAGTTTTGGAGGTGCACTAGCTACGCTTGGGGCAGCACTTGAGGGAGGAAAT
        P   S   R   P   I   D   L
541     CCTAGCAGACCTATTGATCTGGTAAGTACCTCAGTCACCGCAAATGTTTCCCTAGAGAAT
                    I   Q   Y   T   F   G   C   P   Q   L   G   N   H   D   F   A
601     GCATTAATCAGATACAGTACACTTTTGGATGTCCCCAACTGGGCAATCATGATTTTGCTG
            E   F   V   T   A   V   T   A   G   S   G   Y   R   V   T   H   S   D   D   P
661     AGTTTGTCACTGCTGTAACGGCAGGCTCTGGGTACAGAGTCACACATTCGGATGATCCAG
        V   P   R   V   F   S   T   Q   P   W   I   N   K   T   W   Q   Y   S   T   T
721     TTCCAAGGGTCTTTTCTACTCAGCCTTGGATCAACAAGACTTGGCAGTATAGCACAACTT
        S   P   E   F   W   I   T   T   G   N   V   P   V   T   A   S   D   I   Q
781     CTCCTGAGTTTTGGATTACCACAGGAAATGGCGTGCCAGTCACAGCCAGTGATATACAAG
        V   I   E   G   I   D   N   K   S   G   N   L   G   T   T   G   S   D   T   S
841     TCATCGAGGGCATTGACAACAAGAGTGGGAACCTTGGCACCACTGGTTCTGATACTTCAG
        A   H   I   W   Y   I   G   N   M   S   G   C   S   T   N   *
901     CTCATATTTGGTATATTGGCAACATGAGCGGGTGCTCAACTAACTGA
```

Fig. 8

```
       M  K  V     S  F  V  S     S  L  L     A  L  P     L  L  A  A     A  A  P     K  P  E
  1  ATGAAGGTCT CGTTCGTGTC ATCGCTCCTC GCGCTCCCGC TCCTTGCGGC CGCGGCCCCC AAGCCCGAGG
       A  A  E  L     S  S  R     D  V  T     V  T  Q  Q     E  L  N     G  F  M     Y  M  R  Q
 71  CCGCTGAGCT GTCGAGCCGC GACGTGACCG TGACGCAGCA GGAGCTCAAC GGCTTCATGT ACATGCGGCA
       L  A  S     A  A  Y     C  N  S  K     D  S  L     V  G  Q     K  V  T     C  S  N  N
141  GCTCGCCTCG GCCGCCTACT GCAACTCCAA GGACAGCCTG GTCGGCCAAA AGGTCACATG CAGCAACAAC
       A  C  P     D  I  G  A     A  N  V     V  N  F     A  H  L  E
211  GCCTGCCCGG ACATTGGCGC CGCTAACGTG GTCAACTTTG CCCATCTCGA GTATGTTTTT TTCCCTCTTT
                                                        S  N     H  L  T     D  T  P     H  D  G  A
281  TTTCTTGTGA AACTCTTGTT GTATAAAAAA AAAGGTCAAA TCATCTAACA GATACCCCCC ACGATGGGGC
       N  S  T     D  I  G     I  K  A  D     G  A  V     F  I  D     H  T  R  G     G  I  V
351  CAACAGCACC GACATCGGCA TCAAGGCCGA CGGCGCTGTC TTCATCGACC ACACCAGGGG CGGCATCGTC
       M  S  F     M  G  S  K     S  W  Q     S  F  M     T  E
421  ATGTCCTTCA TGGGCTCCAA GTCGTGGCAG TCCTTCATGA CCGAGTAAGC AAAACACCCC ACTTACTCTA
                                                                                   L  D  F     T  G  S
491  GATTTTTTTT TATCTTGTCA TCCACATGAC TCACATTTCA CCTCCAAACA GCCTCGACTT CACCGGCAGC
       D  S  S     E  I  C  S     G  C  T     V  H  Y     G  I  K  L     T  Y  D     I  I  E
561  GACTCCTCCG AGATCTGCAG CGGCTGCACG GTCCACTACG GCATCAAGCT CACCTACGAC ATCATCGAGG
       G  A  L  I     N  A  L     N  S  A     R  Q  W     P  S  Y     Q  V  V     A  T  G  H
631  GCGCGCTGAT CAACGCCCTC AACTCGGCCC GCGCCCAGTG GCCGTCGTAC CAGGTCGTCG CGACGGGCCA
       S  I  G     A  G  V     A  T  V  A     A  R     L  R  N     R  L  N  V     D  I  Q
701  CTCCATCGGA GCCGGCGTCG CCACCGTCGC CGCCGCCCGC CTGCGCAACC GCCTCAACGT CGACATCCAG
       L  Y  T     F  G  S  P     R  V  G     N  D  A     F  A  T  F     V  T  N     Q  N  R
771  CTCTACACCT TTGGCAGCCC CCGCGTCGGC AACGACGCCT TTGCCACCTT TGTCACCAAC CAGAACCGCG
       G  R  N  Y     R  I  T     H  Y  D     D  V  V  A     L  P     P  S  W     A  G  F  A
841  GCCGCAACTA CCGCATCACC CACTACGACG ACGTCGTCGC CGCCTTGCCC CCGTCCTGGG CCGGCTTCGC
       H  V  S     P  E  Y     W  L  R  R     K  D  A     S  D  F     N  Y  P  L     S  E  V
```

Fig. 10A

```
 911  CCACGTCAGC CCCGAGTACT GGCTGCGCAG GAAGGACGCC AGCGACTTCA ACTACCCGCT CAGCGAGGTC
       V  V  C   E  G  I  N   P  K  G   C  R  N    S  M  G  T    T  L  S    G  K  A
 981  GTCGTCTGCG AGGGCATCAA CCCCAAGGGT TGCAGGAACA GCATGGGCAC CACCCTCAGC GGCAAGGCCC
       H  G  E  Y   F  G  A   I  S  A   C  Y  *
1051  ACGGAGAGTA CTTTGGCGCC ATTAGCGCTT GCTACTGA
```

Fig. 10B

```
        M   R   F   P   S   V   L   T   L   L   A   T   A   L   T   C   S   A   S   V
   1    ATGAGGTTCCCCAGCGTGCTCACCCTTTTGGCCACAGCCCTCACCTGCTCGGCATCGGTT
        L   P   A   G   L   T   Y   T   K   T   V   E   G   R   D   V   T   V   S   E
  61    CTCCCTGCCGGCCTGACCTACACCAAGACTGTCGAGGGCCGCGATGTGACCGTCAGCGAG
        T   D   L   D   N   F   R   F   Y   A   Q   Y   S   A   A   T   Y   C   N   D
 121    ACAGACCTAGACAACTTCCGTTTCTATGCGCAGTACAGCGCGGCGACCTACTGCAACGAT
        A   A   A   S   G   A   A   V   A   C   S   N   D   G   C   P   A   V   V   A
 181    GCCGCCGCCTCAGGGGCCGCCGTCGCCTGCAGCAACGACGGATGTCCCGCCGTCGTGGCC
        N   G   A   K   I   I   R   S   L   N   Q   D   T   S   T   N   T   A   G   Y
 241    AACGGAGCCAAGATCATCCGTTCGCTGAACCAAGACACGTCCACCAACACTGCCGGCTAC
        L   A   L   D   P   K   R   K   N   I   V   L   A   L   R   G   S   T   S   L
 301    CTTGCACTCGACCCCAAGCGGAAGAACATCGTGCTCGCCCTCCGTGGCTCCACGAGCCTC
        R   N   W   I   T   N   L   T   F   L   W   T   R   C   D   F   V   Q   D   C
 361    CGGAACTGGATCACCAACCTGACTTTCCTGTGGACCCGCTGCGACTTTGTCCAGGACTGC
        K   L   H   T   G   F   A   T   A   W   S   Q   V   Q   A   D   V   L   A   A
 421    AAGCTGCACACGGGCTTTGCCACAGCCTGGTCCCAGGTGCAGGCCGATGTTCTGGCCGCC
        I   A   D   A   K   A   Q   N   P   D   Y   T   V   V   V   T   G   H   S   L
 481    ATCGCCGACGCCAAGGCCCAGAACCCCGACTACACCGTCGTCGTGACGGGCCACTCCCTC
        G   G   A   V   A   T   V   A   G   V   Y   L   R   Q   L   G   Y   P   V   E
 541    GGCGGCGCCGTCGCCACCGTCGCGGGAGTCTACCTCCGCCAGCTGGGCTACCCCGTCGAG
        V   Y   T   Y   G   S   P   R   I   G   N   Q   E   F   V   Q   W   V   S   T
 601    GTTTACACGTACGGCAGCCCGCGCATCGGCAATCAGGAGTTTGTGCAGTGGGTTTCCACG
        Q   A   G   N   V   E   Y   R   V   T   H   I   D   D   P   V   P   R   L   P
 661    CAGGCCGGCAACGTCGAGTACCGCGTCACGCACATCGACGACCCCGTCCCCCGCCTGCCG
        P   I   F   L   G   Y   R   H   V   T   P   E   Y   W   L   N   S   G   T   S
 721    CCCATCTTCCTCGGCTACAGGCACGTCACCCCCGAGTACTGGCTCAACTCTGGCACCTCC
        N   T   V   N   Y   T   V   A   D   I   K   V   C   E   G   F   A   N   I   N
 781    AACACGGTCAACTACACCGTCGCCGACATCAAGGTCTGCGAGGGCTTCGCCAACATCAAC
        C   N   G   G   S   L   G   L   D   T   N   A   H   L   Y   Y   L   T   D   M
 841    TGCAACGGCGGCAGCCTCGGCCTCGACACAAACGCCCACCTCTACTACCTCACCGACATG
        I   A   C   G   S   N   K   F   V   R   R   D   D   A   N   A   I   S   D
 901    ATCGCCTGCGGCTCCAACAAGTTCGTCTTCCGCCGCGACGACGCCAACGCCATCAGTGAC
        A   E   L   E   Q   R   L   T   M   Y   A   Q   M   D   R   E   F   V   A   A
 961    GCCGAGCTCGAGCAGAGGCTGACCATGTACGCTCAAATGGATCGCGAGTTTGTTGCTGCG
        L   E   A   N   K   T   V   *
1021    CTTGAAGCCAACAAGACCGTGGCTTAA
```

Fig. 13

```
  M   L   W   R   R   A   G   G   L   C   L   L   L   C   W   A   W   A   T   P   A
ATGTTGTGGCGTCGGGCGGGTGGCCTCTGTCTGTTGCTGTGTTGGGCCTGGGCAACACCGGCA
  Q   A   A   A   F   S   H   D   I   T   Q   L   S   Y   T   D   V   D   S   P   L
CAAGCTGCAGCATTTAGTCATGACATCACCCAGCTGAGCTACACGGATGTCGACTCGCCTCTC
  Q   K   H   L   Q   S   Q   Q   Q   Q   K   Q   E   H   K   Q   K   P   I   T   T
CAAAAACACCTACAATCACAACAACAACAAAAACAAGAACACAAACAAAAACCTATCACCACC
  T   T   I   S   S   I   L   F   T   S   L   E   R   L   A   R   L   V   D   I   A
ACAACCATTTCTTCAATACTCTTCACGTCTCTAGAGCGCCTGGCCCGCCTCGTAGACATAGCC
  Y   C   V   G   S   L   P   G   I   S   R   P   F   T   C   A   S   R   C   A   D
TACTGCGTGGGAAGTCTGCCCGGCATCTCGCGGCCCTTCACCTGCGCCTCGCGCTGCGCCGAT
  F   P   H   V   S   L   V   N   T   W   D   T   G   P   L   L   T   D   S   C   G
TTCCCCCACGTTTCACTCGTCAACACCTGGGACACGGGCCCACTCCTGACAGACAGCTGCGGC
  Y   V   A   I   D   H   A   D   E   A   I   V   V   A   F   R   G   T   Y   S   I
TACGTCGCCATCGACCACGCCGATGAAGCCATAGTGGTCGCCTTTCGGGGCACCTACAGCATC
  A   N   T   V   I   D   L   S   T   V   P   Q   E   Y   V   P   Y   P   E   P   D
GCCAACACCGTGATTGACCTCAGCACGGTGCCGCAGGAGTACGTGCCCTATCCGGAGCCCGAC
  D   D   G   D   R   E   R   C   D   N   C   T   V   H   L   G   F   L   A   S   W
GACGATGGCGACAGGGAGCGCTGCGACAACTGCACCGTGCACCTAGGATTCCTAGCCAGCTGG
  K   V   A   R   N   L   V   L   P   A   I   E   E   A   R   Q   K   H   P   G   F
AAGGTCGCCAGGAATCTGGTCCTGCCCGCCATCGAGGAGGCGAGGCAGAAGCACCCCGGCTTC
  S   I   N   L   V   G   H   S   L   G   G   A   V   A   A   L   A   A   L   E   L
AGCATCAACCTCGTCGGCCACAGCCTCGGCGGTGCCGTCGCTGCGCTGGCGGCGCTCGAGCTG
  K   L   I   S   G   Y   D   V   V   V   T   T   F   G   E   P   R   V   G   N   S
AAGCTCATCAGCGGCTACGATGTCGTAGTCACGACTTTTGGTGAGCCGAGGGTTGGCAACAGC
  G   L   A   K   F   I   D   R   V   F   G   L   D   Q   E   A   K   E   D   M   A
GGGCTGGCAAAGTTCATTGATCGCGTGTTCGGCTTAGACCAGGAAGCAAAAGAGGACATGGCG
  Y   R   R   V   T   H   A   E   D   P   V   P   L   L   P   L   E   E   W   G   Y
TACCGCAGGGTCACGCACGCCGAGGATCCGGTACCGTTGCTGCCGCTCGAGGAGTGGGGATAC
  R   S   H   A   G   E   I   H   I   E   K   P   A   L   P   P   A   P   T   D   I
AGGTCACACGCCGGCGAGATTCACATTGAAGCCGGCGCTACCACCAGCACCGACTGACATA
  K   L   C   K   G   E   R   D   P   D   C   S   N   G   N   S   D   A   A   L   T
AAGTTGTGCAAAGGCGAAAGGGATCCCGATTGCAGCAACGGGAACTCTGACGCGGCGCTGACT
  T   L   L   G   E   E   H   Y   L   K   K   Q   H   L   K   W   Q   L   F
ACCTTGCTGCTTGGAGAGGAACATTATCTAAAGAAACAGCATCTGAAGCTGTGGCAGCTGTTC
  F   A   H   R   D   Y   F   W   R   L   G   L   C   V   P   G   G   D   P   A   D
TTTGCCCATCGAGACTACTTTTGGAGGCTTGGGCTTTGCGTTCCCGGTGGTGATCCGGCTGAT
  W   G   R   D   K   Y   D   V   A   P   G   Q   D   E   L   *
TGGGGTAGAGACAAGTATGATGTGGCTCCTGGCCAGGATGAGCTCTAA
```

Fig. 15

```
       M   I   R     L   G   Y   S     A   I   F     V   A   L     A   G   L   A     V   A   A     P   A   P
  1    ATGATCCGTT  TGGGGTATTC  TGCCATCTTC  GTAGCCCTTG  CTGGGTTAGC  CGTTGCCGCT  CCAGCGCCGC
       L   N   R   R                                                                 D   V   S   T
 71    TGAATCGTCG  TGGTATGTCA  CCTTGCATGG  GGATATGGTA  CAGGACTAAC  GTTGTGTAGA  CGTTTCGACG
       E   A   L     N   Q   L   T     L   F   A     E   Y   S     A   A   S   Y     C   T   P     N   I   G
141    GAGGCCCTAA  ATCAACTGAC  CCTGTTCGCG  GAGTATTCTG  CGGCATCGTA  CTGCACACCC  AATATTGGGT
       S   V   G   D     K   L   T     C   A   S     G   N   C   P     T   V   E     A   A   D     T   T   T   L
211    CAGTCGGGGA  CAAGCTGACT  TGCGCATCTG  GAAACTGCCC  GACAGTTGAG  GCAGCAGACA  CGACAACGCT
       A   E   F   Y   Q
281    GGCTGAATTC  TATCAGTGCG  TTAAGCCCTG  CATTCGGGGT  TCCAAACAGA  TCCAACTAGT  CTGACGAGTC
           E   N     E   Y   G     D   V   A     G   F   L   A     A   D   T     T   N   E     L   L   V   L
351    ACAGGAGAA  CGAATACGGG  GATGTAGCAG  GCTTCCTTGC  CGCAGATACA  ACCAACGAGT  TACTCGTCTT
           S   F   R     G   S   R     T   I   D   T     W   I   A     N   L   D     F   G   L   E     S   V   E
421    GTCCTTCCGT  GGGAGCCGGA  CGATTGACAC  GTGGATTGCA  AACCTCGACT  TTGGCCTGGA  GTCGGTCGAG
       E   I   C     S   G   C   K     A   H   G     G   F   W     K   A   W   Q     V   V   A     D   S   L
491    GAGATCTGTA  GCGGATGCAA  AGCCCACGGC  GGGTTCTGGA  AGGCATGGCA  GGTTGTTGCA  GACTCGTTGA
       T   S   A   I     E   S   A     T   A   T     Y   P   G   Y     A   I   V     F   T   G     H   S   F   G
561    CCTCAGCAAT  TGAGTCTGCT  ACTGCCACAT  ATCCCGGCTA  CGCCATTGTC  TTCACAGGCC  ACAGCTTTGG
       G   A   L     A   T   L     G   A   A   Q     L   R   K     A   G   Y     A   I   E   L
631    AGGAGCATTG  GCTACTCTAG  GCGCAGCGCA  GCTGCGAAAA  GCAGGTTATG  CCATCGAACT  TGTAAGAATC
                                                                       Y   P   Y     G   S   P     R   V   G   N
701    CAGTGTCCAG  CTGGTGGCTA  GCTGTCTGCT  GACGAGCGTA  GTACCCCTAT  GGTAGCCCGC  GTGTTGGCAA
       E   A   L     A   Q   Y     I   T   D   Q     G   A   N     Y   R   V     T   H   T   N     D   I   V
771    CGAAGCTTTG  GCGCAATACA  TCACAGACCA  GGGGGCAAAC  TATCGAGTGA  CGCACACTAA  CGATATCGTT
       P   R   L     P   P   M   L     L   G   F     S   H   L     S   P   E   Y     W   I   T     S   D   N
841    CCCAGACTTC  CTCCCATGTT  GTTGGGCTTC  AGCCACTTGA  GCCCTGAGTA  TTGGATTACC  AGCGACAATG
       E   V   T   P     T   T   T     D   I   Q     V   I   E   G     V   G   S     R   D   G     N   A   G   E
911    AGGTTACCCC  GACGACGACA  GATATCCAGG  TGATTGAAGG  CGTTGGGTCG  AGGGACGGAA  ATGCGGGTGA
       A   A   Q     S   V   E     A   H   S   W     Y   L   I     D   I   T     A   C   Q   *
981    GGCTGCCCAG  TCAGTGGAGG  CACACAGTTG  GTATCTGATA  GATATCACTG  CCTGCCAGTA  A
```

Fig. 17

```
            M  Y  F     L  L  S  V     I  F  H     F  P  V     F  C  A  G     F  P  P     A  V  S
   1   ATGTATTTCC TTCTCTCCGT CATCTTCCAC TTTCCTGTCT TCTGTGCCGG CTTTCCACCT GCCGTATCCA
       R                                                                  E  I  S     T  T  L
  71   GAGGTACGTG ATTCAATGTG CTCAGTAATC CGGCTTGAAC CAACCGCAAT AGAAATATCC ACAACTCTCC
       L  T  K  L     T  L  M     S  Q  Y     S  A  A  S     G  C  S     E  N  N     N  S  S  V
 141   TCACCAAACT CACCCTCATG TCTCAATACT CTGCTGCTTC AGGTTGCAGC GAAAACAATA ACTCTTCTGT
          G  S  S     V  Y  C     G  A  E  M     C  P  L     I  D  S     A  N  T  E     L  L  Y
 211   AGGGAGTTCT GTTTATTGCG GGGCTGAAAT GTGTCCGCTT ATCGACAGTG CCAATACAGA ACTCCTTTAT
        A  F  S     E
 281   GCATTCTCAG AGTATTCCCC TTTCGATATC TCATTGGATT ACCATACTCA ATAGACGCTA ACTCTTTACT
                       I  Y     P  G  D     T  A  G     Y  I  A  A     D  H  T     N  A  L
 351   TTCTCATTAC ACAGGATTTA CCCCGGCGAT ACGGCTGGCT ACATTGCCGC CGACCACACA AACGCCCTTC
       L  I  I  S     F  R  N     S  V  T     P  T  N  F     I  T  D     W  A  F     L  Q  V  S
 421   TGATCATCTC GTTTCGCAAT AGCGTGACCC CCACAAACTT CATCACCGAT TGGGCATTCC TTCAAGTCAG
          A  P  T     A  C  S     G  C  R  A     H  K  G     F  W  S     A  A  V  A     A  D  K
 491   CGCGCCTACC GCGTGCTCCG GATGCCGAGC ACATAAAGGG TTCTGGTCGG CGGCCGTGGC CGCCGACAAG
          A  L  D     G  S  I  R     E  A  K     A  R  Y     P  E  Y  E     L  T  L     T  G  H
 561   GCTTTAGATG GTTCCATCAG GGAGGCAAAG GCCAGATACC CAGAGTACGA ACTGACGTTG ACTGGGCATA
          S  L  G  G     A  L  A     T  L  H     A  I  F  L     R  N  R     G  V  A     V  D  S
 631   GTTTGGGAGG TGCACTTGCA ACGCTTCATG CAATTTTCCT GAGGAATAGA GGAGTTGCTG TTGATTCTGT
                                                                                              Y
 701   AAGTTGAGGC TTTGCCGCAA TGACGACCCG AGCAACTTGA TGGCTGCTGA TGCTGACTGG ACTGCTAGTA
          T  F  G     A  P  S     V  G  D  Y     A  M  A     D  Y  I     T  N  G     P  G  S  D
 771   TACCTTCGGC GCGCCATCGG TTGGTGACTA CGCAATGGCC GATTACATCA CGAACGGGCC CGGTAGCGAC
          N  G  R     N  Y  R  V     T  H  L     N  D  V     F  P  K  M     L  Y  R     A  S  R
 841   AATGGGAGGA ACTATCGCGT TACGCACCTG AATGACGTCT TTCCAAAAAT GCTCTACCGT GCGTCTAGGA
          M  P  V     A  D  R  L     V  Q  E     Y  S  Q  S     G  P  E     Y  W  I     T  S  G  F
 911   TGCCGGTTGC AGATCGGCTG GTACAAGAGT ACAGCCAGTC CGGGCCAGAG TACTGGATTA CGTCTGGCTT
          G  E  P     V  T  T     A  D  V  H     I  L  E     G  V  D     N  E  Q  G     N  L  G
 981   CGGCGAGCCT GTTACAACTG CGGATGTGCA CATCCTTGAG GGCGTGGATA ATGAGCAGGG CAATCTGGGA
          R  E  P     G  S  L  R     D  H  M     W  Y  L     G  A  T  D     A  C  P     L  G  *
1051   AGAGAACCTG GCAGTCTGAG GGACCATATG TGGTATTTGG GGGCGACAGA TGCTTGCCCA CTAGGCTGA
```

Fig. 20

```
  M   T   V   S   L   D   S   L   F   L   T   L   I   I   F   L   T   R   L   C   S
ATGACGGTGTCTCTTGACAGTTTATTCCTTACACTTATTATATTCCTCACGAGGCTATGCAGC
  V   S   T   A   H   V   V   P   L   E   A   S   K   D   P   E   N   I   T   P   G
GTCTCGACCGCTCACGTGGTACCCCTTGAGGCCAGCAAGGATCCCGAAAATATCACGCCAGGG
  R   Q   I   S   Q   E   L   F   D   S   I   E   E   L   A   H   I   V   D   I   A
AGGCAAATCTCCCAGGAACTATTTGACTCTATTGAGGAGCTGGCTCATATTGTCGATATCGCC
  Y   C   I   G   T   T   G   I   R   K   P   F   Q   C   L   S   H   C   D   E   L
TACTGCATTGGGACTACTGGCATTAGAAAGCCGTTCCAATGCCTCAGTCACTGTGATGAGCTA
  K   G   F   E   L   I   N
AAAGGGTTTGAACTAATCAACGTGCGCTTTTCCACAGACGATCTACCCGAGCCGTTTGAGAGA
                                      T   W   H   T   G   P   F   L   S   D   S   C
TAGTAGCTGACTAGATAGAAACTCAGACATGGCATACAGGTCCCTTTCTCTCTGATTCCTGCG
  G   Y   I   A   L   S   H   P   P   S   P   K   R   I   I   V   A   F   R   G   T
GCTACATCGCCCTCTCGCATCCCCCCTCACCGAAGCGAATCATAGTCGCTTTCCGCGGTACAT
  Y   S   I   P   N   A   I   V   D   L   S   M   Y   P   Q   E   Y   I   P   F   S
ACTCAATCCCAACGCAATAGTTGACCTTTCCATGTATCCCCAGGAATACATACCGTTTTCCC
  P   G   N   D   T   D   G   D   A   P   K   C   E   D   C   W   V   H   L   G   F
CAGGCAACGATACTGACGGCGATGCACCGAAGTGCGAGGACTGTTGGGTCCATTTAGGCTTCA
  M   N   A   W   R   L   T   R   A   T   I   L   D   T   I   S   A   A   R   D   Q
TGAACGCATGGCGTTTAACCCGCGCAACAATCCTAGACACCATCTCCGCAGCAAGAGACCAAT
  Y   P   D   Y   A   L   T   L   V   G   H   S   L   G   G   A   V   A   A   L   A
ACCCTGATTACGCTCTAACCCTAGTAGGCCACTCTCTCGGCGGCGCAGTTGCCGCTCTCGCAG
  G   T   E   M   Q   L   R   G   W   E   P   V   V   T   T   F   G   E   P   R   V
GAACAGAAATGCAGCTCCGCGGATGGGAACCCGTCGTGACGACTTTCGGGGAACCAAGGGTAG
  G   N   K   A   F   V   D   Y   L   D   T   V   F   R   L   E   S   G   N   E   R
GGAATAAGGCGTTTGTCGACTATCTAGACACCGTGTTCCGCCTGGAATCTGGCAATGAGCGGG
  G   W   K   F   R   R   V   T   H   V   N   D   P   V   P   L   I   P   L   T   E
TGTGGAAATTCCGCCGGGTGACGCATGTGAATGACCCTGTACCCCTAATCCCGCTTACAGAAT
  W   G   Y   E   M   H   S   G   E   I   Y   I   D   R   V   E   L   P   F   S   V
GGGGCTACGAGATGCACAGCGGAGAGATTTATATTGACCGCGTTGAGCTTCCATTTTCTGTTG
  D   D   V   R   Y   C   Q   G   G   S   D   P   N   C   I   S   D   A   E   G   K
ACGATGTCAGGTACTGCCAGGGCGGGTCCGATCCAAACTGCATTTCAGACGCGGAGGGGAAGA
  S   T   T   F   S   P   Y   S   S   Q   G   F   D   L   S   E   S   N   M   E   Q
GCACAACTTTCTCCCCATATAGCTCGCAGGGCTTTGATCTCTCCGAATCCAACATGGAGCAGC
  Q   V   L   S   R   S   P   H   Q   S   K   D   Q   Q   E   N   E   K   G   A
AAGTCCTTTCGCGCTCGCCGCACCAGTCGAAGGATCAGCAACAGGAGAATGAGAAGGGAGCTT
  F   P   Y   L   E   S   Q   T   S   C   L   P   W   G   I   L   P   P   R   F
TTCCATATCTGGAATCCCAGAGTACCTCGTGTCTGCCATGGGGTATACTTCCACCTAGGTTTC
  R   L   W   E   L   F   Y   S   H   R   D   Y   F   I   R   L   G   L   C   V   P
GACTGTGGGAGCTATTCTACTCTCATCGTGACTACTTTATTCGTTTGGGGCTTTGCGTTCCCA
  K   G   D   L   S   G   G   *
AGGGAGATTTGTCAGGGGGGTGA
```

Fig. 23

POLYPEPTIDES HAVING LIPASE ACTIVITY AND POLYNUCLEOTIDES ENCODING SAME

CROSS-REFERENCE TO RELATED APPLICATIONS

This application is a divisional application of U.S. patent application Ser. No. 12/696,676, filed Jan. 29, 2010, now U.S. Pat. No. 8,377,675, which is a divisional application of U.S. patent application Ser. No. 11/241,677, filed Sep. 30, 2005, now U.S. Pat. No. 7,666,630, which claims the benefit of U.S. Provisional Application No. 60/614,508, filed Sep. 30, 2004, U.S. Provisional Application No. 60/621,304, filed Oct. 21, 2004, and U.S. Provisional Application No. 60/621,222, filed Oct. 21, 2004, which applications are incorporated herein by reference.

BACKGROUND OF THE INVENTION

1. Field of the Invention

The present invention relates to isolated polypeptides having lipase activity and isolated polynucleotides encoding the polypeptides. The invention also relates to nucleic acid constructs, vectors, and host cells comprising the polynucleotides as well as methods for producing and using the polypeptides.

2. Description of the Related Art

Triacylglycerol hydrolyzing enzymes are enzymes that catalyze the hydrolysis or formation of triglycerides. Triacylglycerol hydrolyzing enzymes are a versatile group of enzymes and often have more than one activity such as lipase, phospholipase, lysophospholipase, cholesterol esterase, cutinase, amidase, galactolipase, and other esterase type of activities. Which activity is the predominant activity will depend on the application of the enzyme and the conditions.

Triacylglycerol hydrolyzing enzymes belong to the IUBMB Enzyme Nomenclature 3.1.1. EC 3 refers to hydrolases, EC 3.1 refers to acting on ester bonds, and EC 3.1.1 refers to carboxylic ester hydrolases. Related enzymes are classified in EC 3.1.4, which refers to phosphoric diester hydrolases.

Lipases (EC 3.1.1.3) are enzymes that catalyze the hydrolysis of a wide range of carboxy esters, e.g., triglycerides to release fatty acid. Esterases (EC 3.1.1.1) are enzymes that catalyze the hydrolysis of water-soluble carboxylic esters, including short-chain fatty acid triglycerides, to produce an alcohol and a carboxylic acid anion.

Some lipases also have phospholipase activity and/or galactolipase activity (see, for example, U.S. Pat. No. 6,103, 505 and U.S. Pat. No. 6,852,346).

Phospholipases are enzymes that catalyze the hydrolysis of phospholipids which consist of a glycerol backbone with two fatty acids in the sn1 and sn2 positions, which is esterified with a phosphoric acid in the sn3 position. The phosphoric acid may, in turn, be esterified to an amino alcohol.

There are several types of phospholipases which catalyze the hydrolysis of the fatty acyl moieties. These phospholipases include phospholipase $A_1$ (EC 3.1.1.32), phospholipase $A_2$ (EC 3.1.1.4), and lysophospholipase (EC 3.1.1.5). Phospholipase C (EC 3.1.4.3) and phospholipase D (EC 3.1.4.4) hydrolyze the phosphoric acid group from a phospholipid, but do not hydrolyze fatty acids like phospholipase $A_1$, phospholipase $A_2$ and phospholipase B.

Phospholipase $A_1$ (EC 3.1.1.32) catalyzes the deacylation of one fatty acyl group in the sn1 position from a diacylglycerophospholipid to produce lysophospholipid and fatty acid. Phospholipase $A_2$ (EC 3.1.1.4) catalyzes the deacylation of one fatty acyl group in the sn2 position from a diacylglycerophospholipid to produce lysophospholipid and fatty acid. Lysophospholipase (EC 3.1.1.5), also known as phospholipase B, catalyzes the hydrolysis of the fatty acyl group in a lysophospholipid. Phospholipase C (EC 3.1.4.3) catalyzes the hydrolysis of phosphatidylcholine to 1,2-diacylglycerol and choline phosphate. Phospholipase D (EC 3.1.4.4) catalyzes the hydrolysis of the terminal phosphate diester bond of phosphatidylcholine to produce choline and phosphatidic acid.

Galactolipases (EC 3.1.1.26) catalyze the hydrolysis of galactolipids by removing one or two fatty acids.

Detergents formulated with lipolytic enzymes are known to have improved properties for removing fatty stains. For example, LIPOLASE™ (Novozymes A/S, Bagsværd, Denmark), a microbial lipase obtained from the fungus *Thermomyces lanuginosus* (also called *Humicola lanuginosa*), has been introduced into many commercial brands of detergent. Lipases have also been used in degumming processes and baking.

El-Shahed et al., 1988, *Eqypt. J. Microbiol.* 23: 357-372 and Mohawed et al., 1988, *Egypt. J. Microbiol.* 23: 537-547 disclose two *Aspergillus fumigatus* lipases.

WO 03/12071 discloses a gene encoding a lipase from *Aspergillus fumigatus*.

Mayordomo et al., 2000, *J. Agric. Chem.* 48: 105-109 disclose the isolation, purification, and characterization of a cold-active lipase from *Aspergillus nidulans*.

Lipases have many commercial uses but very few lipases that work under application conditions and can be produced with high yields by microbial fermentation have been identified. There is a need in the art for alternative lipases with improved properties.

It is an object of the present invention to provide polypeptides having lipase activity and polynucleotides encoding the polypeptides.

SUMMARY OF THE INVENTION

The present invention relates to isolated polypeptides having lipase activity selected from the group consisting of:

(a) a polypeptide having an amino acid sequence which has at least 60% identity with the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16;

(b) a polypeptide which is encoded by a nucleotide sequence which hybridizes under at least medium stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, or (iii) a complementary strand of (i) or (ii); and (c) a variant comprising a conservative substitution, deletion, and/or insertion of one or more amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16.

The present invention also relates to isolated polynucleotides encoding polypeptides having lipase activity, selected from the group consisting of:

(a) a polynucleotide encoding a polypeptide having an amino acid sequence which has at least 60% identity with the mature polypeptide of SEQ ID NO: 2, SEQ ID NO: 6, SEQ ID NO: 8, SEQ ID NO: 10, SEQ ID NO: 12, SEQ ID NO: 14, or SEQ ID NO: 16;

(b) a polynucleotide having at least 60% identity with the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; and (c) a polynucleotide which hybridizes under at least medium stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, or (iii) a complementary strand of (i) or (ii).

In a preferred aspect, the mature polypeptide is amino acids 25 to 396 of SEQ ID NO: 2, amino acids 25 to 283 of SEQ ID NO: 4, amino acids 20 to 318 of SEQ ID NO: 6, amino acids 19 to 348 of SEQ ID NO: 8, amino acids 25 to 393 of SEQ ID NO: 10, amino acids 20 to 294 of SEQ ID NO: 12, amino acids 25 to 308 of SEQ ID NO: 14, or amino acids 26 to 404 of SEQ ID NO: 16. In another preferred aspect, the mature polypeptide coding sequence is nucleotides 73 to 1256 of SEQ ID NO: 1, nucleotides 73 to 944 of SEQ ID NO: 3, nucleotides 58 to 1085 of SEQ ID NO: 5, nucleotides 55 to 1044 of SEQ ID NO: 7, nucleotides 73 to 1179 of SEQ ID NO: 9, nucleotides 58 to 1038 of SEQ ID NO: 11, nucleotides 73 to 1119 of SEQ ID NO: 13, or nucleotides 76 to 1280 of SEQ ID NO: 15.

The present invention also relates to nucleic acid constructs, recombinant expression vectors, and recombinant host cells comprising the polynucleotides.

The present invention also relates to methods for producing such a polypeptide having lipase activity comprising: (a) cultivating a recombinant host cell comprising a nucleic acid construct comprising a polynucleotide encoding the polypeptide under conditions conducive for production of the polypeptide; and (b) recovering the polypeptide.

The present invention also relates to methods of using the polypeptides having lipase activity in detergents, degumming, and baking.

The present invention further relates to nucleic acid constructs comprising a gene encoding a protein, wherein the gene is operably linked to a nucleotide sequence encoding a signal peptide comprising or consisting of nucleotides 1 to 72 of SEQ ID NO: 1, nucleotides 1 to 72 of SEQ ID NO: 3, nucleotides 1 to 57 of SEQ ID NO: 5, nucleotides 1 to 54 of SEQ ID NO: 7, nucleotides 1 to 72 of SEQ ID NO: 9, nucleotides 1 to 57 of SEQ ID NO: 11, nucleotides 1 to 72 of SEQ ID NO: 13, or nucleotides 1 to 75 of SEQ ID NO: 15, wherein the gene is foreign to the nucleotide sequence.

BRIEF DESCRIPTION OF THE FIGURES

FIG. 2 shows the genomic DNA sequence and the deduced amino acid sequence of an *Aspergillus fumigatus* lipase (*Aspergillus fumigatus* lip1, SEQ ID NOs: 1 and 2, respectively).
FIG. 5 shows a restriction map of pBM120a.
FIG. 8 shows the genomic DNA sequence and the deduced amino acid sequence of an *Aspergillus fumigatus* lipase (*Aspergillus fumigatus* lip2, SEQ ID NOs: 3 and 4, respectively).
FIGS. 10A and 10B show the genomic DNA sequence and the deduced amino acid sequence of a *Magnaporthe grisea* lipase (*Magnaporthe grisea* lip1, SEQ ID NOs: 5 and 6, respectively).
FIG. 13 shows the genomic DNA sequence and the deduced amino acid sequence of a *Magnaporthe grisea* lipase (*Magnaporthe grisea* lip2, SEQ ID NOs: 7 and 8, respectively).
FIG. 15 shows the genomic DNA sequence and the deduced amino acid sequence of a *Magnaporthe grisea* lipase (*Magnaporthe grisea* lip3, SEQ ID NOs: 9 and 10, respectively).
FIG. 17 shows the genomic DNA sequence and the deduced amino acid sequence of an *Aspergillus nidulans* lipase (*Aspergillus nidulans* lip1, SEQ ID NOs: 11 and 12, respectively).
FIG. 20 shows the genomic DNA sequence and the deduced amino acid sequence of an *Aspergillus nidulans* lipase (*Aspergillus nidulans* lip2, SEQ ID NOs: 13 and 14, respectively).
FIG. 23 shows the genomic DNA sequence and the deduced amino acid sequence of an *Aspergillus nidulans* lipase (*Aspergillus nidulans* lip3, SEQ ID NOs: 15 and 16, respectively).

DEFINITIONS

Figure 1:
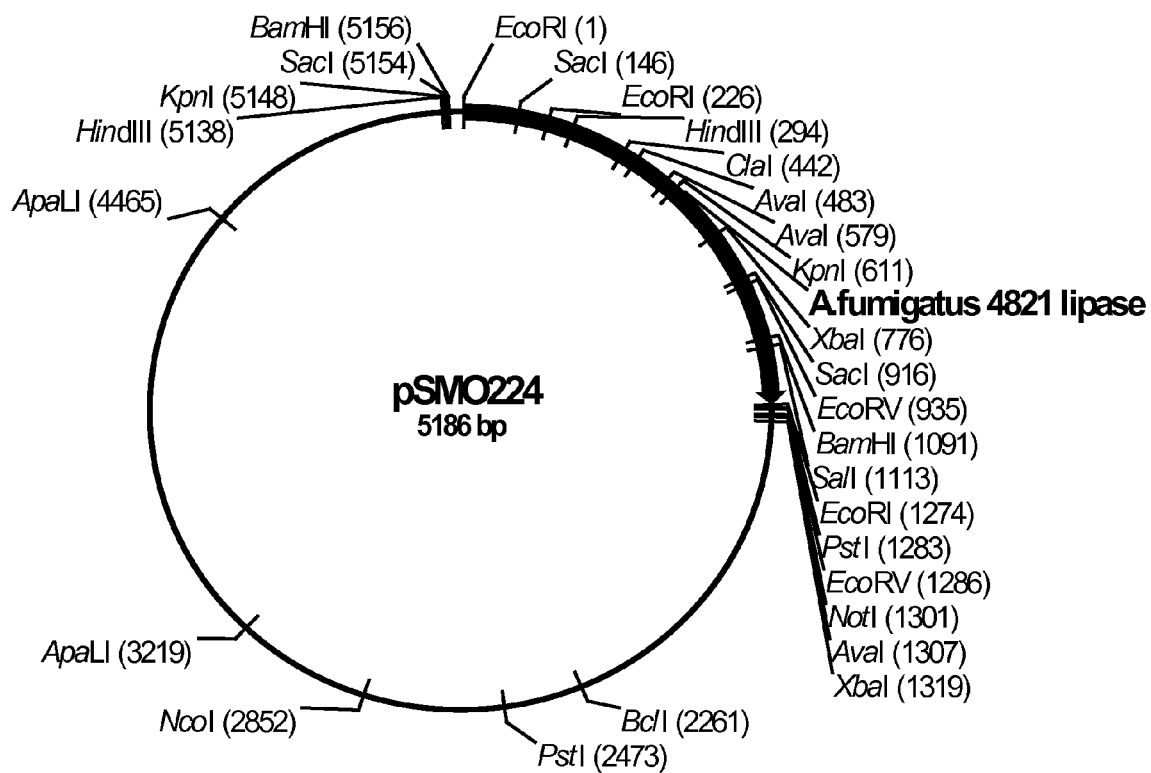
FIG. 1 shows a restriction map of pSMO224.

Lipase activity: The term "lipase activity" is defined herein as a triacylglycerol acylhydrolase activity (E.C. 3.1.1.3) which catalyzes the hydrolysis of a triacylglycerol to fatty acid(s). The substrate spectrum of lipases includes triglycerides, diglycerides, and monoglycerides, but for the purpose of the present invention, lipase activity is determined using p-nitrophenyl butyrate as substrate. One unit of lipase activity equals the amount of enzyme capable of releasing 1 µmole of butyric acid per minute at pH 7.5, 25° C. Encompassed within the term "lipase activity" are polypeptides that also have phopholipase activity and/or galactolipase activity, as defined herein.

The polypeptides of the present invention have at least 20%, preferably at least 40%, more preferably at least 50%, more preferably at least 60%, more preferably at least 70%, more preferably at least 80%, even more preferably at least 90%, most preferably at least 95%, and even most preferably at least 100% of the lipase activity of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16.

Phospholipase activity: The term "phospholipase activity" is defined herein as a phosphatidyl acylhydrolase (EC 3.1.1.4, EC 3.1.1.5, and EC 3.1.1.32) which catalyzes the hydrolysis of a fatty acid from a phospholipid. Phospholipids consist of a glycerol backbone with two fatty acids in the sn1 and sn2 positions, which is esterified with a phosphoric acid in the sn3 position. The phosphoric acid may, in turn, be esterified with an amino alcohol.

Phospholipase A₁ (EC 3.1.1.32) catalyzes the deacylation of one fatty acyl group in the sn1 position from a diacylglycerophospholipid to produce lysophospholipid and fatty acid.

Phospholipase A₂ (EC 3.1.1.4) catalyzes the deacylation of one fatty acyl group in the sn2 position from a diacylglycerophospholipid to produce lysophospholipid and fatty acid.

Lysophospholipase (EC 3.1.1.5), also known as phospholipase B, catalyzes the hydrolysis of the fatty acyl group in a lysophospholipid.

For purposes of the present invention, phospholipase A₁, phospholipase A₂, and lysophospholipase activity is determined according to WO 2005/040410 using phosphatidylcholines derived from soy (Avanti Polar Lipids Inc., Alabama, USA) as substrate.

Galactolipase Activity: The term "galactolipase activity" is defined herein as a 1,2-diacyl-3-beta-D-galactosyl-sn-glycerol acylhydrolase (EC 3.1.1.26) which catalyzes the hydrolysis of galactolipids by removing one or two fatty acids. Galactolipase activity is determined according to WO 2005/040410 using digalactosyldiglyceride (DGDG) or monogalactosyldiglyceride (MGDG) extracted from wheat flour as substrate. DGDG is a galactolipid that consists of two fatty acids and a digalactose. MGDG is a galactolipid that consists of two fatty acids and a galactose.

Isolated polypeptide: The term "isolated polypeptide" as used herein refers to a polypeptide which is at least 20% pure, preferably at least 40% pure, more preferably at least 60% pure, even more preferably at least 80% pure, most preferably at least 90% pure, and even most preferably at least 95% pure, as determined by SDS-PAGE.

Substantially pure polypeptide: The term "substantially pure polypeptide" denotes herein a polypeptide preparation which contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation.

The polypeptides of the present invention are preferably in a substantially pure form. In particular, it is preferred that the polypeptides are in "essentially pure form", i.e., that the polypeptide preparation is essentially free of other polypeptide material with which it is natively associated. This can be accomplished, for example, by preparing the polypeptide by means of well-known recombinant methods or by classical purification methods.

Herein, the term "substantially pure polypeptide" is synonymous with the terms "isolated polypeptide" and "polypeptide in isolated form."

Mature polypeptide: The term "mature polypeptide" is defined herein as a polypeptide having lipase activity that is in its final form following translation and any post-translational modifications, such as N-terminal processing, C-terminal truncation, glycosylation, etc.

Identity: The relatedness between two amino acid sequences or between two nucleotide sequences is described by the parameter "identity".

For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

For purposes of the present invention, the degree of identity between two nucleotide sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Homologous sequence: The term "homologous sequence" is defined herein as a predicted protein which gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Thermomyces lanuginosus* lipase (Accession No. O59952).

Polypeptide fragment: The term "polypeptide fragment" is defined herein as a polypeptide having one or more amino acids deleted from the amino and/or carboxyl terminus of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16; or a homologous sequence thereof; wherein the fragment has lipase activity. In a preferred aspect, a fragment contains at least 325 amino acid residues, more preferably at least 340 amino acid residues, and most preferably at least 355 amino acid residues of the mature polypeptide of SEQ ID NO: 2 or a homologous sequence thereof. In another preferred aspect, a fragment contains at least 215 amino acid residues, more preferably at least 230 amino acid residues, and most preferably at least 245 amino acid residues of the mature polypeptide of SEQ ID NO: 4 or a homologous sequence thereof. In another preferred aspect, a fragment contains at least 255 amino acid residues, more preferably at least 270 amino acid residues, and most preferably at least 285 amino acid residues of the mature polypeptide of SEQ ID NO: 6 or a homologous sequence thereof. In another preferred aspect, a fragment contains at least 285 amino acid residues, more preferably at least 300 amino acid residues, and most preferably at least 315 amino acid residues of the mature polypeptide of SEQ ID NO: 8 or a homologous sequence thereof. In another preferred aspect, a fragment contains at least 320 amino acid residues, more preferably at least 335 amino acid residues, and most preferably at least 350 amino acid residues of the mature polypeptide of SEQ ID NO: 10 or a homologous sequence thereof. In another preferred aspect, a fragment contains at least 230 amino acid residues, more preferably at least 245 amino acid residues, and most preferably at least 260 amino acid residues of the mature polypeptide of SEQ ID NO: 12 or a homologous sequence thereof. In another preferred aspect, a fragment contains at least 240 amino acid residues, more preferably at least 255 amino acid residues, and most preferably at least 270 amino acid residues of the mature polypeptide of SEQ ID NO: 14 or a homologous sequence thereof. In another preferred aspect, a fragment contains at least 320 amino acid residues, more preferably at least 340 amino acid residues, and most preferably at least 360 amino acid residues of the mature polypeptide of SEQ ID NO: 16 or a homologous sequence thereof.

Subsequence: The term "subsequence" is defined herein as a nucleotide sequence having one or more nucleotides deleted from the 5' and/or 3' end of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; or a homologous sequence thereof; wherein the subsequence encodes a polypeptide fragment having lipase activity. In a preferred aspect, a subsequence contains at least 975 nucleotides, more preferably at least 1020 nucleotides, and most preferably at least 1060 nucleotides of the mature polypeptide coding sequence of SEQ ID NO: 1 or a homologous sequence thereof. In another preferred aspect, a subsequence contains at least 645 nucleotides, more preferably at least 690 nucleotides, and most preferably at least 735 nucleotides of the mature polypeptide coding sequence of SEQ ID NO: 3 or a homologous sequence thereof. In a preferred aspect, a subsequence contains at least 765 nucleotides, more preferably at least 810 nucleotides, and most preferably at least 855 nucleotides of the mature polypeptide coding sequence of SEQ ID NO: 5 or a homologous sequence thereof. In another preferred aspect, a subsequence contains at least 855 nucleotides, more preferably at least 900 nucleotides, and most preferably at least 945 nucleotides of the mature polypeptide coding sequence of SEQ ID NO: 7 or a homologous sequence thereof. In another preferred aspect, a subsequence contains at least 960 nucleotides, more preferably at least 1005 nucleotides, and most preferably at least 1050 nucleotides of the mature polypeptide coding sequence of SEQ ID NO: 9 or a homologous sequence thereof. In a preferred aspect, a subsequence contains at least 690 nucleotides, more preferably at least 735 nucleotides, and most preferably at least 780 nucleotides of the mature polypeptide coding sequence of SEQ ID NO: 11 or a homologous sequence thereof. In another preferred aspect, a subsequence contains at least 720 nucleotides, more preferably at least 765 nucleotides, and most preferably at least 810 nucleotides of the mature polypeptide coding sequence of SEQ ID NO: 13 or a homologous sequence thereof. In another preferred aspect, a subsequence contains at least 1020 nucleotides, more preferably at least 1020 nucleotides, and most preferably at least 1080 nucleotides of the mature polypeptide coding sequence of SEQ ID NO: 15 or a homologous sequence thereof.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide which is at least 20% pure, preferably at least 40% pure, more preferably at least 60% pure, even more preferably at least 80% pure, most preferably at least 90% pure, and even most preferably at least 95% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form. In particular, it is preferred that the polynucleotides disclosed herein are in "essentially pure form", i.e., that the polynucleotide preparation is essentially free of other polynucleotide material with which it is natively associated. Herein, the term "substantially pure polynucleotide" is synonymous with the terms "isolated polynucleotide" and "polynucleotide in isolated form." The polynucleotides may be of genomic, cDNA, RNA, semisynthetic, synthetic origin, or any combinations thereof.

Mature polypeptide coding sequence: The term "mature polypeptide coding sequence" is defined herein as a nucleotide sequence that encodes a mature polypeptide having lipase activity.

cDNA: The term "cDNA" is defined herein as a DNA molecule which can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA which is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature. The term nucleic acid construct is synonymous with the term "expression cassette" when the nucleic acid construct contains the control sequences required for expression of a coding sequence of the present invention.

Control sequence: The term "control sequences" is defined herein to include all components, which are necessary or advantageous for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG and TGA. The coding sequence may be a DNA, cDNA, or recombinant nucleotide sequence.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the invention, and which is operably linked to additional nucleotides that provide for its expression.

Host cell: The term "host cell", as used herein, includes any cell type which is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16; or a homologous sequence thereof; as well as genetic manipulation of the DNA encoding such a polypeptide. The modification can be substitutions, deletions and/or insertions of one or more amino acids as well as replacements of one or more amino acid side chains.

Artificial variant: When used herein, the term "artificial variant" means a polypeptide having lipase activity produced by an organism expressing a modified nucleotide sequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; or a homologous sequence thereof. The modified nucleotide sequence is obtained through human intervention by modification of the nucleotide sequence disclosed in SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; or a homologous sequence thereof.

DETAILED DESCRIPTION OF THE INVENTION

Polypeptides Having Lipase Activity

In a first aspect, the present invention relates to isolated polypeptides having an amino acid sequence which has a degree of identity to the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16, of at least 60%, preferably at least 65%, more preferably at least 70%, more preferably at least 75%, more preferably at least 80%, more preferably at least 85%, even more preferably at least 90%, most preferably at least 95%, and even most preferably at least 97%, 98%, or 99%, which have lipase activity (hereinafter "homologous polypeptides"). In a preferred aspect, the homologous polypeptides have an amino acid sequence which differs by ten amino acids, preferably by five amino acids, more preferably by four amino acids, even more preferably by three amino acids, most preferably by two amino acids, and even most preferably by one amino acid from the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16.

A polypeptide of the present invention preferably comprises the amino acid sequence of SEQ ID NO: 2 or an allelic variant thereof; or a fragment thereof that has lipase activity. In a preferred aspect, a polypeptide comprises the amino acid sequence of SEQ ID NO: 2. In another preferred aspect, a polypeptide comprises the mature polypeptide of SEQ ID NO: 2. In another preferred aspect, a polypeptide comprises amino acids 25 to 396 of SEQ ID NO: 2, or an allelic variant thereof; or a fragment thereof that has lipase activity. In another preferred aspect, a polypeptide comprises amino acids 25 to 396 of SEQ ID NO: 2. In another preferred aspect, a polypeptide consists of the amino acid sequence of SEQ ID NO: 2 or an allelic variant thereof; or a fragment thereof that has lipase activity. In another preferred aspect, a polypeptide consists of the amino acid sequence of SEQ ID NO: 2. In another preferred aspect, a polypeptide consists of the mature polypeptide of SEQ ID NO: 2. In another preferred aspect, a polypeptide consists of amino acids 25 to 396 of SEQ ID NO: 2 or an allelic variant thereof; or a fragment thereof that has lipase activity. In another preferred aspect, a polypeptide consists of amino acids 25 to 396 of SEQ ID NO: 2.

A polypeptide of the present invention preferably comprises the amino acid sequence of SEQ ID NO: 4, or an allelic variant thereof; or a fragment thereof that has lipase activity. In a preferred aspect, a polypeptide comprises the amino acid sequence of SEQ ID NO: 4. In another preferred aspect, a polypeptide comprises the mature polypeptide of SEQ ID NO: 4. In another preferred aspect, a polypeptide comprises amino acids 25 to 283 of SEQ ID NO: 4, or an allelic variant thereof; or a fragment thereof that has lipase activity. In another preferred aspect, a polypeptide comprises amino acids 25 to 283 of SEQ ID NO: 4. In another preferred aspect, a polypeptide consists of the amino acid sequence of SEQ ID NO: 4 or an allelic variant thereof; or a fragment thereof that has lipase activity. In another preferred aspect, a polypeptide consists of the amino acid sequence of SEQ ID NO: 4. In another preferred aspect, a polypeptide consists of amino acids 25 to 283 of SEQ ID NO: 4 or an allelic variant thereof; or a fragment thereof that has lipase activity. In another preferred aspect, a polypeptide consists of amino acids 25 to 283 of SEQ ID NO: 4.

A polypeptide of the present invention preferably comprises the amino acid sequence of SEQ ID NO: 6, or an allelic variant thereof; or a fragment thereof that has lipase activity. In a preferred aspect, a polypeptide comprises the amino acid sequence of SEQ ID NO: 6. In another preferred aspect, a polypeptide comprises the mature polypeptide of SEQ ID NO: 6. In another preferred aspect, a polypeptide comprises amino acids 20 to 318 of SEQ ID NO: 6, or an allelic variant thereof; or a fragment thereof that has lipase activity. In another preferred aspect, a polypeptide comprises amino acids 20 to 318 of SEQ ID NO: 6. In another preferred aspect, a polypeptide consists of the amino acid sequence of SEQ ID NO: 6 or an allelic variant thereof; or a fragment thereof that has lipase activity. In another preferred aspect, a polypeptide consists of the amino acid sequence of SEQ ID NO: 6. In another preferred aspect, a polypeptide consists of amino acids 20 to 318 of SEQ ID NO: 6 or an allelic variant thereof; or a fragment thereof that has lipase activity. In another preferred aspect, a polypeptide consists of amino acids 20 to 318 of SEQ ID NO: 6.

A polypeptide of the present invention preferably comprises the amino acid sequence of SEQ ID NO: 8, or an allelic variant thereof; or a fragment thereof that has lipase activity. In a preferred aspect, a polypeptide comprises the amino acid sequence of SEQ ID NO: 8. In another preferred aspect, a polypeptide comprises the mature polypeptide of SEQ ID NO: 8. In another preferred aspect, a polypeptide comprises amino acids 19 to 348 of SEQ ID NO: 8, or an allelic variant thereof; or a fragment thereof that has lipase activity. In another preferred aspect, a polypeptide comprises amino acids 19 to 348 of SEQ ID NO: 8. In another preferred aspect, a polypeptide consists of the amino acid sequence of SEQ ID NO: 8 or an allelic variant thereof; or a fragment thereof that has lipase activity. In another preferred aspect, a polypeptide consists of the amino acid sequence of SEQ ID NO: 8. In another preferred aspect, a polypeptide consists of amino acids 19 to 348 of SEQ ID NO: 8 or an allelic variant thereof; or a fragment thereof that has lipase activity. In another preferred aspect, a polypeptide consists of amino acids 19 to 348 of SEQ ID NO: 8.

A polypeptide of the present invention preferably comprises the amino acid sequence of SEQ ID NO: 10, or an allelic variant thereof; or a fragment thereof that has lipase activity. In a preferred aspect, a polypeptide comprises the amino acid sequence of SEQ ID NO: 10. In another preferred aspect, a polypeptide comprises the mature polypeptide of SEQ ID NO: 10. In another preferred aspect, a polypeptide comprises amino acids 25 to 393 of SEQ ID NO: 10, or an allelic variant thereof; or a fragment thereof that has lipase activity. In another preferred aspect, a polypeptide comprises amino acids 25 to 393 of SEQ ID NO: 10. In another preferred aspect, a polypeptide consists of the amino acid sequence of SEQ ID NO: 10 or an allelic variant thereof; or a fragment thereof that has lipase activity. In another preferred aspect, a polypeptide consists of the amino acid sequence of SEQ ID NO: 10. In another preferred aspect, a polypeptide consists of amino acids 25 to 393 of SEQ ID NO: 10 or an allelic variant thereof; or a fragment thereof that has lipase activity. In another preferred aspect, a polypeptide consists of amino acids 25 to 393 of SEQ ID NO: 10.

A polypeptide of the present invention preferably comprises the amino acid sequence of SEQ ID NO: 12, or an allelic variant thereof; or a fragment thereof that has lipase activity. In a preferred aspect, a polypeptide comprises the amino acid sequence of SEQ ID NO: 12. In another preferred aspect, a polypeptide comprises the mature polypeptide of SEQ ID NO: 12. In another preferred aspect, a polypeptide comprises amino acids 20 to 294 of SEQ ID NO: 12, or an allelic variant thereof; or a fragment thereof that has lipase activity. In another preferred aspect, a polypeptide comprises amino acids 20 to 294 of SEQ ID NO: 12. In another preferred aspect, a polypeptide consists of the amino acid sequence of SEQ ID NO: 12 or an allelic variant thereof; or a fragment thereof that has lipase activity. In another preferred aspect, a polypeptide consists of the amino acid sequence of SEQ ID NO: 12. In another preferred aspect, a polypeptide consists of amino acids 20 to 294 of SEQ ID NO: 12 or an allelic variant thereof; or a fragment thereof that has lipase activity. In another preferred aspect, a polypeptide consists of amino acids 20 to 294 of SEQ ID NO: 12.

A polypeptide of the present invention preferably comprises the amino acid sequence of SEQ ID NO: 14, or an allelic variant thereof; or a fragment thereof that has lipase activity. In a preferred aspect, a polypeptide comprises the amino acid sequence of SEQ ID NO: 14. In another preferred aspect, a polypeptide comprises the mature polypeptide of SEQ ID NO: 14. In another preferred aspect, a polypeptide comprises amino acids 25 to 308 of SEQ ID NO: 14, or an allelic variant thereof; or a fragment thereof that has lipase activity. In another preferred aspect, a polypeptide comprises amino acids 25 to 308 of SEQ ID NO: 14. In another preferred aspect, a polypeptide consists of the amino acid sequence of SEQ ID NO: 14 or an allelic variant thereof; or a fragment thereof that has lipase activity. In another preferred aspect, a polypeptide consists of the amino acid sequence of SEQ ID NO: 14. In another preferred aspect, a polypeptide consists of amino acids 25 to 308 of SEQ ID NO: 14 or an allelic variant thereof; or a fragment thereof that has lipase activity. In another preferred aspect, a polypeptide consists of amino acids 25 to 308 of SEQ ID NO: 14.

A polypeptide of the present invention preferably comprises the amino acid sequence of SEQ ID NO: 16, or an allelic variant thereof; or a fragment thereof that has lipase activity. In a preferred aspect, a polypeptide comprises the amino acid sequence of SEQ ID NO: 16. In another preferred aspect, a polypeptide comprises the mature polypeptide of SEQ ID NO: 16. In another preferred aspect, a polypeptide comprises amino acids 26 to 404 of SEQ ID NO: 16, or an allelic variant thereof; or a fragment thereof that has lipase activity. In another preferred aspect, a polypeptide comprises amino acids 26 to 404 of SEQ ID NO: 16. In another preferred aspect, a polypeptide consists of the amino acid sequence of SEQ ID NO: 16 or an allelic variant thereof; or a fragment thereof that has lipase activity. In another preferred aspect, a polypeptide consists of the amino acid sequence of SEQ ID NO: 16. In another preferred aspect, a polypeptide consists of amino acids 26 to 404 of SEQ ID NO: 16 or an allelic variant thereof; or a fragment thereof that has lipase activity. In another preferred aspect, a polypeptide consists of amino acids 26 to 404 of SEQ ID NO: 16.

In a second aspect, the present invention relates to isolated polypeptides having lipase activity which are encoded by polynucleotides which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (iii) a subsequence of (i) or (ii), or (iv) a complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15 contains at least 100 contiguous nucleotides or preferably at least 200 contiguous nucleotides. Moreover, the subsequence may encode a polypeptide fragment which has lipase activity. In a preferred aspect, the mature polypeptide coding sequence is nucleotides 73 to 1256 of SEQ ID NO: 1, nucleotides 73 to 944 of SEQ ID NO: 3, nucleotides 58 to 1085 of SEQ ID NO: 5, nucleotides 55 to 1044 of SEQ ID NO: 7, nucleotides 73 to 1179 of SEQ ID NO: 9, nucleotides 58 to 1038 of SEQ ID NO: 11, nucleotides 73 to 1116 of SEQ ID NO: 13, or nucleotides 76 to 1280 of SEQ ID NO: 15.

The nucleotide sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; or a subsequence thereof; as well as the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16; or a fragment thereof; may be used to design a nucleic acid probe to identify and clone DNA encoding polypeptides having lipase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes which are at least 600 nucleotides, at least preferably at least 700 nucleotides, more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other organisms may, therefore, be screened for DNA which hybridizes with the probes described above and which encodes a polypeptide having lipase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; or a subsequence thereof; the carrier material is used in a Southern blot.

For purposes of the present invention, hybridization indicates that the nucleotide sequence hybridizes to a labeled nucleic acid probe corresponding to the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15; its complementary strand; or a subsequence thereof; under very low to very high stringency conditions. Molecules to which the nucleic acid probe hybridizes under these conditions can be detected using X-ray film.

In a preferred aspect, the nucleic acid probe is the mature polypeptide coding sequence of SEQ ID NO: 1. In another preferred aspect, the nucleic acid probe is nucleotides 73 to 1256 of SEQ ID NO: 1. In another preferred aspect, the nucleic acid probe is a polynucleotide sequence which encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid pSMO224 which is contained in *E. coli* NRRL B-30774, wherein the polynucleotide sequence thereof encodes a polypeptide having lipase activity. In another preferred aspect, the nucleic acid probe is the mature polypeptide coding region contained in plasmid pSMO224 which is contained in *E. coli* NRRL B-30774.

In another preferred aspect, the nucleic acid probe is the mature polypeptide coding sequence of SEQ ID NO: 3. In another preferred aspect, the nucleic acid probe is nucleotides 73 to 944 of SEQ ID NO: 3. In another preferred aspect, the nucleic acid probe is a polynucleotide sequence which encodes the polypeptide of SEQ ID NO: 4, or a subsequence thereof. In another preferred aspect, the nucleic acid probe is SEQ ID NO: 3. In another preferred aspect, the nucleic acid probe is the polynucleotide sequence contained in plasmid pSMO223 which is contained in *E. coli* NRRL B-30773, wherein the polynucleotide sequence thereof encodes a polypeptide having lipase activity. In another preferred aspect, the nucleic acid probe is the mature polypeptide coding region contained in plasmid pSMO223 which is contained in *E. coli* NRRL B-30773.

In another preferred aspect, the nucleic acid probe is the mature polypeptide coding sequence of SEQ ID NO: 5. In another preferred aspect, the nucleic acid probe is nucleotides 58 to 1085 of SEQ ID NO: 5. In another preferred aspect, the nucleic acid probe is a polynucleotide sequence which encodes the polypeptide of SEQ ID NO: 6, or a subsequence thereof. In another preferred aspect, the nucleic acid probe is SEQ ID NO: 5. In another preferred aspect, the nucleic acid probe is the polynucleotide sequence contained in plasmid pHyGe026 which is contained in *E. coli* NRRL B-30772, wherein the polynucleotide sequence thereof encodes a polypeptide having lipase activity. In another preferred aspect, the nucleic acid probe is the mature polypeptide coding region contained in plasmid pHyGe026 which is contained in *E. coli* NRRL B-30772.

In another preferred aspect, the nucleic acid probe is the mature polypeptide coding sequence of SEQ ID NO: 7. In another preferred aspect, the nucleic acid probe is nucleotides 55 to 1044 of SEQ ID NO: 7. In another preferred aspect, the nucleic acid probe is a polynucleotide sequence which encodes the polypeptide of SEQ ID NO: 8, or a subsequence thereof. In another preferred aspect, the nucleic acid probe is SEQ ID NO: 7. In another preferred aspect, the nucleic acid probe is the polynucleotide sequence contained in plasmid pCrAm138 which is contained in *E. coli* NRRL B-30781, wherein the polynucleotide sequence thereof encodes a polypeptide having lipase activity. In another preferred aspect, the nucleic acid probe is the mature polypeptide coding region contained in plasmid pCrAm138 which is contained in *E. coli* NRRL B-30781.

In another preferred aspect, the nucleic acid probe is the mature polypeptide coding sequence of SEQ ID NO: 9. In another preferred aspect, the nucleic acid probe is nucleotides 73 to 1179 of SEQ ID NO: 9. In another preferred aspect, the nucleic acid probe is a polynucleotide sequence which encodes the polypeptide of SEQ ID NO: 10, or a subsequence thereof. In another preferred aspect, the nucleic acid probe is SEQ ID NO: 9. In another preferred aspect, the nucleic acid probe is the polynucleotide sequence contained in plasmid pBM135g which is contained in *E. coli* NRRL B-30779, wherein the polynucleotide sequence thereof encodes a polypeptide having lipase activity. In another preferred aspect, the nucleic acid probe is the mature polypeptide coding region contained in plasmid pBM135g which is contained in *E. coli* NRRL B-30779.

In another preferred aspect, the nucleic acid probe is the mature polypeptide coding sequence of SEQ ID NO: 11. In another preferred aspect, the nucleic acid probe is nucleotides 58 to 1038 of SEQ ID NO: 11. In another preferred aspect, the nucleic acid probe is a polynucleotide sequence which encodes the polypeptide of SEQ ID NO: 12, or a subsequence thereof. In another preferred aspect, the nucleic acid probe is SEQ ID NO: 11. In another preferred aspect, the nucleic acid probe is the polynucleotide sequence contained in plasmid pJLin171 which is contained in *E. coli* NRRL B-30755, wherein the polynucleotide sequence thereof encodes a polypeptide having lipase activity. In another preferred aspect, the nucleic acid probe is the mature polypeptide coding region contained in plasmid pJLin171 which is contained in *E. coli* NRRL B-30755.

In another preferred aspect, the nucleic acid probe is the mature polypeptide coding sequence of SEQ ID NO: 13. In another preferred aspect, the nucleic acid probe is nucleotides 73 to 1116 of SEQ ID NO: 13. In another preferred aspect, the nucleic acid probe is a polynucleotide sequence which encodes the polypeptide of SEQ ID NO: 18, or a subsequence thereof. In another preferred aspect, the nucleic acid probe is SEQ ID NO: 13. In another preferred aspect, the nucleic acid probe is the polynucleotide sequence contained in plasmid pJLin170 which is contained in *E. coli* NRRL B-30754, wherein the polynucleotide sequence thereof encodes a polypeptide having lipase activity. In another preferred aspect, the nucleic acid probe is the mature polypeptide coding region contained in plasmid pJLin170 which is contained in *E. coli* NRRL B-30754.

In another preferred aspect, the nucleic acid probe is the mature polypeptide coding sequence of SEQ ID NO: 15. In another preferred aspect, the nucleic acid probe is nucleotides 76 to 1280 of SEQ ID NO: 15. In another preferred aspect, the nucleic acid probe is a polynucleotide sequence which encodes the polypeptide of SEQ ID NO: 16, or a subsequence thereof. In another preferred aspect, the nucleic acid probe is SEQ ID NO: 15. In another preferred aspect, the nucleic acid probe is the polynucleotide sequence contained in plasmid pBM141 which is contained in *E. coli* NRRL B-30780, wherein the polynucleotide sequence thereof encodes a polypeptide having lipase activity. In another preferred aspect, the nucleic acid probe is the mature polypeptide coding region contained in plasmid pBM141 which is contained in *E. coli* NRRL B-30780.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes which are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to artificial variants comprising a conservative substitution, deletion, and/or insertion of one or more amino acids of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethyl proline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., lipase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides which are related to a polypeptide according to the invention.

Single or multiple amino acid substitutions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 25 to 396 of SEQ ID NO: 2, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 4, such as amino acids 25 to 283 of SEQ ID NO: 4, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 6, such as amino acids 20 to 318 of SEQ ID NO: 6, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 8, such as amino acids 19 to 348 of SEQ ID NO: 8, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 10, such as amino acids 25 to 393 of SEQ ID NO: 10, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 12, such as amino acids 20 to 294 of SEQ ID NO: 12, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 14, such as amino acids 25 to 308 of SEQ ID NO: 14, is 10, preferably 9, more preferably 8, more preferably 7, more preferably at most 6, more preferably 5, more preferably 4, even more preferably 3, most preferably 2, and even most preferably 1.

The total number of amino acid substitutions, deletions and/or insertions of the mature polypeptide of SEQ ID NO: 16, such as amino acids 26 to 404 of SEQ ID NO: 16, is 10, preferably 9, more preferably 8, more preferably 7, more preferably at most 6, more preferably 5, more preferably 4, even more preferably 3, most preferably 2, and even most preferably 1.

Sources of Polypeptides Having Lipase Activity

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention may be a bacterial polypeptide. For example, the polypeptide may be a gram positive bacterial polypeptide such as a *Bacillus* polypeptide having lipase activity, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* polypeptide having lipase activity; or a *Streptomyces* polypeptide having lipase activity, e.g., a *Streptomyces lividans* or *Streptomyces murinus* polypeptide having lipase activity; or a gram negative bacterial polypeptide having lipase activity, e.g., an *E. coli* or a *Pseudomonas* sp. polypeptide having lipase activity.

A polypeptide of the present invention may also be a fungal polypeptide, and more preferably a yeast polypeptide such as a *Candida, Kluyveromyces, Pichia, Saccharomyces, Schlzosaccharomyces*, or *Yarrowia* polypeptide; or more preferably a filamentous fungal polypeptide such as an *Acremonium, Aspergillus, Aureobasidium, Cryptococcus, Filibasidium, Fusarium, Humcola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* polypeptide having lipase activity.

In a preferred aspect, the polypeptide is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* polypeptide having lipase activity.

In another preferred aspect, the polypeptide is an *Aspergillus aculeatus, Aspergillus awamori, Aspergillus fumigatus, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humcola insolens, Humcola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* polypeptide having lipase activity.

In another preferred aspect, the polypeptide is a *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Thielavia terricola*, *Thielavia thermophila*, *Thielavia variospora*, or *Thielavia wareingii* polypeptide having lipase activity.

In a more preferred aspect, the polypeptide is an *Aspergillus fumigatus* polypeptide, e.g., the polypeptide of SEQ ID NO: 2 or SEQ ID NO: 4, or the mature polypeptide thereof.

In another more preferred aspect, the polypeptide is a *Magnaporthe grisea* polypeptide, and most preferably a *Magnaporthe grisea* FGSC 8958 (Fungal Genetics Stock Center, Kansas City, Mo.) polypeptide, e.g., the polypeptide of SEQ ID NO: 6, SEQ ID NO: 8, or SEQ ID NO: 10, or the mature polypeptide thereof.

In another more preferred aspect, the polypeptide is an *Aspergillus nidulans* polypeptide, and most preferably an *Aspergillus nidulans* A1000 (Fungal Genetics Stock Center, Kansas City, Mo.) polypeptide, e.g., the polypeptide of SEQ ID NO: 12, SEQ ID NO: 14, or SEQ ID NO: 16, or the mature polypeptide thereof.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques which are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Polynucleotides

The present invention also relates to isolated polynucleotides having a nucleotide sequence which encode a polypeptide of the present invention.

In a preferred aspect, the nucleotide sequence is set forth in SEQ ID NO: 1. In another more preferred aspect, the nucleotide sequence is the sequence contained in plasmid pSMO224 which is contained in *E. coli* NRRL B-30774. In another preferred aspect, the nucleotide sequence is the mature polypeptide coding region of SEQ ID NO: 1. In another preferred aspect, the nucleotide sequence is nucleotides 73 to 1256 of SEQ ID NO: 1. In another more preferred aspect, the nucleotide sequence is the mature polypeptide coding region contained in plasmid pSMO224 which is contained in *E. coli* NRRL B-30774. The present invention also encompasses nucleotide sequences which encode a polypeptide having the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 which encode fragments of SEQ ID NO: 2 that have lipase activity.

In another preferred aspect, the nucleotide sequence is set forth in SEQ ID NO: 3. In another more preferred aspect, the nucleotide sequence is the sequence contained in plasmid pSMO223 which is contained in *E. coli* NRRL B-30773. In another preferred aspect, the nucleotide sequence is the mature polypeptide coding region of SEQ ID NO: 3. In another preferred aspect, the nucleotide sequence is nucleotides 73 to 944 of SEQ ID NO: 3. In another more preferred aspect, the nucleotide sequence is the mature polypeptide coding region contained in plasmid pSMO223 which is contained in *E. coli* NRRL B-30773. The present invention also encompasses nucleotide sequences which encode a polypeptide having the amino acid sequence of SEQ ID NO: 4 or the mature polypeptide thereof, which differ from SEQ ID NO: 3 or the mature polypeptide coding sequence thereof by virtue of the degeneracy of the genetic code. The present invention also relates to subsequences of SEQ ID NO: 3 which encode fragments of SEQ ID NO: 4 that have lipase activity.

In another preferred aspect, the nucleotide sequence is set forth in SEQ ID NO: 5. In another more preferred aspect, the nucleotide sequence is the sequence contained in plasmid pHyGe026 which is contained in *E. coli* NRRL B-30772. In another preferred aspect, the nucleotide sequence is the mature polypeptide coding region of SEQ ID NO: 5. In another preferred aspect, the nucleotide sequence is nucleotides 58 to 1085 of SEQ ID NO: 5. In another more preferred aspect, the nucleotide sequence is the mature polypeptide coding region contained in plasmid pHyGe026 which is contained in *E. coli* NRRL B-30772. The present invention also encompasses nucleotide sequences which encode a polypeptide having the amino acid sequence of SEQ ID NO: 6 or the mature polypeptide thereof, which differ from SEQ ID NO: 5 or the mature polypeptide coding sequence thereof by virtue of the degeneracy of the genetic code. The present invention also relates to subsequences of SEQ ID NO: 5 which encode fragments of SEQ ID NO: 6 that have lipase activity.

In another preferred aspect, the nucleotide sequence is set forth in SEQ ID NO: 7. In another more preferred aspect, the nucleotide sequence is the sequence contained in plasmid pCrAm138 which is contained in *E. coli* NRRL B-30781. In another preferred aspect, the nucleotide sequence is the mature polypeptide coding region of SEQ ID NO: 7. In another preferred aspect, the nucleotide sequence is nucleotides 55 to 1044 of SEQ ID NO: 7. In another more preferred aspect, the nucleotide sequence is the mature polypeptide coding region contained in plasmid pCrAm138 which is contained in *E. coli* NRRL B-30781. The present invention also encompasses nucleotide sequences which encode a polypeptide having the amino acid sequence of SEQ ID NO: 8 or the mature polypeptide thereof, which differ from SEQ ID NO: 7 or the mature polypeptide coding sequence thereof by virtue of the degeneracy of the genetic code. The present invention also relates to subsequences of SEQ ID NO: 7 which encode fragments of SEQ ID NO: 8 that have lipase activity.

In another preferred aspect, the nucleotide sequence is set forth in SEQ ID NO: 9. In another more preferred aspect, the nucleotide sequence is the sequence contained in plasmid pBM135g which is contained in *E. coli* NRRL B-30779. In another preferred aspect, the nucleotide sequence is the mature polypeptide coding region of SEQ ID NO: 9. In another preferred aspect, the nucleotide sequence is nucleotides 73 to 1179 of SEQ ID NO: 9. In another more preferred aspect, the nucleotide sequence is the mature polypeptide coding region contained in plasmid pBM135g which is contained in *E. coli* NRRL B-30779. The present invention also encompasses nucleotide sequences which encode a polypeptide having the amino acid sequence of SEQ ID NO: 10 or the mature polypeptide thereof, which differ from SEQ ID NO: 9 or the mature polypeptide coding sequence thereof by virtue of the degeneracy of the genetic code. The present invention also relates to subsequences of SEQ ID NO: 9 which encode fragments of SEQ ID NO: 10 that have lipase activity.

In another preferred aspect, the nucleotide sequence is set forth in SEQ ID NO: 11. In another more preferred aspect, the nucleotide sequence is the sequence contained in plasmid pJLin171 which is contained in *E. coli* NRRL B-30755. In another preferred aspect, the nucleotide sequence is the mature polypeptide coding region of SEQ ID NO: 11. In another preferred aspect, the nucleotide sequence is nucleotides 58 to 1038 of SEQ ID NO: 11. In another more preferred aspect, the nucleotide sequence is the mature polypeptide coding region contained in plasmid pJLin171 which is contained in *E. coli* NRRL B-30755. In another more preferred aspect, the nucleotide sequence is the mature polypeptide coding region contained in plasmid pJLin171 which is contained in *E. coli* NRRL B-30755. The present invention also encompasses nucleotide sequences which encode a polypeptide having the amino acid sequence of SEQ ID NO: 12 or the mature polypeptide thereof, which differ from SEQ ID NO: 11 or the mature polypeptide coding sequence thereof by virtue of the degeneracy of the genetic code. The present invention also relates to subsequences of SEQ ID NO: 11 which encode fragments of SEQ ID NO: 12 that have lipase activity.

In another preferred aspect, the nucleotide sequence is set forth in SEQ ID NO: 13. In another more preferred aspect, the nucleotide sequence is the sequence contained in plasmid pJLin170 which is contained in *E. coli* NRRL B-30754. In another preferred aspect, the nucleotide sequence is the mature polypeptide coding region of SEQ ID NO: 13. In another preferred aspect, the nucleotide sequence is nucleotides 73 to 1116 of SEQ ID NO: 13. In another more preferred aspect, the nucleotide sequence is the mature polypeptide coding region contained in plasmid pJLin170 which is contained in *E. coli* NRRL B-30754. In another more preferred aspect, the nucleotide sequence is the mature polypeptide coding region contained in plasmid pJLin170 which is contained in *E. coli* NRRL B-30754. The present invention also encompasses nucleotide sequences which encode a polypeptide having the amino acid sequence of SEQ ID NO: 14 or the mature polypeptide thereof, which differ from SEQ ID NO: 13 or the mature polypeptide coding sequence thereof by virtue of the degeneracy of the genetic code. The present invention also relates to subsequences of SEQ ID NO: 13 which encode fragments of SEQ ID NO: 14 that have lipase activity.

In another preferred aspect, the nucleotide sequence is set forth in SEQ ID NO: 15. In another more preferred aspect, the nucleotide sequence is the sequence contained in plasmid pBM141 which is contained in *E. coli* NRRL B-30780. In another preferred aspect, the nucleotide sequence is the mature polypeptide coding region of SEQ ID NO: 15. In another preferred aspect, the nucleotide sequence is nucleotides 76 to 1280 of SEQ ID NO: 15. In another more preferred aspect, the nucleotide sequence is the mature polypeptide coding region contained in plasmid pBM141 which is contained in *E. coli* NRRL B-30780. In another more preferred aspect, the nucleotide sequence is the mature polypeptide coding region contained in plasmid pBM141 which is contained in *E. coli* NRRL B-30780. The present invention also encompasses nucleotide sequences which encode a polypeptide having the amino acid sequence of SEQ ID NO: 16 or the mature polypeptide thereof, which differ from SEQ ID NO: 15 or the mature polypeptide coding sequence thereof by virtue of the degeneracy of the genetic code. The present invention also relates to subsequences of SEQ ID NO: 15 which encode fragments of SEQ ID NO: 16 that have lipase activity.

The present invention also relates to mutant polunucleotides comprising at least one mutation in the mature polypeptide coding sequence of SEQ ID NO: 1, in which the mutant nucleotide sequence encodes the mature polypeptide of SEQ ID NO: 2. In a preferred aspect, the mature polypeptide is amino acids 25 to 396 of SEQ ID NO: 2.

The present invention also relates to mutant polunucleotides comprising at least one mutation in the mature polypeptide coding sequence of SEQ ID NO: 3, in which the mutant nucleotide sequence encodes the mature polypeptide of SEQ ID NO: 4. In a preferred aspect, the mature polypeptide is amino acids 25 to 283 of SEQ ID NO: 4.

The present invention also relates to mutant polynucleotides comprising at least one mutation in the mature polypeptide coding sequence of SEQ ID NO: 5, in which the mutant nucleotide sequence encodes the mature polypeptide of SEQ ID NO: 6. In a preferred aspect, the mature polypeptide is amino acids 20 to 318 of SEQ ID NO: 6.

The present invention also relates to mutant polynucleotides comprising at least one mutation in the mature polypeptide coding sequence of SEQ ID NO: 7, in which the mutant nucleotide sequence encodes the mature polypeptide of SEQ ID NO: 8. In a preferred aspect, the mature polypeptide is amino acids 19 to 348 of SEQ ID NO: 8.

The present invention also relates to mutant polynucleotides comprising at least one mutation in the mature polypeptide coding sequence of SEQ ID NO: 9, in which the mutant nucleotide sequence encodes the mature polypeptide of SEQ ID NO: 10. In a preferred aspect, the mature polypeptide is amino acids 25 to 393 of SEQ ID NO: 10.

The present invention also relates to mutant polynucleotides comprising at least one mutation in the mature polypeptide coding sequence of SEQ ID NO: 11, in which the mutant nucleotide sequence encodes the mature polypeptide of SEQ ID NO: 12. In a preferred aspect, the mature polypeptide is amino acids 20 to 294 of SEQ ID NO: 12.

The present invention also relates to mutant polynucleotides comprising at least one mutation in the mature polypeptide coding sequence of SEQ ID NO: 13, in which the mutant nucleotide sequence encodes the mature polypeptide of SEQ ID NO: 14. In a preferred aspect, the mature polypeptide is amino acids 25 to 308 of SEQ ID NO: 14.

The present invention also relates to mutant polynucleotides comprising at least one mutation in the mature polypeptide coding sequence of SEQ ID NO: 15, in which the mutant nucleotide sequence encodes the mature polypeptide of SEQ ID NO: 16. In a preferred aspect, the mature polypeptide is amino acids 26 to 404 of SEQ ID NO: 16.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Thielavia*, or another or related organism and thus, for example, may be an allelic or species variant of the polypeptide encoding region of the nucleotide sequence.

The present invention also relates to polynucleotides having nucleotide sequences which have a degree of identity to the mature polypeptide coding sequence of SEQ ID NO: 1 of at least 60%, preferably at least 65%, more preferably at least 70%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 73 to 1256 of SEQ ID NO: 1.

The present invention also relates to polynucleotides having nucleotide sequences which have a degree of identity to the mature polypeptide coding sequence of SEQ ID NO: 3 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 73 to 944 of SEQ ID NO: 3.

The present invention also relates to polynucleotides having nucleotide sequences which have a degree of identity to the mature polypeptide coding sequence of SEQ ID NO: 5 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 58 to 1085 of SEQ ID NO: 5.

The present invention also relates to polynucleotides having nucleotide sequences which have a degree of identity to the mature polypeptide coding sequence of SEQ ID NO: 7 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 55 to 1044 of SEQ ID NO: 7.

The present invention also relates to polynucleotides having nucleotide sequences which have a degree of identity to the mature polypeptide coding sequence of SEQ ID NO: 9 of at least 70%, preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 73 to 1179 of SEQ ID NO: 9.

The present invention also relates to polynucleotides having nucleotide sequences which have a degree of identity to the mature polypeptide coding sequence of SEQ ID NO: 11 of at least 70%, preferably at least 75%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 58 to 1038 of SEQ ID NO: 11.

The present invention also relates to polynucleotides having nucleotide sequences which have a degree of identity to the mature polypeptide coding sequence of SEQ ID NO: 13 of at least 70%, preferably at least 75%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 73 to 1116 of SEQ ID NO: 13.

The present invention also relates to polynucleotides having nucleotide sequences which have a degree of identity to the mature polypeptide coding sequence of SEQ ID NO: 15 of at least 70%, preferably at least 75%, more preferably at least 75%, more preferably at least 80%, more preferably at least 85%, more preferably at least 90%, even more preferably at least 95%, and most preferably at least 97% identity, which encode an active polypeptide. In a preferred aspect, the mature polypeptide coding sequence is nucleotides 76 to 1280 of SEQ ID NO: 15.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the polypeptide encoding region of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, e.g., a subsequence thereof, and/or by introduction of nucleotide substitutions which do not give rise to another amino acid sequence of the polypeptide encoded by the nucleotide sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for lipase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated polynucleotides encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, or (iii) a complementary strand of (i) or (ii); or allelic variants and subsequences thereof (Sambrook et al., 1989, supra), as defined herein. In a preferred aspect, the mature polypeptide coding sequence of SEQ ID NO: 1 is nucleotides 73 to 1259. In another preferred aspect, the mature polypeptide coding sequence of SEQ ID NO: 3 is nucleotides 73 to 947. In another preferred aspect, the mature polypeptide coding sequence of SEQ ID NO: 5 is nucleotides 58 to 1088. In another preferred aspect, the mature polypeptide coding sequence of SEQ ID NO: 7 is nucleotides 55 to 1044. In another preferred aspect, the mature polypeptide coding sequence of SEQ ID NO: 9 is nucleotides 73 to 1179. In another preferred aspect, the mature polypeptide coding sequence of SEQ ID NO: 11 is nucleotides 58 to 1041. In another preferred aspect, the mature polypeptide coding sequence of SEQ ID NO: 13 is nucleotides 73 to 1119. In another preferred aspect, the mature polypeptide coding sequence of SEQ ID NO: 15 is nucleotides 76 to 1280.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, (ii) the cDNA sequence contained in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, or (iii) a complementary strand of (i) or (ii); and (b) isolating the hybridizing polynucleotide, which encodes a polypeptide having lipase activity. In a preferred aspect, the mature polypeptide coding sequence of SEQ ID NO: 1 is nucleotides 73 to 1259. In another preferred aspect, the mature polypeptide coding sequence of SEQ ID NO: 3 is nucleotides 73 to 947. In another preferred aspect, the mature polypeptide coding sequence of SEQ ID NO: 5 is nucleotides 58 to 1088. In another preferred aspect, the mature polypeptide coding sequence of SEQ ID NO: 7 is nucleotides 55 to 1044. In another preferred aspect, the mature polypeptide coding sequence of SEQ ID NO: 9 is nucleotides 73 to 1179. In another preferred aspect, the mature polypeptide coding sequence of SEQ ID NO: 11 is nucleotides 58 to 1041. In another preferred aspect, the mature polypeptide coding sequence of SEQ ID NO: 13 is nucleotides 73 to 1119. In another preferred aspect, the mature polypeptide coding sequence of SEQ ID NO: 15 is nucleotides 76 to 1280.

Nucleic Acid Constructs

The present invention also relates to nucleic acid constructs comprising an isolated polynucleotide of the present invention operably linked to one or more control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), Saccharomyces cerevisiae metallothionine (CUP1), and Saccharomyces cerevisiae 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

In a preferred aspect, the signal peptide coding region is nucleotides 1 to 72 of SEQ ID NO: 1 which encode amino acids 1 to 24 of SEQ ID NO: 2.

In another preferred aspect, the signal peptide coding region is nucleotides 1 to 72 of SEQ ID NO: 3 which encode amino acids 1 to 24 of SEQ ID NO: 4.

In another preferred aspect, the signal peptide coding region is nucleotides 1 to 42 of SEQ ID NO: 5 which encode amino acids 1 to 19 of SEQ ID NO: 6.

In another preferred aspect, the signal peptide coding region is nucleotides 1 to 54 of SEQ ID NO: 7 which encode amino acids 1 to 18 of SEQ ID NO: 8.

In another preferred aspect, the signal peptide coding region is nucleotides 1 to 72 of SEQ ID NO: 9 which encode amino acids 1 to 24 of SEQ ID NO: 10.

In another preferred aspect, the signal peptide coding region is nucleotides 1 to 57 of SEQ ID NO: 11 which encode amino acids 1 to 19 of SEQ ID NO: 12.

In another preferred aspect, the signal peptide coding region is nucleotides 1 to 72 of SEQ ID NO: 13 which encode amino acids 1 to 24 of SEQ ID NO: 14.

In another preferred aspect, the signal peptide coding region is nucleotides 1 to 75 of SEQ ID NO: 15 which encode amino acids 1 to 25 of SEQ ID NO: 16.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1. (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*, or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus, Bacillus licheniformis, Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizen, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* Nov. 9, 1980).

In an even more preferred aspect, the yeast host cell is a *Candida, Hansenula, Kluyveromyces, Pichia, Saccharomyces, Schizosaccharomyces*, or *Yarrowia* cell.

In a most preferred aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecllomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. In a preferred aspect, the cell is of the genus *Aspergillus*. In a more preferred aspect, the cell is Aspergillus fumigatus. In another more preferred aspect, the cell is *Aspergillus nidulans*. In another preferred aspect, the cell is of the genus *Magnaporthe*. In another more preferred aspect, the cell is *Magnaporthe grisea*.

The present invention also relates to methods for producing a polypeptide of the present invention, comprising: (a) cultivating a host cell under conditions conducive for production of the polypeptide; and (b) recovering the polypeptide.

The present invention also relates to methods for producing a polypeptide of the present invention, comprising: (a) cultivating a host cell under conditions conducive for production of the polypeptide, wherein the host cell comprises a mutant nucleotide sequence having at least one mutation in the mature polypeptide coding sequence of SEQ ID NO: 1, SEQ ID NO: 3, SEQ ID NO: 5, SEQ ID NO: 7, SEQ ID NO: 9, SEQ ID NO: 11, SEQ ID NO: 13, or SEQ ID NO: 15, wherein the mutant nucleotide sequence encodes a polypeptide which comprises or consists of the mature polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, or SEQ ID NO: 16, and (b) recovering the polypeptide.

In a preferred aspect, the mature polypeptide of SEQ ID NO: 2 is amino acids 25 to 396. In another preferred aspect, the mature polypeptide of SEQ ID NO: 4 is amino acids 25 to 283. In another preferred aspect, the mature polypeptide of SEQ ID NO: 6 is amino acids 20 to 318. In another preferred aspect, the mature polypeptide of SEQ ID NO: 8 is amino acids 19 to 348. In another preferred aspect, the mature polypeptide of SEQ ID NO: 10 is amino acids 25 to 393. In another preferred aspect, the mature polypeptide of SEQ ID NO: 12 is amino acids 20 to 294. In another preferred aspect, the mature polypeptide of SEQ ID NO: 14 is amino acids 25 to 308. In another preferred aspect, the mature polypeptide of SEQ ID NO: 16 is amino acids 26 to 404.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Plants

The present invention also relates to a transgenic plant, plant part, or plant cell which has been transformed with a nucleotide sequence encoding a polypeptide having lipase activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as Festuca, Lolium, temperate grass, such as Agrostis, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems. Specific plant cell compartments, such as chloroplasts, apoplasts, mitochondria, vacuoles, peroxisomes and cytoplasm are also considered to be a plant part. Furthermore, any plant cell, whatever the tissue origin, is considered to be a plant part. Likewise, plant parts such as specific tissues and cells isolated to facilitate the utilisation of the invention are also considered plant parts, e.g., embryos, endosperms, aleurone and seeds coats.

Also included within the scope of the present invention are the progeny of such plants, plant parts, and plant cells.

The transgenic plant or plant cell expressing a polypeptide of the present invention may be constructed in accordance with methods known in the art. In short, the plant or plant cell is constructed by incorporating one or more expression constructs encoding a polypeptide of the present invention into the plant host genome or chloroplast genome and propagating the resulting modified plant or plant cell into a transgenic plant or plant cell.

The expression construct is conveniently a nucleic acid construct which comprises a polynucleotide encoding a polypeptide of the present invention operably linked with appropriate regulatory sequences required for expression of the nucleotide sequence in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the $^{35}$S-CaMV, the maize ubiquitin 1, and the rice actin 1 promoter may be used (Franck et al., 1980, *Cell* 21: 285-294, Christensen et al., 1992, *Plant Mo. Biol.* 18: 675-689; Zhang et al., 1991, *Plant Cell* 3: 1155-1165). Organ-specific promoters may be, for example, a promoter from storage sink tissues such as seeds, potato tubers, and fruits (Edwards & Coruzzi, 1990, *Ann. Rev. Genet.* 24: 275-303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, *Plant and Cell Physiology* 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 85-93), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588). Likewise, the promoter may inducible by abiotic treatments such as temperature, drought, or alterations in salinity or induced by exogenously applied substances that activate the promoter, e.g., ethanol, oestrogens, plant hormones such as ethylene, abscisic acid, and gibberellic acid, and heavy metals.

A promoter enhancer element may also be used to achieve higher expression of a polypeptide of the present invention in the plant. For instance, the promoter enhancer element may be an intron which is placed between the promoter and the nucleotide sequence encoding a polypeptide of the present invention. For instance, Xu et al., 1993, supra, disclose the use of the first intron of the rice actin 1 gene to enhance expression.

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244: 1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 15-38) and can also be used for transforming monocots, although other transformation methods are often used for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275-281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated the expression construct are selected and regenerated into whole plants according to methods well-known in the art. Often the transformation procedure is designed for the selective elimination of selection genes either during regeneration or in the following generations by using, for example, co-transformation with two separate T-DNA constructs or site specific excision of the selection gene by a specific recombinase.

The present invention also relates to methods for producing a polypeptide of the present invention comprising: (a) cultivating a transgenic plant or a plant cell comprising a polynucleotide encoding a polypeptide having lipase activity of the present invention under conditions conducive for production of the polypeptide; and (b) recovering the polypeptide.
Removal or Reduction of Lipase Activity The present invention also relates to methods for producing a mutant of a parent cell, which comprises disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is inactivated. The nucleotide sequence to be modified or inactivated may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification or inactivation of the nucleotide sequence may be accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence which is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell which comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising: (a) cultivating the mutant cell under conditions conducive for production of the polypeptide; and (b) recovering the polypeptide. The term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method for producing a protein product essentially free of lipase activity by fermentation of a cell which produces both a polypeptide of the present invention as well as the protein product of interest by adding an effective amount of an agent capable of inhibiting lipase activity to the fermentation broth before, during, or after the fermentation has been completed, recovering the product of interest from the fermentation broth, and optionally subjecting the recovered product to further purification.

In a further aspect, the present invention relates to a method for producing a protein product essentially free of lipase activity by cultivating the cell under conditions permitting the expression of the product, subjecting the resultant culture broth to a combined pH and temperature treatment so as to reduce the lipase activity substantially, and recovering the product from the culture broth. Alternatively, the combined pH and temperature treatment may be performed on an enzyme preparation recovered from the culture broth. The combined pH and temperature treatment may optionally be used in combination with a treatment with an lipase inhibitor.

In accordance with this aspect of the invention, it is possible to remove at least 60%, preferably at least 75%, more preferably at least 85%, still more preferably at least 95%, and most preferably at least 99% of the lipase activity. Complete removal of lipase activity may be obtained by use of this method.

The combined pH and temperature treatment is preferably carried out at a pH in the range of 2-4 or 9-11 and a temperature in the range of at least 60-70° C. for a sufficient period of time to attain the desired effect, where typically, 30 to 60 minutes is sufficient.

The methods used for cultivation and purification of the product of interest may be performed by methods known in the art.

The methods of the present invention for producing an essentially lipase-free product is of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellulase, chitinase, cutinase, cyclodextrin glycosyltransferase, deoxyribonuclease, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The lipase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from lipase activity which is produced by a method of the present invention.

Compositions

The present invention also relates to compositions comprising a polypeptide of the present invention. Preferably, the compositions are enriched in such a polypeptide. The term "enriched" indicates that the lipase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger*, or *Aspergillus oryzae; Fusarium*, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides*, or *Fusarium venenatum; Humicola*, preferably *Humicola insolens* or *Humicola lanuginosa*; or *Trichoderma*, preferably *Trichoderma harzianum, Trichoderma koningii, Trichoderma longibrachiatum, Trichoderma reesei*, or *Trichoderma viride*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having lipase activity, or compositions thereof.

Use in Degumming. A polypeptide of the present invention may be used for degumming an aqueous carbohydrate solution or slurry to improve its filterability, particularly, a starch hydrolysate, especially a wheat starch hydrolysate which is difficult to filter and yields cloudy filtrates. The treatment may be performed using methods well known in the art. See, for example, EP 219,269, EP 808,903, and U.S. Pat. No. 6,103,505.

Use in Baking. A polypeptide of the present invention may be used in baking according to U.S. Pat. No. 6,558,715.

Use in Detergent. The polypeptides of the present invention may be added to and thus become a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the present invention provides a detergent additive comprising a polypeptide of the present invention as described herein. The detergent additive as well as the detergent composition may comprise one or more enzymes such as a protease, lipase, cutinase, an amylase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Proteases: Suitable proteases include those of animal, vegetable or microbial origin. Microbial origin is preferred. Chemically modified or protein engineered mutants are included. The protease may be a serine protease or a metalloprotease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g., of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258 068 and EP 305 216 or from *H. insolens* as described in WO 96/13580, a *Pseudomonas* lipase, e.g., from *P. alcaligenes* or *P. pseudoalcaligenes* (EP 218 272), *P. cepacia* (EP 331 376),

*P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, *Biochemica et Biophysica Acta*, 1131: 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™, Lipolase Ultra™, and Lipex™ (Novozymes A/S).

Amylases: Suitable amylases ($\alpha$ and/or $\beta$) include those of bacterial or fungal origin. Chemically modified or protein engineered mutants are included. Amylases include, for example, $\alpha$-amylases obtained from *Bacillus*, e.g., a special strain of *Bacillus licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, Fungamyl™ and BAN™ (Novozymes A/S), Rapidase™ and Purastar™ (from Genencor International Inc.).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g., from *C. cinereas*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates, or layered silicates (e.g., SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers, and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, for example, the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

In the detergent compositions, any enzyme may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

In the detergent compositions, a polypeptide of the present invention may be added in an amount corresponding to 0.001-100 mg of protein, preferably 0.005-50 mg of protein, more preferably 0.01-25 mg of protein, even more preferably 0.05-10 mg of protein, most preferably 0.05-5 mg of protein, and even most preferably 0.01-1 mg of protein per liter of wash liquor.

A polypeptide of the present invention may also be incorporated in the detergent formulations disclosed in WO 97/07202, which is hereby incorporated by reference.

Signal Peptide

The present invention also relates to nucleic acid constructs comprising a gene encoding a protein operably linked to a nucleotide sequence comprising or consisting of nucleotides 1 to 72 of SEQ ID NO: 1, nucleotides 1 to 72 of SEQ ID NO: 3, nucleotides 1 to 57 of SEQ ID NO: 5, nucleotides 1 to 54 of SEQ ID NO: 7, nucleotides 1 to 72 of SEQ ID NO: 9, nucleotides 1 to 57 of SEQ ID NO: 11, nucleotides 1 to 72 of SEQ ID NO: 13, or nucleotides 1 to 75 of SEQ ID NO: 15 encoding a signal peptide comprising or consisting of amino acids 1 to 24 of SEQ ID NO: 2, amino acids 1 to 24 of SEQ ID NO: 4, amino acids 1 to 19 of SEQ ID NO: 6, amino acids 1 to 18 of SEQ ID NO: 8, amino acids 1 to 24 of SEQ ID NO: 10, amino acids 1 to 19 of SEQ ID NO: 12, amino acids 1 to 24 of SEQ ID NO: 14, or amino acids 1 to 25 of SEQ ID NO: 16, respectively, wherein the gene is foreign to the nucleotide sequence.

The present invention also relates to recombinant expression vectors and recombinant host cells comprising such nucleic acid constructs.

The present invention also relates to methods for producing a protein comprising (a) cultivating such a recombinant host cell under conditions suitable for production of the protein; and (b) recovering the protein.

The protein may be native or heterologous to a host cell. The term "protein" is not meant herein to refer to a specific length of the encoded product and, therefore, encompasses peptides, oligopeptides, and proteins. The term "protein" also encompasses two or more polypeptides combined to form the encoded product. The proteins also include hybrid polypeptides which comprise a combination of partial or complete polypeptide sequences obtained from at least two different proteins wherein one or more may be heterologous or native to the host cell. Proteins further include naturally occurring allelic and engineered variations of the above mentioned proteins and hybrid proteins.

Preferably, the protein is a hormone or variant thereof, enzyme, receptor or portion thereof, antibody or portion thereof, or reporter. In a more preferred aspect, the protein is an oxidoreductase, transferase, hydrolase, lyase, isomerase, or ligase. In an even more preferred aspect, the protein is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, another lipase, mannosidase, mutanase, oxidase, pectinolytic enzyme, peroxidase, phytase, polyphenoloxidase, proteolytic enzyme, ribonuclease, transglutaminase or xylanase.

The gene may be obtained from any prokaryotic, eukaryotic, or other source.

The present invention is further described by the following examples which should not be construed as limiting the scope of the invention.

EXAMPLES

Materials
Chemicals used as buffers and substrates were commercial products of at least reagent grade.

Strains
*Aspergillus fumigatus* PaHa34, *Magnaporthe grisea* FGSC 8958 (Fungal Genetics Stock Center), and *Aspergillus nidulans* A1000 (Fungal Genetics Stock Center, Kansas City, Mo.) were used as sources for the lipase genes.

Media
Potato dextrose medium was composed per liter of 24 grams of potato dextrose.

YP medium was composed per liter of 10 g of yeast extract and 20 g of Bacto peptone.

SOC medium was composed per liter of 20 g of tryptone, 5 g of yeast extract, 2 ml of 5 M NaCl, and 2.5 ml of 1 M KCl.

NZY$^+$ medium was composed per liter of 10 g of NZ amine, 5 g of yeast extract, 5 g of NaCl, 12.5 mM $MgCl_2$, 12.5 mM $MgSO_4$, and 10 ml of 2 M glucose.

LB medium was composed per liter of 10 g of tryptone, 5 g of yeast extract, and 5 g of NaCl.

MY25 medium was composed per liter of 25 g of maltodextrin, 2 g of $MgSO_4.7H_2O$, 10 g of $KH_2PO_4$, 2 g of citric acid, 2 g of $K_2SO_4$, 2 g of urea, 10 g of yeast extract, and 1.5 ml of AMG trace metals solution, adjusted to pH 6.

AMG trace metals solution was composed per liter of 14.3 g of $ZnSO_4.7H_2O$, 2.5 g of $CuSO_4.5H_2O$, 0.5 g of $NiCl_2.6H_2O$, 13.8 g of $FeSO_4.7H_2O$, 8.5 g of $MnSO_4.H_2O$, and 3 g of citric acid.

CM was composed per liter of 6 g of yeast extract, 6 g of casein acid hydrolysate, and 10 g of sucrose.

COVE selection plates were composed per liter of 342.3 g of sucrose, 20 ml of COVE salt solution, 10 mM acetamide, 15 mM $CsCl_2$, and 25 g of Noble agar.

COVE salt solution was composed per liter of 26 g of KCl, 26 g of $MgSO_4.7H_2O$, 76 g of $KH_2PO_4$, and 50 ml of COVE trace metals solution.

COVE trace metals solution was composed per liter of 0.04 g of $NaB_4O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

2×YT plates were composed per liter of 16 g of tryptone, 10 g of yeast extract, 5 g of NaCl, and 15 g of Bacto agar.

Example 1

Identification of Lipase Genes in the Partial Genomic Sequence of *Aspergillus fumigatus*

A tfasty search (Pearson, W. R., 1999, in *Bioinformatics Methods and Protocols*, S. Misener and S. A. Krawetz, ed., pp. 185-219) of the *Aspergillus fumigatus* partial genome sequence (The Institute for Genomic Research, Rockville, Md.) was carried out using as query a lipase sequence from *Thermomyces lanuginosus* (Accession No. O59952). Several genes were identified as putative lipases based upon an E value of less than 0.001 in the tfasty output. Two genomic regions of approximately 900 bp and 570 bp with greater than 33% identity to the query sequence at the amino acid level were chosen for further study. The gene models for the putative lipase genes were predicted based on homology to the *Thermomyces lanuginosus* lipase as well as conserved sequences present at the 5' and 3' ends of fungal introns.

Example 2

Aspergillus fumigatus genomic DNA Extraction

*Aspergillus fumigatus* was grown in 250 ml of potato dextrose medium in a baffled shake flask at 37° C. and 240 rpm. Mycelia were harvested by filtration, washed twice in TE (10 mM Tris-1 mM EDTA), and frozen under liquid nitrogen. Frozen mycelia were ground, by mortar and pestle, to a fine powder, which was resuspended in pH 8.0 buffer containing 10 mM Tris, 100 mM EDTA, 1% Triton X-100, 0.5 M guanidine-HCl, and 200 mM NaCl. DNase free RNase A was added at a concentration of 20 mg/liter and the lysate was incubated at 37° C. for 30 minutes. Cellular debris was removed by centrifugation, and DNA was isolated using a QIAGEN Maxi 500 column (QIAGEN Inc., Valencia, Calif.). The columns were equilibrated in 10 ml of QBT, washed with 30 ml of QC, and eluted with 15 ml of QF (all buffers from QIAGEN Inc., Valencia, Calif.). DNA was precipitated in isopropanol, washed in 70% ethanol, and recovered by centrifugation. The DNA was resuspended in TE buffer.

Example 3

Cloning of an *Aspergillus fumigatus* Lipase 1 Gene

Two synthetic oligonucleotide primers shown below were designed based on the predicted start and stop codons of the open reading frame to PCR amplify an *Aspergillus fumigatus* lipase 1 gene from the genomic DNA prepared in Example 2.

```
Forward primer:
                                        (SEQ ID NO: 17)
5'-GAGACGCATGCTTCACAAGTATAG-3'

Reverse primer:
                                        (SEQ ID NO: 18)
5'-GTCACCTCTAGTTAATTAATCAGATTATCTTGC-3'
```

Bold letters represent coding sequence.

The fragment of interest was amplified by PCR using the Expand High Fidelity PCR System (Roche Diagnostics, Mannheim, Germany). One µM of each of the primers above were used in a PCR reaction containing 20 ng of *Aspergillus fumigatus* genomic DNA, 1×PCR buffer (Roche Diagnostics, Mannheim, Germany) with 1.5 mM $MgCl_2$, 1 µl of a dATP, dTTP, dGTP, and dCTP mix (10 mM each), and 0.75 µl of DNA polymerase mix (3.5 U/µl; Roche Diagnostics, Mannheim, Germany) in a final volume of 50 µl. To amplify the fragment, an Eppendorf Mastercycler Thermocycler (Hamburg, Germany) was programmed for 1 cycle at 94° C. for 2 minutes; 10 cycles each at 94° C. for 15 seconds, 60° C. for 30 seconds, and 72° C. for 1.25 minutes; 15 cycles each at 94° C. for 15 seconds, 60° C. for 30 seconds, and 72° C. for 1.25 minutes plus a 5 second elongation at each successive cycle; 1 cycle at 72° C. for 7 minutes; and a 10° C. hold.

The reaction product was visualized on a 0.8% agarose gel using 44 mM Tris Base, 44 mM boric acid, 0.5 mM EDTA (TBE) buffer and a 1.3 kb product band was purified using a QIAquick PCR Purification Kit (QIAGEN Inc., Valencia, Calif.) according to the manufacturer's instructions.

The PCR fragment and pCR2.1-TOPO vector (Invitrogen, Carlsbad, Calif.) were ligated using conditions specified by the manufacturer to produce pSMO224 (FIG. 1). Two µl of the reaction was used to transform *E. coli* TOP10 One Shot competent cells (Invitrogen, Carlsbad, Calif.) according to the manufacturer's instructions. A 2 µl volume of the ligation mixture was added to the *E. coli* cells and incubated on ice for 20 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Six colonies that grew on the plates were picked with a sterile toothpick and grown overnight at 37° C., 250 rpm in a 15 ml Falcon tube containing 3 ml of LB medium supplemented with 100 µg of ampicillin per ml. An *E. coli* transformant containing a plasmid designated pSMO224 was detected by restriction digestion and plasmid DNA was prepared using a BioRobot 9600 (QIAGEN Inc., Valencia, Calif.).

*E. coli* TOP10 One Shot cells containing pSMO224 were deposited with the Agricultural Research Service Patent Culture Collection, Northern Regional Research Center, 1815 University Street, Peoria, Ill., 61604, as NRRL B-30774, with a deposit date of Sep. 16, 2004.

Example 4

Characterization of the *Aspergillus fumigatus* Genomic Sequence Encoding Lipase 1

DNA sequencing of the *Aspergillus fumigatus* lipase 1 gene from pSMO224 was performed with an Applied Biosystems Model 377 XL DNA Sequencer (Perkin-Elmer/Applied Biosystems, Inc., Foster City, Calif.) using dye-terminator chemistry (Giesecke et al., 1992, *Journal of Virology Methods* 38: 47-60) and primer walking strategy. Nucleotide sequence data were scrutinized for quality and all sequences were compared to each other with assistance of PHRED/PHRAP software (University of Washington, Seattle, Wash.).

Gene models for the sequence were constructed based on the tfasty output and alignment with a homologous lipase gene from *Thermomyces lanuginosus*. The nucleotide sequence (SEQ ID NO: 1) and deduced amino acid sequence (SEQ ID NO: 2) are shown in FIG. 2. The genomic fragment encodes a polypeptide of 396 amino acids, interrupted by 1 intron of 68 bp. The % G+C content of the gene is 52.6% and the mature protein coding region is 52.9%. Using the SignalP software program (Nielsen et al., 1997, *Protein Engineering* 10:1-6), a signal peptide of 24 residues was predicted. The predicted mature protein contains 373 amino acids with a molecular mass of 41.5 kDa.

A comparative alignment of lipase sequences was made employing the Clustal W method (Higgins, 1989, supra) using LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* lipase 1 gene shares 23% identity to the deduced amino acid sequence of a *Thermomyces lanuginosus* lipase gene (accession number O59952).

Example 5

Construction of pAlLo1 Expression Vector

Expression vector pAlLo1 was constructed by modifying pBANe6 (U.S. Pat. No. 6,461,837), which comprises a hybrid of the promoters from the genes for *Aspergillus niger* neutral alpha-amylase and *Aspergillus oryzae* triose phosphate isomerase (NA2-tpi promoter), *Aspergillus niger* amyloglucosidase terminator sequence (AMG terminator), and *Aspergillus nidulans* acetamidase gene (amdS). Modification of pBANe6 was performed by first eliminating three Nco I restriction sites at positions 2051, 2722, and 3397 bp from the amdS selection marker by site-directed mutagenesis. All changes were designed to be "silent" leaving the actual protein sequence of the amdS gene product unchanged. Removal of these three sites was performed simultaneously with a GeneEditor Site-Directed Mutagenesis Kit (Promega, Madison, Wis.) according to the manufacturer's instructions using the following primers (underlined nucleotide represents the changed base):

```
AMDS3NcoMut (2050):
                                        (SEQ ID NO: 19)
5'-GTGCCCCATGATACGCCTCCGG-3'

AMDS2NcoMut (2721):
                                        (SEQ ID NO: 20)
5'-GAGTCGTATTTCCAAGGCTCCTGACC-3'

AMDS1NcoMut (3396):
                                        (SEQ ID NO: 21)
5'-GGAGGCCATGAAGTGGACCAACGG-3'
```

A plasmid comprising all three expected sequence changes was then submitted to site-directed mutagenesis, using a QuickChange Mutagenesis Kit (Stratagene, La Jolla, Calif.), to eliminate the Nco I restriction site at the end of the AMG terminator at position 1643. The following primers (underlined nucleotide represents the changed base) were used for mutagenesis:

```
Upper Primer to mutagenize the AMG
terminator sequence:
                                        (SEQ ID NO: 22)
5'-CACCGTGAAAGCCATGCTCTTTCCTTCGTGTAGAAGACCAGACAG-3'

Lower Primer to mutagenize the AMG
terminator sequence:
                                        (SEQ ID NO: 23)
5'-CTGGTCTTCTACACGAAGGAAAGAGCATGGCTTTCACGGTGTCTG-3'
```

Figure 3:
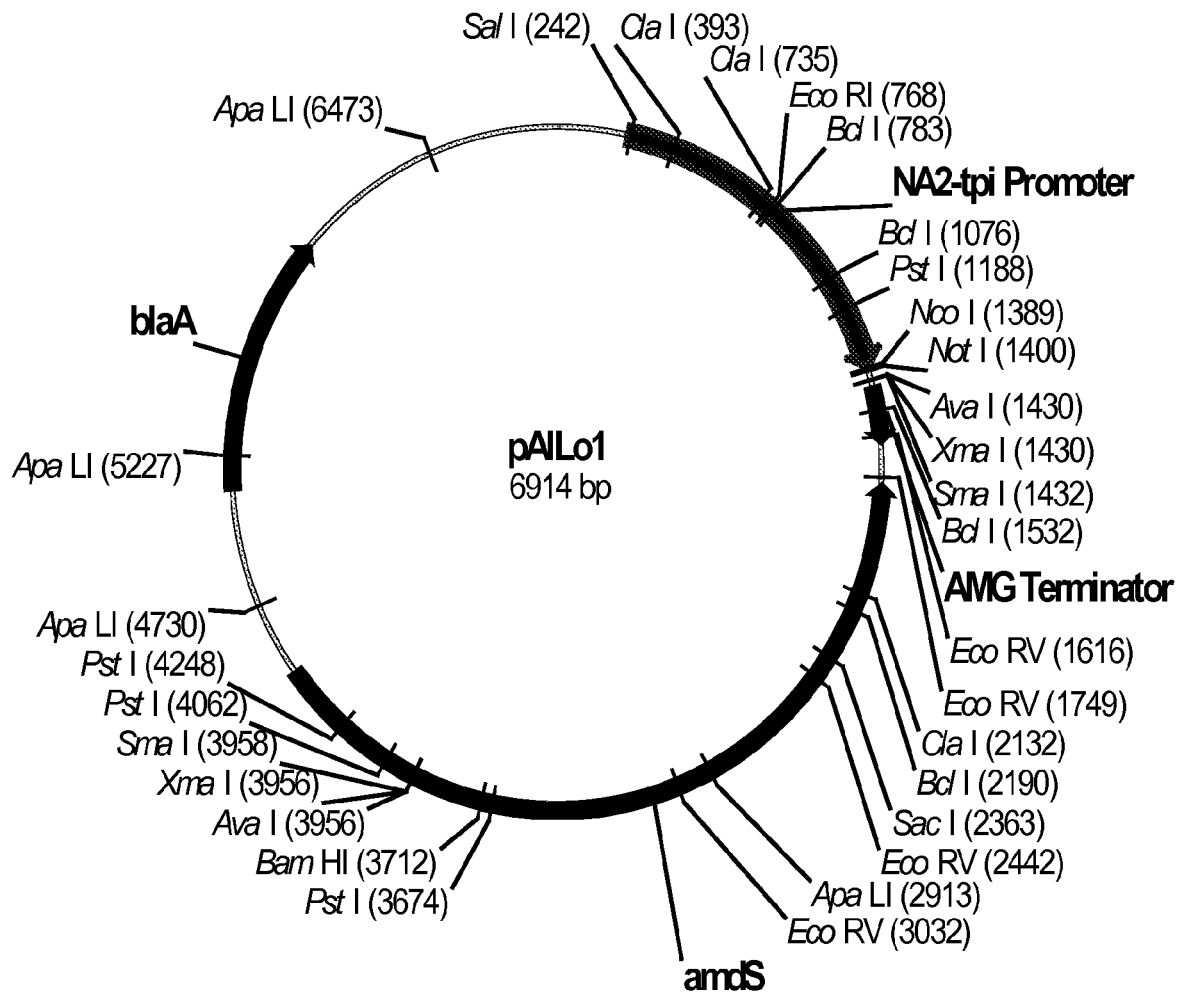
FIG. 3 shows a restriction map of pAlLo1.

The last step in the modification of pBANe6 was the addition of a new Nco I restriction site at the beginning of the polylinker using a QuickChange Mutagenesis Kit and the following primers (underlined nucleotides represent the changed bases) to yield pAlLo1 (FIG. 3).

```
Upper Primer to mutagenize the NA2-tpi promoter:
                                        (SEQ ID NO: 24)
5'-CTATATACACAACTGGATTTACCATGGGCCCGCGGCCGCAGATC-3'

Lower Primer to mutagenize the NA2-tpi promoter:
                                        (SEQ ID NO: 25)
5'-GATCTGCGGCCGCGGGCCCATGGTAAATCCAGTTGTGTATATAG-3'
```

Example 6

Construction of pBM120a Expression Vector

Plasmid pBM120a was constructed to obtain a plasmid containing the double NA2 promoter (NA2-NA2-tpi) for driving gene expression in *Aspergillus* species, and containing the ampicillin resistance gene for selection in *E. coli*.

Primers were designed to PCR amplify the double NA2 promoter from pJaL721 (WO 03/008575). Restriction enzyme sites Sal I and Nco I (underlined) were added for cloning the double promoter into the *Aspergillus* expression plasmid pAlLo1.

```
                                        (SEQ ID NO: 26)
5'-GTCGACATGGTGTTTTGATCATTTTA-3'

(SEQ ID NO: 27)
5'-CCATGGCCAGTTGTGTATATAGAGGA-3'
```

The fragment of interest was amplified by PCR using the Expand High Fidelity PCR System. The PCR amplification reaction mixture contained 1 µl of 0.09 µg of pJaL721 per µl, 1 µl of each of the primers (50 pmol/µl), 5 µl of 10×PCR buffer with 15 mM MgCl$_2$, 1 µl of a dATP, dTTP, dGTP, and dCTP mix (10 mM each), 37.25 µl of water, and 0.75 µl of DNA polymerase mix (3.5 U/µl). To amplify the fragment, an Eppendorf Mastercycler thermocycler was programmed for 1 cycle at 94° C. for 2 minutes; 10 cycles each at 94° C. for 15 seconds, 55° C. for 30 seconds, and 72° C. for 1.25 minutes; 15 cycles each at 94° C. for 15 seconds, 55° C. for 30 seconds, and 72° C. for 1.25 minutes plus a 5 second elongation at each successive cycle; 1 cycle at 72° C. for 7 minutes; and a 10° C. hold. Ten microliters of this PCR reaction was mixed with 1 µl of 10×DNA loading dye (25% glycerol, 10 mM Tris pH 7.0, 10 mM EDTA, 0.025% bromophenol blue, 0.025% xylene cyanol) and run on a 1.0% (w/v) agarose gel using TBE buffer. The 1128 bp PCR product was observed with UV light on a Nucleotech gel visualization system (Nucleotech, San Mateo, Calif.). The PCR product was directly ligated into pPC2.1-TOPO according to the manufacturer's instructions. A 1 µl volume of fresh PCR product, 3 µl of double-distilled water, and 1 µl of the TOPO cloning vector were mixed with a pipette and incubated at room temperature for 5 minutes.

After the incubation, 2 µl of the mixture was used to transform OneShot competent *E. coli* cells. A 2 µl volume of the ligation mixture was added to the *E. coli* cells and incubated on ice for 5 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Eight colonies that grew on the plates were picked with a sterile toothpick and grown overnight at 37° C., 250 rpm in a 15 ml Falcon tube containing 3 ml of LB medium supplemented with 100 µg of ampicillin per ml. The plasmids were isolated using a QIAGEN BioRobot 9600.

Figure 4:
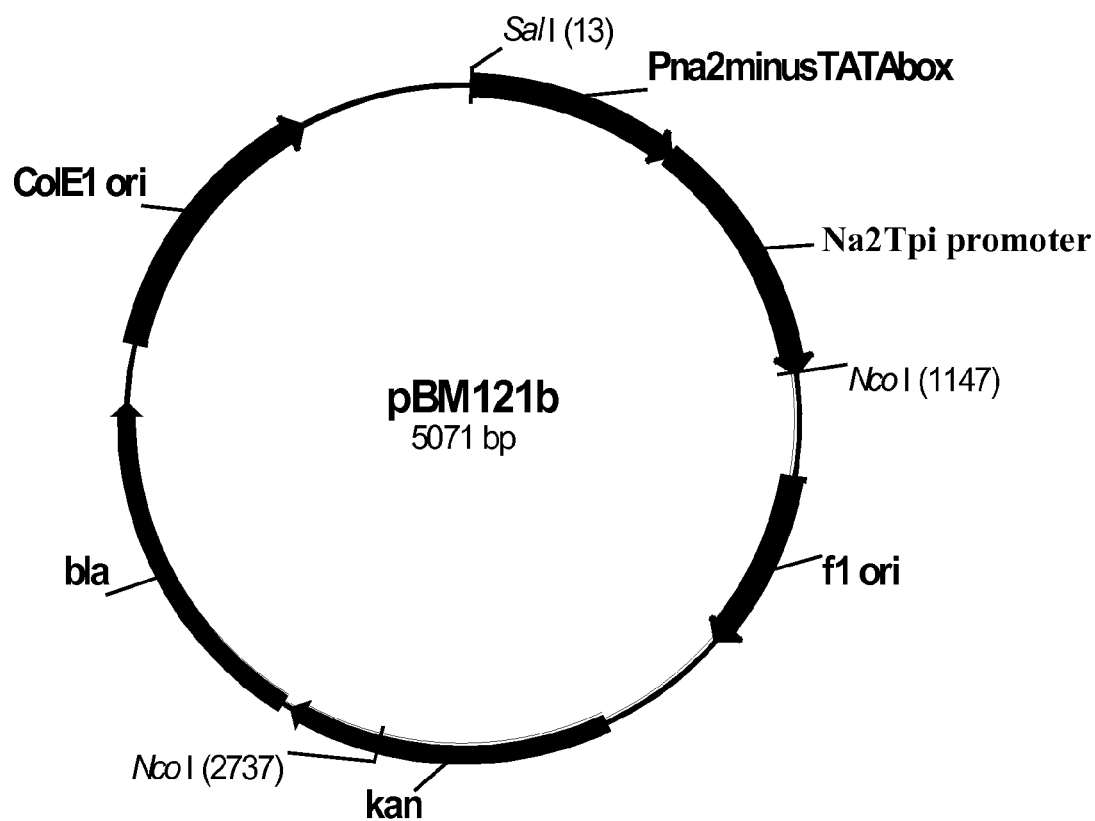
FIG. 4 shows a restriction map of pBM121b.

Four µl volumes of the resulting plasmid minipreps were digested with Eco RI. The digestion reactions were analyzed by agarose gel chromatography and UV analysis as previously described for the PCR reaction. Isolated plasmids containing an insert were sequenced using 1 µl of plasmid template, 1.6 ng of M13 primer (forward or reverse) (MWG Biotech; High Point; NC), and water to 6 µl. DNA sequencing was performed with an Applied Biosystems Model 377 Sequencer XL (Applied Biosystems, Inc., Foster City, Calif.) using dye-terminator chemistry. The resulting plasmid was designated pBM121b (FIG. 4).

Figure 5:
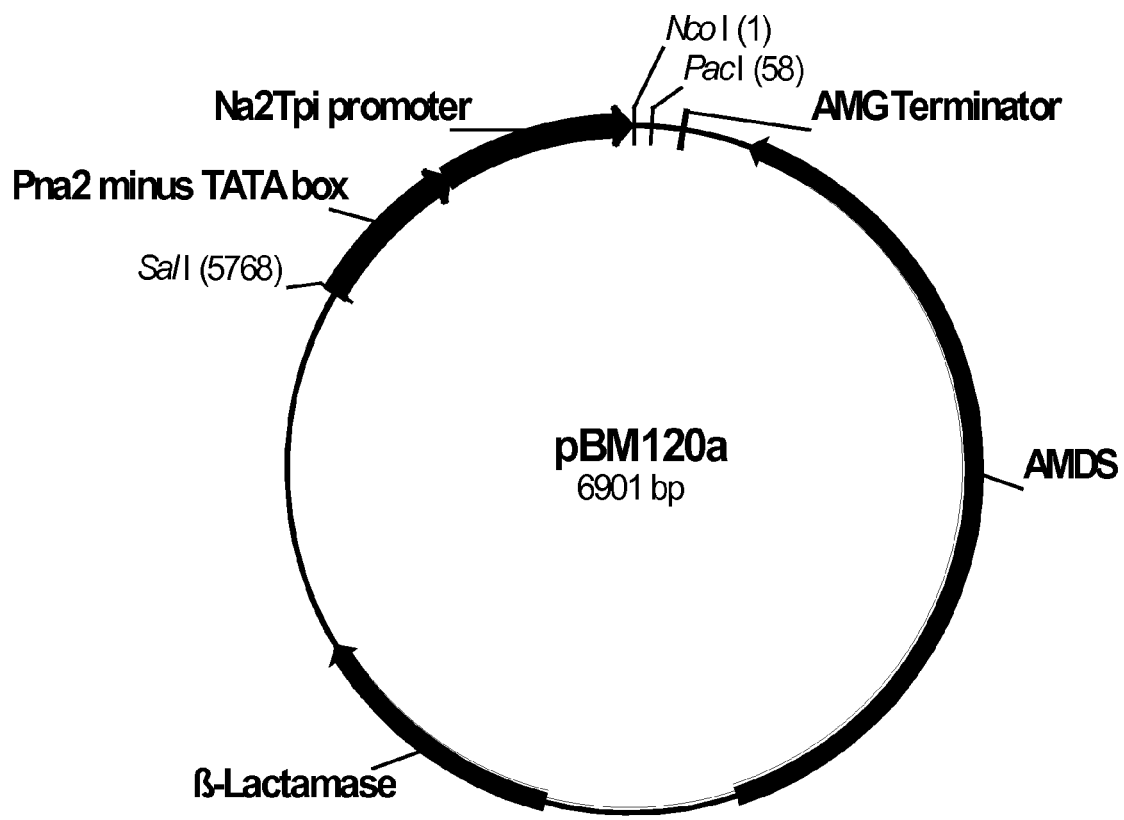

A 5 µl volume of pBM121b was digested with Sal I and Nco I. The digestion reactions were analyzed by agarose gel electrophoresis as described above, and ligated to the vector pAlLo1, which had been previously digested with Sal I and Nco I. The resulting expression plasmid was designated pBM120a (FIG. 5).

Example 7

Construction of an *Aspergillus oryzae* Expression Vector Expressing *Aspergillus fumigatus* Lipase 1 Gene Two synthetic oligonucleotide primers shown below were designed to PCR amplify the *Aspergillus fumigatus* lipase 1 gene from the genomic DNA prepared in Example 2.

```
Forward primer:
                                       (SEQ ID NO: 28)
5'-TACACAACTGGCCATGCTTCACAAGTATAG-3'

Reverse primer:
                                       (SEQ ID NO: 29)
5'-GTCACCTCTAGTTAATTAATCAGATTATCTTGC-3'
```

Bold letters represent coding sequence. The remaining sequence is homologous to the insertion sites of pBM120a.

The fragment of interest was amplified by PCR using the Expand High Fidelity PCR System. One µM of each of the primers above were used in a PCR reaction containing 20 ng of *Aspergillus fumigatus* genomic DNA, 1×PCR buffer (Roche Diagnostics, Mannheim, Germany) with 1.5 mM MgCl$_2$, 1 µl of a dATP, dTTP, dGTP, and dCTP mix (10 mM each), and 0.75 µl of DNA polymerase mix (3.5 U/µl; Roche Diagnostics, Mannheim, Germany) in a final volume of 50 µl. To amplify the fragment, an Eppendorf Mastercycler thermocycler was programmed for 1 cycle at 94° C. for 2 minutes; 10 cycles each at 94° C. for 15 seconds, 60° C. for 30 seconds, and 72° C. for 1.25 minutes; 15 cycles each at 94° C. for 15 seconds, 60° C. for 30 seconds, and 72° C. for 1.25 minutes plus a 5 second elongation at each successive cycle; 1 cycle at 72° C. for 7 minutes; and a 10° C. hold.

The reaction product was visualized on a 0.8% agarose gel using TBE buffer and a 1.3 kb product band was purified using a QIAquick PCR Purification Kit according to the manufacturer's instructions.

Figure 6:
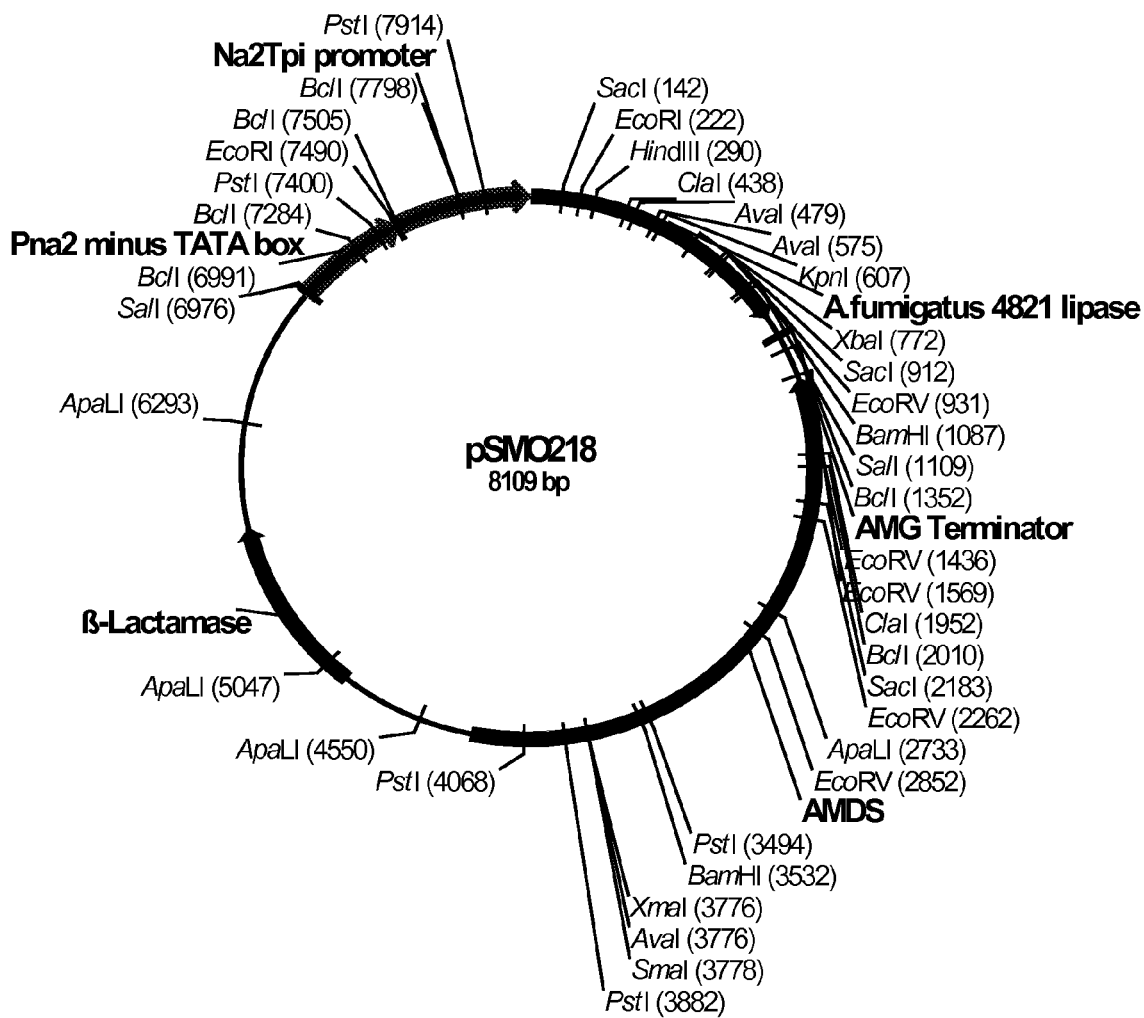
FIG. 6 shows a restriction map of pSMO218.

The 1.3 kb PCR fragment containing the *Aspergillus fumigatus* lipase 1 gene was cloned into pBM120a using an InFusion Cloning Kit (BD Biosciences, Palo Alto, Calif.) where the vector was digested with Nco I and Pac I. The digested vector was purified by gel electrophoresis using a 0.7% agarose gel with TBE buffer, and the PCR fragment was extracted using a QIAquick Gel Extraction Kit (QIAGEN Inc., Valencia, Calif.) and purified using a QIAquick PCR Purification Kit. The gene fragment and the digested vector were ligated together in a reaction resulting in the expression plasmid pSMO218 (FIG. 6). The ligation reaction (50 µl) was composed of 1× InFusion Buffer (BD Biosciences, Palo Alto, Calif.), 1×BSA (BD Biosciences, Palo Alto, Calif.), 1 µl of Infusion enzyme (diluted 1:10) (BD Biosciences, Palo Alto, Calif.), 100 ng of pBM120a digested with Nco I and Pac I, and 50 ng of the *Aspergillus fumigatus* lipase 1 gene purified PCR product. The reaction was incubated at room temperature for 30 minutes. Two µl of the reaction was used to transform *E. coli* SoloPack® Gold supercompetent cells (Stratagene, La Jolla, Calif.) according to the manufacturer's instructions. One µl of β-mercaptoethanol was added to the competent cells, and incubated on ice for 10 minutes. A 2 µl volume of the ligation mixture was then added to the *E. coli* cells and incubated on ice for 30 minutes. Subsequently, the cells were heat shocked for 60 seconds at 54° C., and then placed on ice for 2 minutes. A 150 µl volume of NZY$^+$ medium at 42° C. was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Six colonies that grew on the plates were picked with a sterile toothpick and grown overnight at 37° C., 250 rpm in a 15 ml Falcon tube containing 3 ml of LB medium supplemented with 100 µg of ampicillin per ml. An *E. coli* transformant containing the pSMO218 plasmid was detected by restriction digestion and plasmid DNA was prepared using a QIAGEN BioRobot 9600.

Example 8

Expression of the *Aspergillus fumigatus* Lipase 1 Gene in *Aspergillus oryzae* BECh2

*Aspergillus oryzae* BECh2 (Δalp, Δamy, CPA-, KA-, Δnp1) protoplasts were prepared according to the method of Christensen et al., 1988, *Bio/Technology* 6: 1419-1422. Five µg of pSMO218 was used to transform *Aspergillus oryzae* BECh2.

The transformation of *Aspergillus oryzae* BECh2 with pSMO218 yielded 25 transformants. The transformants were isolated to individual Cove plates. Confluent Cove plates of 25 transformants were washed with 4 ml of 0.01% Tween 20. Two hundred µl of spore suspension was inoculated separately into 25 ml of MY25 medium in 125 ml plastic shake flasks and incubated at 34° C., 250 rpm. Three and five days after incubation, culture supernatants were removed for lipase assay and SDS-PAGE analysis.

Lipase activity was determined as follows: 200 µl of substrate (20 ml of 100 mM MOPS pH 7.5, 4.95 ml DMSO, and 50 µl of p-nitrophenyl butyrate) was added to 20 µl of diluted enzyme sample. The samples were diluted accordingly in 100 mM MOPS pH 7.5, 4 mM CaCl$_2$, and 0.01% Triton X-100. The absorbance at 405 nm was obtained after 15 minutes of incubation at room temperature (25° C.) in a 96-well microtiter plate using a SpectraMAX 250 microplate reader (Molecular Devices Corp., Sunnyvale, Calif.). LIPOLASE™ (*Thermomyces lanuginosus* lipase; Novozymes A/S, Bagsværd, Denmark)) can be used for generating a standard curve to determine lipase units (LUs).

The lipase assay results indicated that at 3 days several of the transformants produced lipase activity above that of the untransformed control. SDS-PAGE analysis (BioRad Criterion 10-20% SDS-PAGE) of 10 µl of the supernatants showed a band at approximately 41 kDa.

Example 9

Determination of Substrate Specificity of Recombinant *Aspergillus fumigatus* Lipase 1

The substrate specificity of *Aspergillus fumigatus* lipase 1 was determined using a panel screen composed of 4-nitrophenol (PNP) lipase substrates.

A panel screen composed of a set of 12 assays utilizing various 4-nitrophenol (PNP) lipase substrates was prepared as described in the Table 1.

TABLE 1

| Panel screen of PNP substrates and buffer conditions | | | | | | | |
|---|---|---|---|---|---|---|---|
| 1 mM PNP-tagged substrate | Shorthand designation | 50 mM MOPS pH 7.0 | 50 mM CHES pH 9.5 | 50 mM MOPS pH 7.5 | 10 mM CaCl$_2$ | Triton X-100 | PNP Conversion Factors |
| 1 Palmitate | 16:0 | x | | | x | 1.2% | 4.466 |
| 2 Palmitate | 16:0 | | x | | x | 1.2% | 1.1 |

TABLE 1-continued

Panel screen of PNP substrates and buffer conditions

| 1 mM PNP-tagged substrate | Shorthand designation | 50 mM MOPS pH 7.0 | 50 mM CHES pH 9.5 | 50 mM MOPS pH 7.5 | 10 mM CaCl$_2$ | Triton X-100 | PNP Conversion Factors |
|---|---|---|---|---|---|---|---|
| 3 Palmitate | 16:0 | | | x | x | 1.2% | 2.037 |
| 4 Palmitate | 16:0 | | x | | x | 0.2% | 1.0 |
| 5 Palmitate | 16:0 | | | x | x | 0.2% | 1.495 |
| 6 Decanoate | 10:0 | x | | | x | 1.2% | 4.466 |
| 7 Decanoate | 10:0 | | x | | x | 1.2% | 1.1 |
| 8 Decanoate | 10:0 | | | x | x | 1.2% | 2.037 |
| 9 Decanoate | 10:0 | | x | | x | 0.2% | 1.0 |
| 10 Valerate | 5:0 | | | x | x | 0.40% | 1.630 |
| 11 Valerate | 5:0 | | | x | x | 0% | 1.370 |
| 12 Butyrate | 4:0 | | | x | x | 0.40% | 1.630 |

These assays were run in 384-well plates using 8 different dilutions of each sample (7 µl) to be evaluated and 80 µl of the substrates. The assays were incubated for up to 24 hours at ambient temperature. Assays were read at 405 nm at time points of approximately 1, 2, 3, 5, and 24 hours. The results were calculated as OD/hour for each individual assay. In order to make an accurate evaluation of the amount of PNP released, it was necessary to mathematically normalize raw OD values by using a conversion factor. The conversion factors were values, determined experimentally, that were necessary to compensate for the fact that PNP has lower OD readings at low pH and in the presences of detergent (Triton X100) than at pH 9.5. The factor normalizes the data to the OD reading that would have been obtained were it possible to quench the reactions to yield maximal OD for each condition while also stopping the reaction at that time point; i.e., PNP-fatty acid substrates are not stable at high pH, the tag comes off without lipase present at high pH, and the tagged substrate is particularly unstable above pH 9 and for shorter chain length fatty acid substrates.

In Table 1 the top two rows (1 and 2) were the assays used for the pH ratio (9.5/7.0). Rows 3 and 10 were used for the "long chain (Slu)/short chain (Lu); comparisons.

The results for the panel screen are shown in Table 2.

TABLE 2

Ratio of PNP-substrates according to Table 1, Example 9, where: P = Palmitate, D = Decanoate, V = Valerate and B = Butyrate

| Long chain/Short chain at pH 7.5 | | | | |
|---|---|---|---|---|
| | P/V | D/V | P/B | D/B |
| ALF004 | 1.888 | 0.887 | 2.556 | 1.201 |
| LIPOLASE ™ | 1.213 | 2.398 | 2.220 | 4.387 |

| pH Ratios; (−) = 0.2% Triton data | | | |
|---|---|---|---|
| | 9.5P/7.0P | 9.5D/7.0D | 9.5P-/7.5P- |
| ALF004 | 0.045 | No Data | Not Tested |
| LIPOLASE ™ | 1.527 | 1.881 | 1.452 |

| No or Low Triton (−) compared to maximum Triton (+) | | | |
|---|---|---|---|
| | V7.5 −/+ | D9.5 +/− | P7.5 +/− | P9.5 +/− |
| ALF004 | Not Tested | Not Tested | Not Tested | Not Tested |
| LIPOLASE ™ | 8.651 | 6.378 | 9.206 | 9.502 |

No Data = not enough activity to give sufficient signal in one of the assays in this test
ALF004 (*Aspergillus oryzae* BeCH2 expressing *Aspergillus fumigatus* lipase 1) test data consists of the average of up to 2 independent screening assay events; LIPOLASE ™ test data consists of the average of up to 17 independent screening assay events.

In comparing the panel screen results of the *Thermomyces lanuginosus* lipase (LIPOLASE™) and the ALF004 the following observations were made:

1. The ratio of activities on PNP-palmitate at pH 9.5 versus pH 7 is 40-fold lower for ALF004 versus LIPOLASE™ suggesting that the *Aspergillus fumigatus* lipase 1 has much lower activity at pH 9.5 versus Lipolase™ or it has a much higher activity at pH 7.0 than LIPOLASE™ or a combination of these two.

2. The ratios of P/V, D/V, and D/B are also quite different for ALF004 versus LIPOLASE™ suggesting there is some acyl change length specificity differences between the two lipases.

Example 10

Cloning of an *Aspergillus fumigatus* Lipase 2 Gene

Two synthetic oligonucleotide primers shown below were designed based on the predicted start and stop codons of the open reading frame to PCR amplify an *Aspergillus fumigatus* lipase 2 gene from the genomic DNA prepared in Example 2.

```
Forward primer:
                                    (SEQ ID NO: 30)
5'-GAGACACATGTTTCACCCAG-3'
Reverse primer:
                                    (SEQ ID NO: 31)
5'-GTCACCTCTAGTTAATTAATCAGTTAGTTGAGC-3'
```

Bold letters represent coding sequence.

Figure 7:
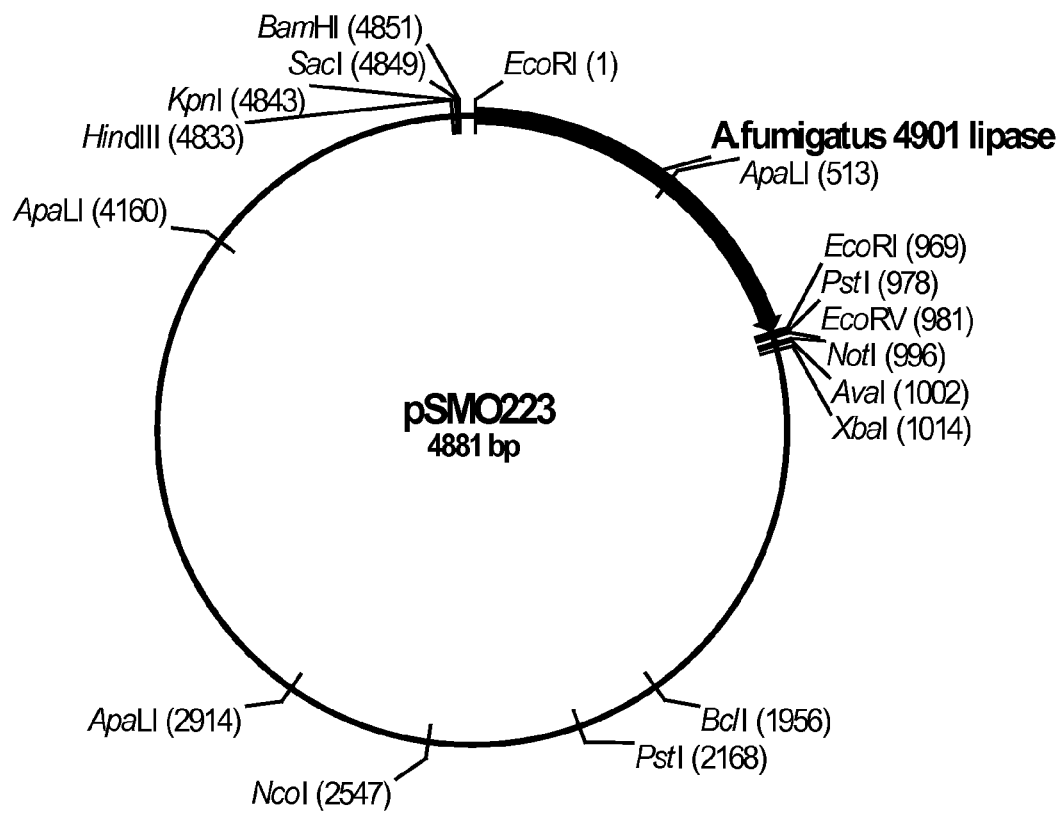
FIG. 7 shows a restriction map of pSMO223.

The fragment was amplified by PCR using the Expand High Fidelity PCR System as described in Example 3. The reaction product was visualized on a 0.7% agarose gel using TBE buffer and a 1.2 kb product band was purified using a QIAquick PCR Purification Kit according to the manufacturer's instructions. The PCR product was then cloned into pCR2.1-TOPO according to manufacturer's instructions to produce pSMO223 (FIG. 7). Two µl of the reaction was used to transform *E. coli* TOP10 One Shot competent cells according to the manufacturer's instructions. A 2 µl volume of the ligation mixture was added to the *E. coli* cells and incubated on ice for 20 minutes. Subsequently, the cells were heat shocked for 30 seconds at 42° C., and then placed on ice for 2 minutes. A 250 µl volume of SOC medium was added to the cells and the mixture was incubated for 1 hour at 37° C. and 250 rpm. After the incubation the colonies were spread on 2×YT plates supplemented with 100 µg of ampicillin per ml and incubated at 37° C. overnight for selection of the plasmid. Six colonies that grew on the plates were picked with a sterile toothpick and grown overnight at 37° C., 250 rpm in a 15 ml Falcon tube containing 3 ml of LB medium supplemented with 100 µg of ampicillin per ml. An *E. coli* transformant containing pSMO223 was detected by restriction digestion and plasmid DNA was prepared using a QIAGEN BioRobot 9600.

*E. coli* TOP10 One Shot cells containing pSMO223 were deposited with the Agricultural Research Service Patent Culture Collection, Northern Regional Research Center, 1815 University Street, Peoria, Ill., 61604, as NRRL B-30773, with a deposit date of Sep. 16, 2004.

Example 11

Characterization of the *Aspergillus fumigatus* Genomic Sequence Encoding Lipase 2

DNA sequencing of the *Aspergillus fumigatus* lipase 2 gene from pSMO223 was performed with an Applied Biosystems Model 377 XL DNA Sequencer using dye-terminator chemistry (Giesecke et al., 1992, supra) and primer walking strategy. Nucleotide sequence data were scrutinized for quality and sequences were compared to each other with assistance of PHRED/PHRAP software (University of Washington, Seattle, Wash.).

Gene models for the sequence were constructed based on the tfasty output and alignment with a homologous lipase gene from *Thermomyces lanuginosus*. The nucleotide sequence (SEQ ID NO: 3) and deduced amino acid sequence (SEQ ID NO: 4) are shown in FIG. 8. The genomic fragment encodes a polypeptide of 283 amino acids, interrupted by 2 introns of 45 and 50 bp. The % G+C content of the gene is 47.1% and the mature protein coding region is 47.2%. Using the SignalP software program (Nielsen et al., 1997, supra), a signal peptide of 24 residues was predicted. The predicted mature protein contains 259 amino acids with a molecular mass of 28.9 kDa.

A comparative alignment of lipase sequences was made employing the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus fumigatus* lipase 2 gene shares 35% identity to the deduced amino acid sequence of a *Thermomyces lanuginosus* lipase gene (accession number O59952).

Example 12

Identification of Lipase Genes in the Partial Genomic Sequence of *Magnaporthe grisea*

A tfasty search (Pearson, W. R., 1999, supra) of the *Magnaporthe grisea* partial genome sequence (Broad Institute MIT, Boston, Mass.) was carried out using as query a lipase sequence from *Thermomyces lanuginosus* (Accession No. O59952). Several genes were identified as putative lipases based upon an E value of less than 0.001 in the tfasty output. Three genomic regions of approximately 930 bp, 750 bp, and 720 bp with greater than 30% identity to the query sequence at the amino acid level were chosen for further study. Gene models for the putative lipase genes were predicted based on homology to the *Thermomyces lanuginosus* lipase as well as conserved sequences present at the 5' and 3' ends of fungal introns.

Example 13

*Magnaporthe grisea* Genomic DNA Extraction

Four hundred µl of *Magnaporthe grisea* (FGSC 8958, Fungal Genetics Stock Center) spores were grown in 50 ml of CM medium in a baffled shake flask at 25° C. and 250 rpm for 4 days. Genomic DNA was then extracted from the mycelia using a DNeasy Plant Mini Kit (QIAGEN, Valencia, Calif.) according to manufacturer's instructions.

Example 14

Cloning of *Magnaporthe grisea* Lipase 1 Gene

Two synthetic oligonucleotide primers shown below were designed based on the genomic sequence outside of the predicted start and stop codons of the open reading frame to PCR amplify a *Magnaporthe grisea* lipase 1 gene from the genomic DNA prepared in Example 13.

```
Forward primer:
                                    (SEQ ID NO: 32)
5'-CCTTGCCCACGCCTTTGGTTC-3'

Reverse primer:
                                    (SEQ ID NO: 33)
5'-CTCATAGCAGCAGGCGAAGCC-3'
```

Both primers represent sequence outside of coding sequence.

Fifty picomoles of each of the primers above were used in a PCR reaction containing 300 ng of *Magnaporthe grisea* genomic DNA, 1× Herculase reaction buffer (Stratagene, La Jolla, Calif.), 1 µl of a dATP, dTTP, dGTP, and dCTP mix (10 mM each), and 2.5 units of Herculase Hotstart DNA polymerase (Stratagene, La Jolla, Calif.) in a final volume of 50 µl. The amplification was conducted in an Eppendorf Mastercycler thermocycler programmed for one cycle at 98° C. for 2 minutes; 10 cycles each at 98° C. for 15 seconds, 62° C. for 30 seconds, and 72° C. for 1 minute and 20 seconds; 15 cycles each at 98° C. for 15 seconds, 62° C. for 30 seconds, and 72° C. for 1 minutes and 20 seconds plus a 5 second elongation at each successive cycle; and 1 cycle at 72° C. for 7 minutes. The heat block then went to a 10° C. soak cycle.

The reaction products were run on a 1.0% agarose gel using 40 mM Tris base-20 mM sodium acetate-1 mM disodium EDTA (TAE) buffer where a 1.2 kb product band was detected. PCR products were purified using a QIAquick PCR Purification Kit according to the manufacturer's instructions.

Two synthetic oligonucleotide primers shown below were designed to PCR amplify a *Magnaporthe grisea* gene encoding a lipase 1 gene from the PCR product described above.

```
Forward primer:
                                    (SEQ ID NO: 34)
5'-ACACAACTGGCCATGAAGGTCTCGTTCGTGTCATCG-3'

Reverse primer:
                                    (SEQ ID NO: 35)
5'-AGTCACCTCTAGTTATCAGTAGCAAGCGCTAATGG-3'
```

Bold letters represent coding sequence. The remaining sequence is homologous to insertion sites of pBM120a.

Fifty picomoles of each of the primers above were used in a PCR reaction containing 2 μl of the 1.2 kb PCR product described above, 1× Herculase reaction buffer, 1 μl of a dATP, dTTP, dGTP, and dCTP mix (10 mM each), 2.5 units of Herculase Hotstart DNA polymerase in a final volume of 50 μl. The amplification was conducted in an Eppendorf Mastercycler thermocycler programmed for 1 cycle at 98° C. for 2 minutes; 10 cycles each at 98° C. for 15 seconds, 62° C. for 30 seconds, and 72° C. for 1 minute and 20 seconds; 15 cycles each at 98° C. for 15 seconds, 62° C. for 30 seconds, and 72° C. for 1 minutes and 20 seconds plus a 5 second elongation at each successive cycle; and 1 cycle at 72° C. for 7 minutes. The heat block then went to a 10° C. soak cycle.

The reaction products were run on a 1.0% agarose gel using TAE buffer where a 1.1 kb product band was detected. The 1.1 kb PCR product was purified using a QIAquick PCR Purification Kit according to the manufacturer's instructions.

Figure 9:
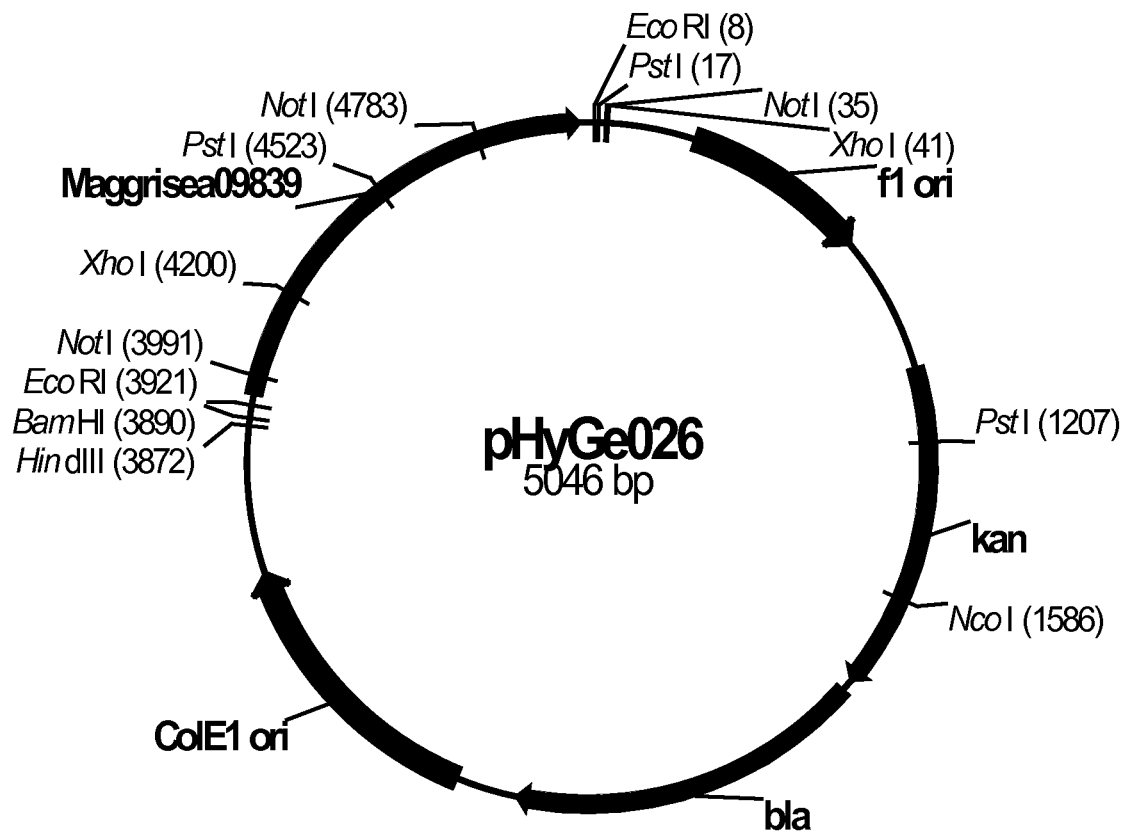
FIG. 9 shows a restriction map of pHyGe026.
Figure 11:
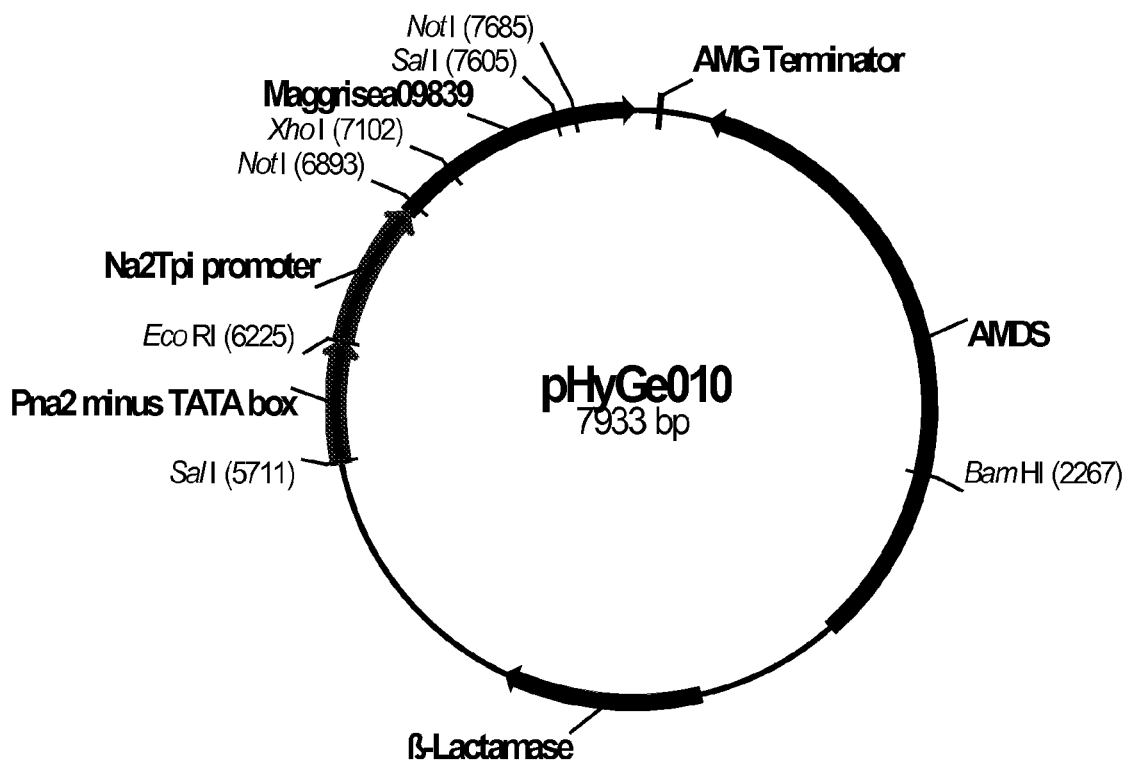
FIG. 11 shows a restriction map of pHyGe010.
Figure 12:
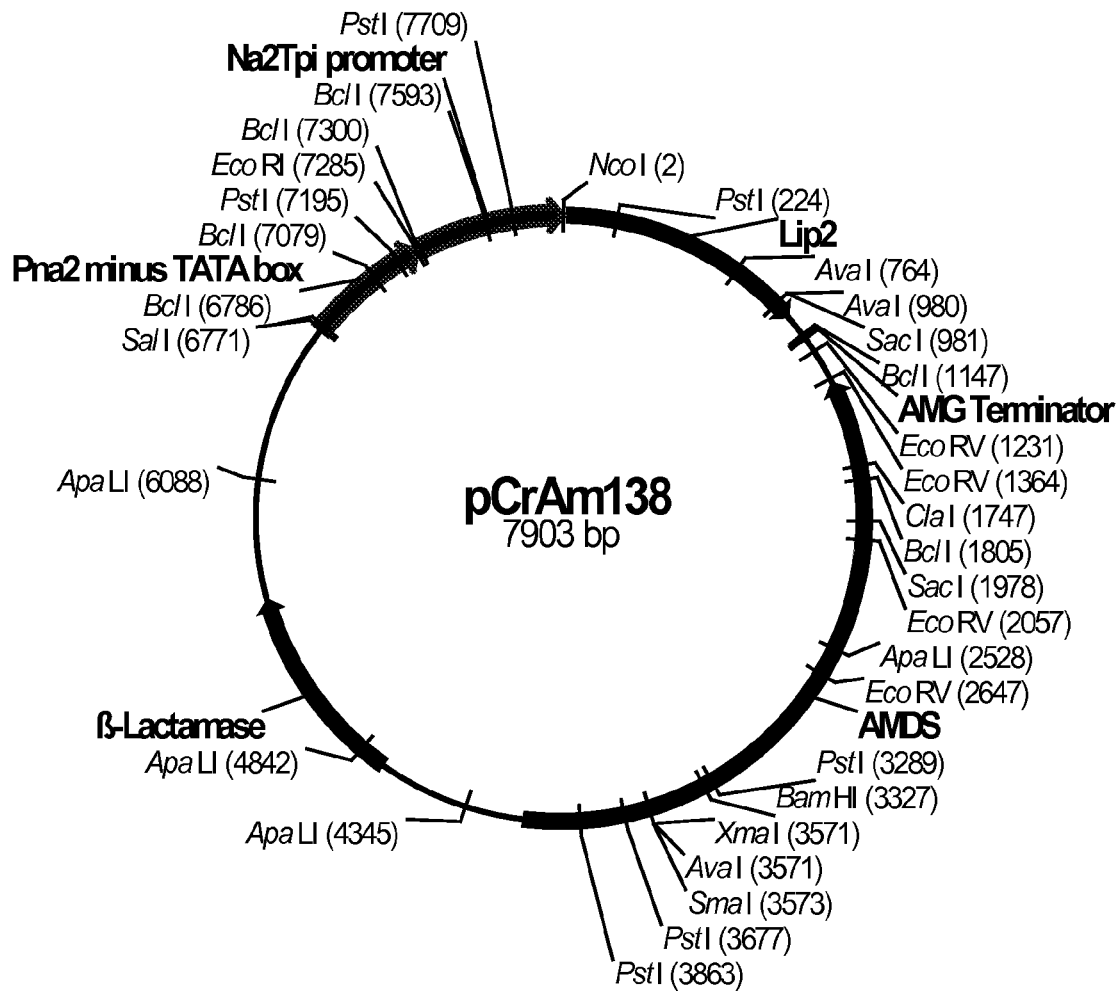
FIG. 12 shows a restriction map of pCrAm138.

The 1.1 kb fragment was cloned into the pCR2.1-TOPO vector. The gene fragment was purified using a QIAquick PCR Purification Kit according to the manufacturer's instructions. The fragment and pCR2.1-TOPO vector were ligated by using conditions specified by the manufacturer resulting in plasmid pHyGe026 (FIG. 9). Two μl of the reaction was used to transform *E. coli* One Shot competent cell. An *E. coli* transformant containing the plasmid pHyGe026 was detected by restriction digestion and plasmid DNA was prepared using a BioRobot 9600.

*E. coli* TOP10 One Shot cells containing pHyGe026 were deposited with the Agricultural Research Service Patent Culture Collection, Northern Regional Research Center, 1815 University Street, Peoria, Ill., 61604, as NRRL B-30772, with a deposit date of Sep. 13, 2004.

Example 15

Characterization of the *Magnaporthe grisea* Genomic Sequence Encoding a Lipase 1 Gene DNA sequencing of the *Magnoporthe grisea* lipase 1 gene from pHyGe026 was performed with an Applied Biosystems Model 377 XL DNA Sequencer using dye-terminator chemistry (Giesecke et al., 1992, supra) and primer walking strategy. Nucleotide sequence data were scrutinized for quality and sequences were compared to each other with assistance of PHRED/PHRAP software (University of Washington, Seattle, Wash.).

Gene models for the lipase gene were predicted based on homology to a *Thermomyces lanuginosa* lipase (Accession No. O59952) as well as conserved sequences present at the 5' and 3' ends of fungal introns. The nucleotide sequence (SEQ ID NO: 5) and deduced amino acid sequence (SEQ ID NO: 6) are shown in FIGS. 10A and 10B. The genomic fragment encodes a polypeptide of 318 amino acids, interrupted by 2 introns of 54 and 77 bp. The % G+C content of the gene is 60.9% and the mature polypeptide coding sequence (nucleotides 58 to 1088 of SEQ ID NO: 6) is 60.5%. Using the SignalP software program (Nielsen et al., 1997, supra), a signal peptide of 19 residues was predicted. The predicted mature protein contains 299 amino acids with a molecular mass of 34 kDa.

A comparative alignment of lipase sequences was determined using the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Magnaporthe* lipase 1 gene shares 31.3% identity to the deduced amino acid sequence of a *Thermomyces lanuginosus* lipase gene (Accession No. O59952).

Example 16

Construction of an *Aspergillus oryzae* Expression Vector for the *Magnaporthe grisea* Lipase 1 Gene The PCR fragment containing the *Magnaporthe grisea* lipase 1 gene was cloned into pBM120a using an InFusion Cloning Kit. The vector was digested with Nco I and Pac I. The digested vector was purified by gel electrophoresis and extracted using a QIAquick Gel Extraction Kit. The gene fragment and digested vector were ligated together in a reaction resulting in the expression plasmid pHyGe010 (FIG. 11) in which transcription of the lipase gene was under the control of the tandem NA2-tpi promoter. The ligation reaction (20 μl) was composed of 1× InFusion Buffer, 1×BSA, 1 μl of Infusion enzyme (diluted 1:10), 50 ng of pBM120a digested with Nco I and Pac I, and 30 ng of the *Magnaporthe grisea* lipase purified PCR product. The reaction was incubated at room temperature for 30 minutes. Two μl of the reaction was used to transform *E. coli* SoloPack® Gold supercompetent cells according to manufacturer's instructions. An *E. coli* transformant containing pHyGe010 was detected by estriction digestion and plasmid DNA was prepared using a QIAGEN BioRobot 9600.

Example 17

Expression of the *Magnaporthe grisea* Lipase 1 Gene in *Aspergillus oryzae* BECh2

*Aspergillus oryzae* BECh2 protoplasts were prepared according to the method of Christensen et al., 1988, supra. Sixty μg of pHyGe010 was used to transform *Aspergillus oryzae* BECh2.

The transformation of *Aspergillus oryzae* BECh2 with pHyGe010 yielded 14 transformants. Each transformant was transferred to individual Cove plates. Confluent Cove plates of the 14 transformants were washed with 4 ml of 0.01% Tween 20. Two hundred μl of spore suspension was inoculated separately into 25 ml of MY25 medium in 125 ml plastic shake flasks and incubated at 34° C., 250 rpm. Three, four, and five days after incubation, culture supernatants were removed for lipase assay and SDS-PAGE analysis.

Lipase activity was determined as described in Example 8.

The lipase assay results indicated that at 3, 4, and 5 days, several transformants produced lipase activity above that of the untransformed control.

SDS-PAGE (BioRad Criterion 8-16% SDS-PAGE) analysis of 25 μl of the supernatants showed a major band at approximately 37 kDa.

Example 18

Determination of Substrate Specificity of Recombinant *Magnaporthe grisea* Lipase 1

The substrate specificity of *Magnaporthe grisea* lipase 1 was determined using a panel screen composed of 4-nitrophenol (PNP) lipase substrates as described in Example 9.

The results for the panel screen are shown in Table 3.

TABLE 3

Ratio of PNP-substrates according to Table 1, Example 9, where:
P = Palmitate, D = Decanoate, V = Valerate and B = Butyrate

Long chain/Short chain at pH 7.5

|  | P/V | D/V | P/B | D/B |
|---|---|---|---|---|
| Hyge027 | 1.142 | 0.747 | 1.657 | 1.103 |
| LIPOLASE ™ | 1.213 | 2.398 | 2.220 | 4.387 | pH Ratios; (−) = 0.2% Triton data

|  | 9.5P/7.0P | 9.5D/7.0D | 9.5P-/7.5P- |
|---|---|---|---|
| Hyge027 | No Data | No Data | No Data |
| LIPOLASE ™ | 1.527 | 1.881 | 1.452 |

No or Low Triton (−) compared to maximum Triton (+)

|  | V7.5 −/+ | D9.5 +/− | P7.5 +/− | P9.5 +/− |
|---|---|---|---|---|
| Hyge027 | 1.101 | No Data | 5.123 | No Data |
| LIPOLASE ™ | 8.651 | 6.378 | 9.206 | 9.502 |

No Data = not enough activity to give sufficient signal in one of the assays in this test
Hyge027 (*Aspergillus oryzae* BECh2 expressing *Magnaporthe grisea* lipase 1) test data consists of the average of up to 4 independent screening assay events; LIPOLASE ™ (*Thermomyces lanuginosus* lipase) test data consists of the average of up to 17 independent screening assay events.

In comparing the panel screen results of the *Thermomyces lanuginosus* lipase (LIPOLASE™) and Hyge027, the following observations were made:

(1) There were significant differences in the ratios of activities on valerate or palmitate at pH 7.5 (V7.5−/+ and P7.5+/−) in the presence or absence of triton for Hyge027 versus LIPOLASE™.

(2) The ratios of activities on decanoate versus valerate (D/V), palmitate versus butyrate (P/B), and decanoate versus butyrate (D/B) were significantly different for Hyge027 versus LIPOLASE™ suggesting there is some acyl change length specificity differences between the two lipases.

Example 19

Cloning of *Magnaporthe grisea* Lipase 2 Gene

Two synthetic oligonucleotide primers shown below were designed based on the predicted start and stop codons of the open reading frame to PCR amplify a *Magnaporthe grisea* lipase 2 gene from the genomic DNA prepared in Example 13.

```
Forward primer:
                                        (SEQ ID NO: 36)
5'-CCATGGCCATGATGAGGTTCCCCAGCGTGCTCA-3'

Reverse primer:
                                        (SEQ ID NO: 37)
5'-TTTAATTAAGCCACGGTCTTGTTGGCTTC-3'
```

Bold letters represent coding sequence. The remaining sequence is homologous to the enzyme restriction insertion sites of pBM120a.

The gene was amplified by PCR using the Herculase™ Hotstart DNA polymerase (Stratagene, La Jolla, Calif.). Fifty ng of each of the primers above were used in a PCR reaction containing 300 ng of *Magnaporthe grisea* genomic DNA. The PCR amplification reaction mixture also contained 1× Herculase PCR buffer, 1 μl of a dATP, dTTP, dGTP, and dCTP mix (10 mM each), and 2.5 units Herculase™ DNA polymerase mix in a final volume of 50 μl. To amplify the fragment, a Peltien thermal cycler (MJ Research Inc., Watertown, Mass.) was programmed for 1 cycle at 94° C. for 2 minutes; 30 cycles each at 94° C. for 1 minute, 50° C. for 1 minute, 72° C. 1 minute; 1 cycle at 72° C. for 10 minutes; and a 4° C. hold.

The PCR products were size fractionated on a 1% agarose gel using TAE buffer and a 1 kb product band was purified using a QIAquick Gel Purification Kit according to the manufacturer's instructions. The PCR product was then cloned into pCR2.1-TOPO according to manufacturer's instructions resulting in plasmid pCrAm138 (FIG. 12). Two μl of the ligation reaction was used to transform *E. coli* TOP10 One Shot competent cells. An *E. coli* transformant containing the plasmid pCrAm138 was detected by restriction digestion and plasmid DNA was prepared using a QIAGEN BioRobot 9600.

*E. coli* TOP10 One Shot cells containing pCrAm138 were deposited with the Agricultural Research Service Patent Culture Collection, Northern Regional Research Center, 1815 University Street, Peoria, Ill., 61604, as NRRL B-30781, with a deposit date of Oct. 12, 2004.

Example 20

Characterization of the *Magnaportha grisea* Genomic Sequence Encoding Lipase 2

DNA sequencing of the *Margnoportha grisea* lipase 2 gene contained in pCrAm138 was performed with a Perkin-Elmer Applied Biosystems Model 377 XL Automated DNA Sequencer using dye-terminator chemistry (Giesecke et al., 1992, supra) and primer walking strategy. Nucleotide sequence data were scrutinized for quality and all sequences were compared to each other with assistance of PHRED/PHRAP software (University of Washington, Seattle, Wash.).

Gene models for the lipase gene were predicted based on homology to a *Thermomyces lanuginosus* lipase (Accession No. O59952) as well as conserved sequences present at the 5' and 3' ends of fungal introns. The nucleotide sequence (SEQ ID NO: 7) and deduced amino acid sequence (SEQ ID NO: 8) are shown in FIG. 13. The genomic fragment encodes a polypeptide of 348 amino acids with a molecular weight of 37.7 kDa. The % G+C content of the gene is 64% and the mature polypeptide coding sequence (nucleotides 55 to 1044 of SEQ ID NO: 7) is 64%. Using the SignalP software program (Nielsen et al., 1997, supra), a signal peptide of 18 residues was predicted. The predicted mature protein contains 330 amino acids with a molecular mass of 35.9 kDa.

A comparative alignment of lipase sequences was determined using the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Magnaporthe* lipase 2 gene shares 37.8% identity to the deduced amino acid sequence of a *Thermomyces lanuginosus* lipase gene (Accession No. O59952).

Example 21

Cloning of *Magnaporthe grisea* Lipase 3 Gene

Two synthetic oligonucleotide primers shown below were designed based on the predicted start and stop codons of the open reading frame to PCR amplify a *Magnaporthe grisea* lipase 3 gene from the genomic DNA described in Example 13.

Forward primer:
(SEQ ID NO: 38)
5'-ACACAACTGGCCATGTTGTGGCGTCGGGCGGGTGGCCTCT-3'

Reverse primer:
(SEQ ID NO: 39)
5'-AGTCACCTCTAGTTAATTAATTAGAGCTCATCCTGGCCAGGAG CCAC-3'

Bold letters represent coding sequence. The remaining sequence is homologous to the insertion sites of pBM120a.

The fragment of interest was amplified by PCR using the Expand High Fidelity PCR System. Fifty picomoles of each of the primers above were used in a PCR reaction containing 300 ng of *Magnaporthe grisea* genomic DNA. The PCR amplification reaction mixture also contained 1×PCR buffer with 1.5 mM MgCl$_2$, 1 µl of a dATP, dTTP, dGTP, and dCTP mix (10 mM each), and 0.75 µl of DNA polymerase mix (3.5 U/µl) in a final volume of 50 µl. An Eppendorf Mastercycler thermocycler was used to amplify the fragment programmed for 1 cycle at 94° C. for 2 minutes; 10 cycles each at 94° C. for 15 seconds, 62° C. for 30 seconds, and 72° C. for 2 minutes; 15 cycles each at 94° C. for 15 seconds, 62° C. for 30 seconds, and 72° C. for 2 minutes plus a 5 second elongation at each successive cycle; 1 cycle at 72° C. for 7 minutes; and a 10° C. hold.

The 1.2 kb reaction product was visualized on a 1.0% agarose gel using TBE buffer. Four microliters of the product was then cloned into pCR2.1-TOPO according to manufacturer's instructions to produce pBM135a. Two µl of the reaction was used to transform *E. coli* TOP10 One Shot competent cells. An *E. coli* transformant containing pBM135a was detected by restriction digestion and plasmid DNA was prepared using a QIAGEN BioRobot 9600.

DNA sequencing of the *Magnaporthe grisea* lipase 3 gene from pBM135a was performed with a Perkin-Elmer Applied Biosystems Model 377 XL Automated DNA Sequencer using dye-terminator chemistry (Giesecke et al., 1992, supra) and primer walking strategy. Nucleotide sequence data were scrutinized for quality and all sequences were analyzed with assistance of ContigExpress software (Informax, Inc., Bethesda, Md.). Sequencing results indicated the absence of the ATG start codon in pBM135a. A second forward primer, with sequence identical to oligo number 998205 described above was ordered. The new oligo numbered 998524 was used in a PCR reaction using pBM135a as DNA template to re-amplify the gene of interest.

Using the Expand High Fidelity PCR System, 50 picomoles of primers 998524 and 998232 were used in a PCR reaction containing 1 µl of a 1:10 dilution pBM135a mini DNA. The PCR amplification reaction mixture also contained 1×PCR buffer with 1.5 mM MgCl$_2$, 1 µl of a dATP, dTTP, dGTP, and dCTP mix (10 mM each), and 0.75 µl of DNA polymerase mix (3.5 U/µl) in a final volume of 50 µl. An Eppendorf Mastercycler thermocycler was used to amplify the fragment programmed for 1 cycle at 94° C. for 2 minutes; 10 cycles each at 94° C. for 15 seconds, 62° C. for 30 seconds, and 72° C. for 1 minute, 15 seconds; 15 cycles each at 94° C. for 15 seconds, 62° C. for 30 seconds, and 72° C. for 1 minute 15 seconds, plus a 5 second elongation at each successive cycle; 1 cycle at 72° C. for 7 minutes; and a 10° C. hold.

Figure 14:
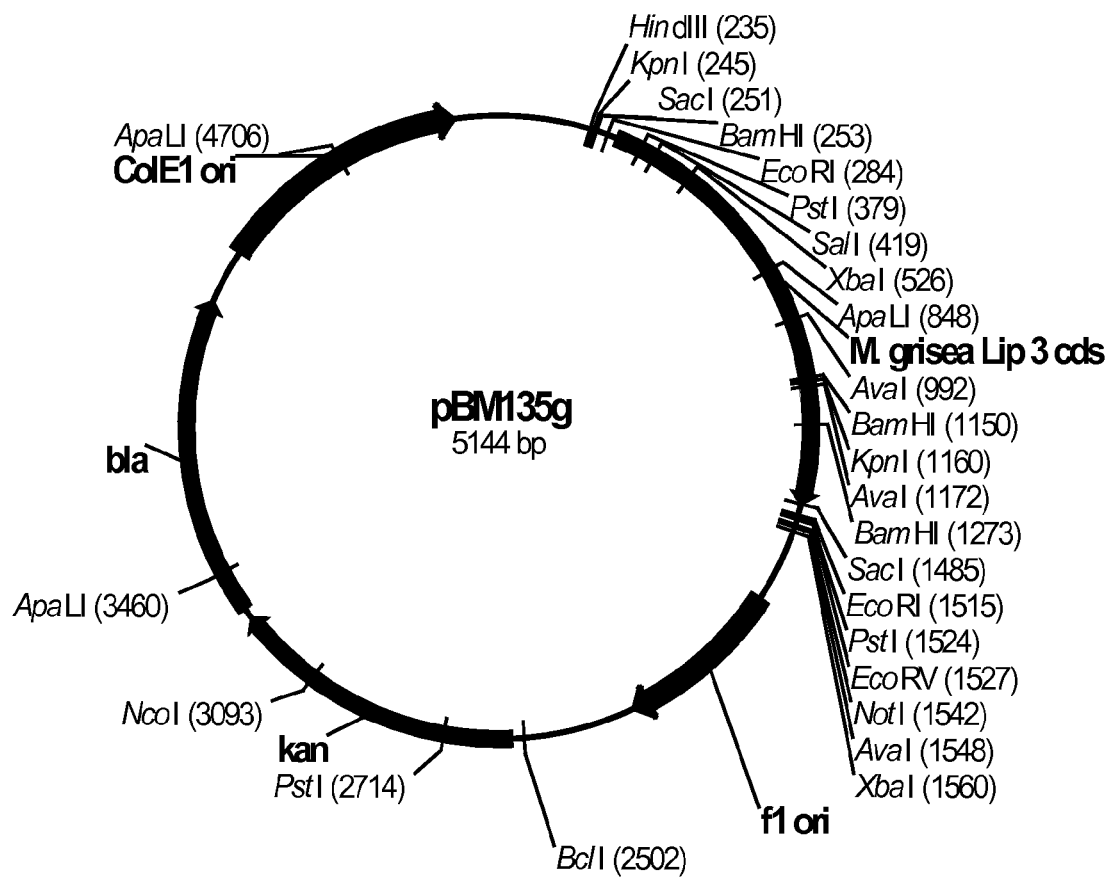
FIG. 14 shows a restriction map of pBM135g.

The 1.2 kb reaction product was visualized on a 1.0% agarose gel using TBE buffer. The 1.2 kb fragment was excised from the gel and purified using a Qiagen Gel Extraction Kit. Two microliters of the product was then cloned into pCR2.1-TOPO according to manufacturer's instructions to produce pBM135g (FIG. 14). Two µl of the reaction was used to transform *E. coli* TOP10 One Shot competent cells. An *E. coli* transformant containing pBM135g was detected by restriction digestion and plasmid DNA was prepared using a QIAGEN BioRobot 9600.

*E. coli* TOP10 One Shot cells containing pBM135g were deposited with the Agricultural Research Service Patent Culture Collection, Northern Regional Research Center, 1815 University Street, Peoria, Ill., 61604, as NRRL B-30779, with a deposit date of Oct. 12, 2004.

Example 22

Characterization of the *Magnaporthe grisea* Genomic Sequence Encoding Lipase 3

DNA sequencing of the *Magnaporthe grisea* lipase 3 gene from plasmid, pBM135g, was performed with a Perkin-Elmer Applied Biosystems Model 377 XL Automated DNA Sequencer using dye-terminator chemistry (Giesecke et al., 1992, supra) and primer walking strategy. Nucleotide sequence data were scrutinized for quality and all sequences were analyzed with assistance of Contig Express software.

Gene models for the lipase gene were predicted based on homology to a *Thermomyces lanuginosus* lipase (Accession No. O59952) as well as conserved sequences present at the 5' and 3' ends of fungal introns. The genomic coding sequence (SEQ ID NO: 9) and deduced amino acid sequence (SEQ ID NO: 10) for pBM135g and is shown in FIG. 15. The genomic fragment encodes a polypeptide of 393 amino acids. The % G+C content of the gene is 58.71% and the mature polypeptide coding sequence (nucleotides 73 to 1179 of SEQ ID NO: 9) is 58.4%. Using the SignalP software program (Nielsen et al., 1997, supra), a signal peptide of 24 residues was predicted. The predicted mature protein contains 369 amino acids with a molecular mass of 40.8 kDa.

A comparative alignment of lipase sequences was determined using the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Magnaporthe grisea* lipase 3 gene shares 20.5% identity to the deduced amino acid sequence of the *Thermomyces lanuginosus* lipase gene (Accession No. O59952).

Example 23

Identification of Lipase Genes in the Genomic Sequence of *Aspergillus nidulans*

A tfasty search (Pearson, W. R., 1999, supra) of the *Aspergillus nidulans* partial genome sequence (The Institute for Genomic Research, Rockville, Md.) was carried out using as query a lipase protein sequence from *Thermomyces lanuginosus* (Accession No. O59952). Several genes were identified as putative homologs based upon an E value of less than 0.001 in the tfasty output. Three genomic regions of approximately 780 bp, 600 bp, and 960 bp with 45.8, 34, and 33% identity to the query sequence at the amino acid level were identified. Gene models for the putative lipase genes were predicted based on homology to the *Thermomyces lanuginosus* lipase as well as conserved sequences present at the 5' and 3' ends of fungal introns.

Example 24

Aspergillus nidulans Genomic DNA Extraction

Four hundred μl of *Aspergillus nidulans* A1000 (Fungal Genetics Stock Center, Kansas City, Mo.) spores were grown in 50 ml of YP medium in a baffled shake flask at 37° C. and 250 rpm for 24 hours. Genomic DNA was then extracted from the mycelia using a DNeasy Plant Mini Kit according to manufacturer's instructions.

Example 25

Cloning of the *Aspergillus nidulans* Lipase 1 Gene

Two synthetic oligonucleotide primers shown below were designed based on the predicted start and stop codons of the open reading frame to PCR amplify an *Aspergillus* nidulans gene encoding a lipase from the genomic DNA prepared in Example 24.

```
Forward primer:
                                       (SEQ ID NO: 40)
5'-ACACAACTGGCCATGATCCGTTTGGGGTATTCTGCC-3'

Reverse primer:
                                       (SEQ ID NO: 41)
5'-AGTCACCTCTAGTTAATTAATTACTGGCAGGCAGTGATAT-3'
```

Bold letters represent coding sequence. The remaining sequence is homologous to the insertion sites of pBM120a (see Example 6).

The fragment of interest was amplified by PCR using the Expand High Fidelity PCR System. One μM of each of the primers above were used in a PCR reaction containing 20 ng of *Aspergillus nidulans* genomic DNA, 1×PCR buffer with 1.5 mM $MgCl_2$, 1 μl of a dATP, dTTP, dGTP, and dCTP mix (10 mM each), and 0.75 μl of DNA polymerase mix (3.5 U/μl) in a final volume of 50 μl. To amplify the fragment, an Eppendorf Mastercycler thermocycler was programmed for 1 cycle at 94° C. for 2 minutes; 10 cycles each at 94° C. for 15 seconds, 59.5° C. for 30 seconds, and 72° C. for 1.25 minutes; 15 cycles each at 94° C. for 15 seconds, 59.5° C. for 30 seconds, and 72° C. for 1.25 minutes plus a 5 second elongation at each successive cycle; 1 cycle at 72° C. for 7 minutes; and a 10° C. hold.

Figure 16:
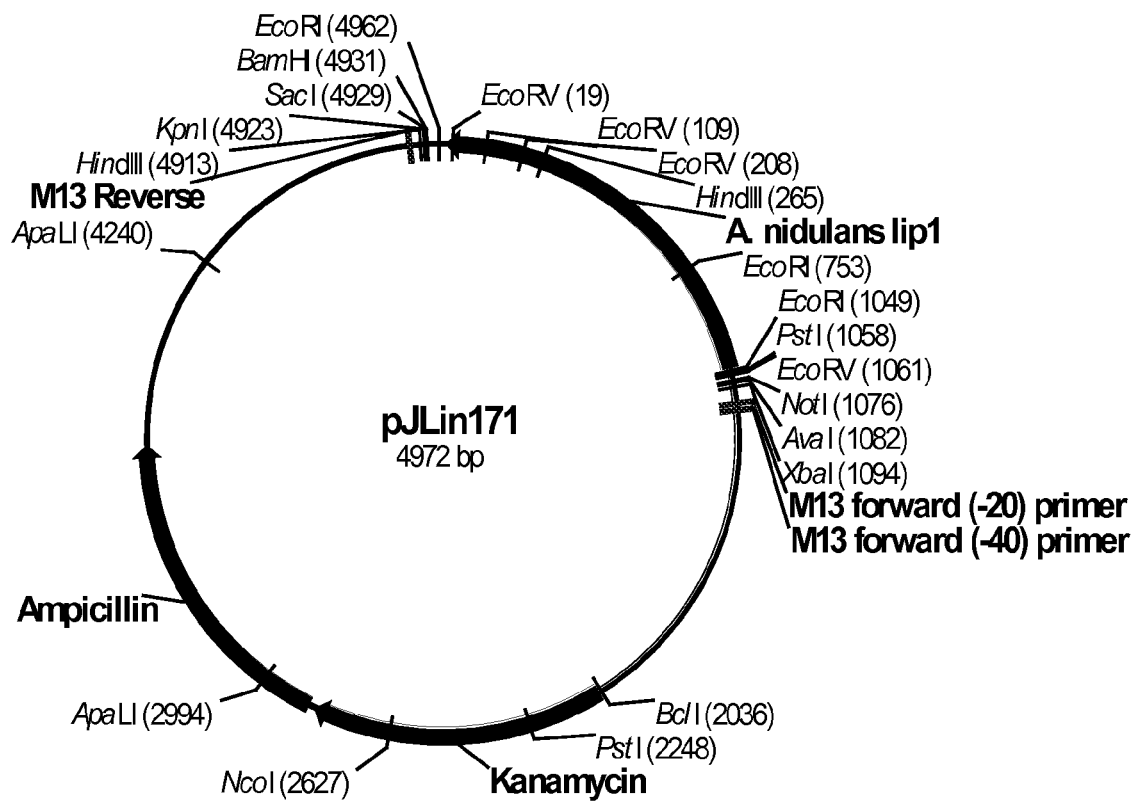
FIG. 16 shows a restriction map of pJLin171.

The reaction product was visualized on a 0.7% agarose gel using TBE buffer and the 1.1 kb product band was purified using a QIAquick PCR Purification Kit according to the manufacturer's instructions. The PCR fragment and pCR2.1-TOPO were ligated using conditions specified by the manufacturer resulting in plasmid pJLin171 (FIG. 16).

Two μl of the reaction was used to transform *E. coli* TOP10 One Shot competent cells according to the manufacturer's instructions. A 2 μl volume of the ligation mixture was added to the *E. coli* cells and incubated on ice for 20 minutes. Subsequently, the cells were heat shocked for 30 seconds at 42° C., and then placed on ice for 2 minutes. A 250 μl volume of SOC medium was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid. Twelve colonies that grew on the plates were picked with a sterile toothpick and grown overnight at 37° C., 250 rpm in a 15 ml Falcon tube containing 3 ml of LB medium supplemented with 100 μg of ampicillin per ml. An *E. coli* transformant containing the pJLin171 was detected by restriction digestion and plasmid DNA was prepared using a BioRobot 9600.

*E. coli* TOP 10 One Shot cells containing pJLin171 were deposited with the Agricultural Research Service Patent Culture Collection, Northern Regional Research Center, 1815 University Street, Peoria, Ill., 61604, as NRRL B-30755, with a deposit date of Jul. 21, 2004.

Example 26

Characterization of the *Aspergillus nidulans* Genomic Sequence Encoding Lipase 1

DNA sequencing of the *Aspergillus nidulans* lipase 1 gene from pJLin171 was performed with an Applied Biosystems Model 377 XL DNA Sequencer using dye-terminator chemistry (Giesecke et al., 1992, supra) and primer walking strategy. Nucleotide sequence data were scrutinized for quality and all sequences were compared to each other with assistance of PHRED/PHRAP software (University of Washington, Seattle, Wash.).

Gene models for the lipase gene were predicted based on homology to the *Thermomyces lanuginosus* lipase as well as conserved sequences present at the 5' and 3' ends of fungal introns. The nucleotide sequence (SEQ ID NO: 11) and deduced amino acid sequence (SEQ ID NO: 12) are shown in FIG. 17. The genomic fragment encodes a polypeptide of 294 amino acids, interrupted by 3 introns of 47 bp, 59 bp, and 50 bp. The % G+C content of the gene is 54.5% and of the mature protein coding region (nucleotides 58 to 1038 of SEQ ID NO: 11) is 54.5%. Using the SignalP software program (Nielsen et al., 1997, supra), a signal peptide of 19 residues was predicted. The predicted mature protein contains 275 amino acids with a molecular mass of 29.4 kDa.

A comparative alignment of lipase sequences was made employing the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus nidulans* lipase 1 gene shares 48% identity to the deduced amino acid sequence of a *Thermomyces lanuginosus* lipase gene (accession number O59952).

Example 27

Figure 18:
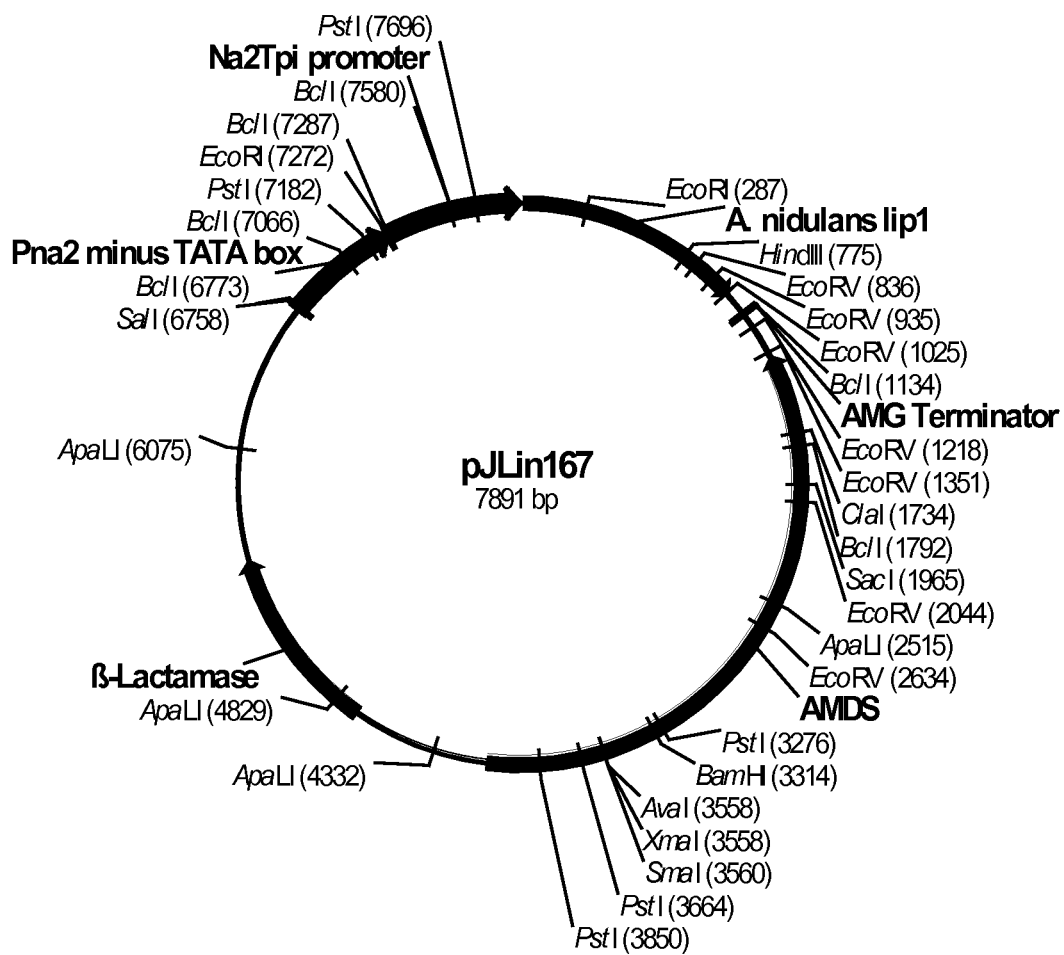
FIG. 18 shows a restriction map of pJLin167.

Construction of an *Aspergillus oryzae* Expression Vector Expressing *Aspergillus nidulans* Lipase 1 Gene The 1.1 kb PCR fragment (Example 25) containing the *Aspergillus nidulans* lipase 1 gene was cloned into pBM120a using an InFusion Cloning Kit where the vector was digested with Nco I and Pac I. The digested vector was purified by gel electrophoresis using a 0.7% agarose gel with TBE buffer, and the PCR fragment was extracted using a QIAquick Gel Extraction Kit and purified using a QIAquick PCR Purification Kit. The gene fragment and the digested vector were ligated together in a reaction resulting in the expression plasmid pJLin167 (FIG. 18). The ligation reaction (50 μl) was composed of 1× InFusion Buffer, 1×BSA, 1 μl of Infusion enzyme (diluted 1:10), 100 ng of pBM120a digested with Nco I and Pac I, and 50 ng of the *Aspergillus nidulans* lipase 1 gene purified PCR product. The reaction was incubated at room temperature for 30 minutes. Two μl of the reaction was used to transform *E. coli* SoloPack® Gold supercompetent cells according to the manufacturer's instructions. One μl of β-mercaptoethanol was added to competent cells, and incubated on ice for 10 minutes. A 2 μl volume of the ligation mixture was then added to the *E. coli* cells and incubated on ice for 30 minutes. Subsequently, the cells were heat shocked for 60 seconds at 54° C., and then placed on ice for 2 minutes. A 150 μl volume of NZY+ medium at 42° C. was added to the cells and the mixture was incubated for 1 hour at 37° C. and 250 rpm. After the incubation the colonies were spread on 2×YT plates supplemented with 100 μg of ampicillin per ml and incubated at 37° C. overnight for selection of the plasmid. Twelve colonies that grew on the plates were picked with a sterile toothpick and grown overnight at 37° C., 250 rpm in a 15 ml Falcon tube containing 3 ml of LB medium supplemented with 100 μg of ampicillin per ml. An *E. coli* transformant containing the pJLin167 plasmid was detected by restriction digestion and plasmid DNA was prepared using a QIAGEN BioRobot 9600.

Example 28

Expression of the *Aspergillus nidulans* Lipase 1 Gene in *Aspergillus oryzae* BECh2

*Aspergillus oryzae* BECh2 (Δalp, Δamy, CPA-, KA-, Δnp1) protoplasts were prepared according to the method of Christensen et al., 1988, *Bio/Technology* 6: 1419-1422. Five μg of pJLin167 was used to transform *Aspergillus oryzae* BECh2.

The transformation of *Aspergillus oryzae* BECh2 with pJLin167 yielded 34 transformants. The transformants were isolated to individual Cove plates. Confluent Cove plates of 28 transformants were washed with 4 ml of 0.01% Tween 20. Two hundred μl of spore suspension was inoculated separately into 25 ml of MY25 medium in 125 ml plastic shake flasks and incubated at 34° C., 250 rpm. Three and five days after incubation, culture supernatants were removed for lipase assay and SDS-PAGE analysis.

Lipase activity was determined as described in Example 8. The lipase assay results indicated that at both 3 and 5 days, 27 of the 28 transformants produced lipase activity well above that of the untransformed control.

SDS-PAGE (BioRad Criterion 10-20% SDS-PAGE) analysis of 10 μl of the supernatants showed a major band at approximately 30 kDa.

Example 29

Purification and Characterization of Recombinant *Aspergillus nidulans* Lipase 1

One of the *Aspergillus oryzae* transformants producing the highest yield of *Aspergillus nidulans* lipase 1 was grown in 500 ml of MY25 medium for 4 days at 30° C., 250 rpm for purification. Supernatant was sterile filtered under pressure using SEITZ-EKS filters (PALL Corporation, Waldstetten, Germany). The sterile filtered supernatant was then adjusted to pH 9 and sodium chloride was added to a final concentration of 2 M.

Decylamine agarose was custom made by UpFront Chromatography A/S, Lersø Parkalle Denmark. The decylamine agarose matrix was packed into a 50 ml column and then washed and equilibrated with 50 mM borate pH 9 buffer containing 2 M sodium chloride. Filtered fermentation supernatant was then applied to the column using an Akta explorer system. Unbound material was washed with 50 mM borate pH 9 buffer containing 1 M sodium chloride. The bound proteins were eluted with 50 mM borate pH 9 buffer containing 30% 2-propanol as an eluent.

Fractions of 10 ml were collected and analyzed for lipase activity according to the assay described by Svendsen et al., in *Methods in Enzymology*, Lipases Part a Biotechnology Vol. 284 pages 317-340 Edited by Byron Rubin and Edward A. Dennis, Academic Press, 1997, New York. Fractions containing lipase activity were then pooled and diluted to adjust the ionic strength below 4 mSi.

A 50 ml FFQ Sepharose (Pharmacia Amersham, Uppsala, Sweden) column was washed and equilibrated with 50 mM borate pH 9 buffer. The decylamine agarose pool containing activity was then applied onto the column and washed with the same buffer to remove unbound material. Bound proteins were then eluted using linear salt gradient using 50 mM borate pH 9 buffer containing 0.5 M sodium chloride.

Fractions of 10 ml were collected and analyzed for activity as described above and fractions were also analyzed by SDS-PAGE for purity. Best fractions contain highest lipase activity and best purity judged by SDS-PAGE was pooled. SDS-PAGE showed a pure protein band with molecular weight between 33 to 35 kDa protein which is usually seen due to glycosylation.

Substrate specificity of the *Aspergillus nidulans* lipase 1 was evaluated at pH 7 according to WO 2005/040410. The results showed that the *Aspergillus nidulans* lipase 1 efficiently degrades phospholipids such as lecithin (and alkylated phosphatidylethanolamins) and well as triliolein.

Example 30

Determination of Thermostability of Recombinant *Aspergillus nidulans* Lipase 1

The thermostability of purified recombinant *Aspergillus nidulans* lipase 1 (Example 29) was determined by Differential Scanning calorimetry (DSC). The thermal denaturation temperature, Td, was taken as the top of the denaturation peak (major endothermic peak) in thermograms (Cp vs. T) obtained after heating of enzyme solutions at a constant programmed heating rate. Cp refers to heat capacity (at constant pressure). T refers to temperature.

A VP-DSC Differential Scanning calorimeter (MicroCal Inc., Northampton, Mass.) was used for the thermostability determination according to the manufacturer's instructions. Sample enzyme and reference solutions were carefully degassed immediately prior to loading of samples into the calorimeter (reference: buffer without enzyme). Sample enzyme (approximately 1 mg/ml) and reference solutions (approximately 0.5 ml) were thermally pre-equillibrated for 20 minutes at 5° C. The DSC scan was performed from 5° C. to 95° C. at a scan rate of approximately 90 K/hr. Denaturation temperatures were determined at an accuracy of approx. +/−1° C.

The results as shown in Table 4 indicated that the *Aspergillus nidulans* lipase 1 had thermal denaturation temperatures of 63° C. in 50 mM acetate pH 5.0 buffer and 55° C. in 50 mM glycine pH 10.0 buffer.

TABLE 4

Thermostability Determination

| Buffer | pH | Td (° C.) |
|---|---|---|
| 50 mM Acetate | 5.0 | 63 |
| 50 mM Glycine | 10.0 | 55 |

Example 31

Cloning of the *Aspergillus nidulans* Lipase 2 Gene

Two synthetic oligonucleotide primers shown below were designed based on the predicted start and stop codons of the open reading frame to PCR amplify an *Aspergillus nidulans* lipase 2 gene from the genomic DNA prepared in Example 24.

```
Forward primer:
                                          (SEQ ID NO: 42)
5'-ACACAACTGGCCATGTATTTCCTTCTCTCCGTCATC-3'

Reverse primer:
                                          (SEQ ID NO: 43)
5'-AGTCACCTCTAGTTAATTAATCAGCCTAGTGGGCAAGCAT-3'
```

Bold letters represent coding sequence. The remaining sequence is homologous to the insertion sites of pBM120a.

Figure 19:
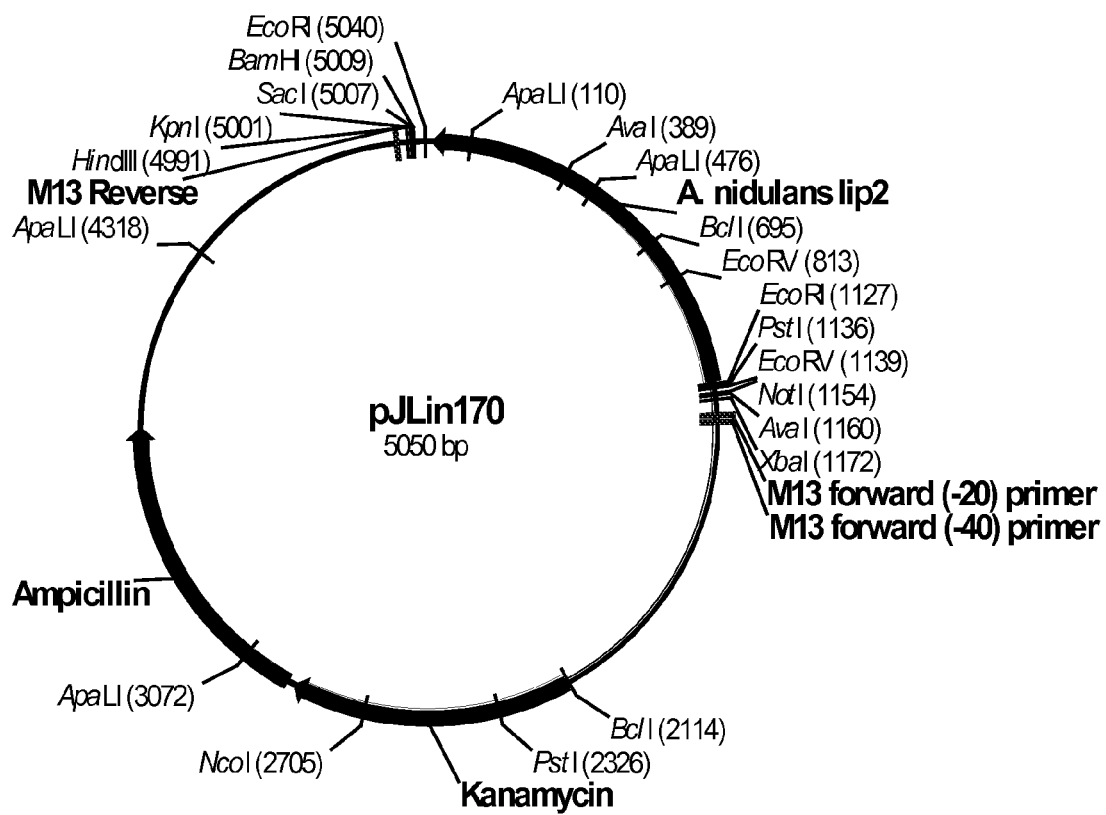
FIG. 19 shows a restriction map of pJLin170.

The fragment was amplified by PCR using the Expand High Fidelity PCR System as described in Example 25. The reaction product was visualized on a 0.7% agarose gel using TBE buffer and a 1.2 kb product band was purified using a QIAquick PCR Purification Kit according to the manufacturer's instructions. The PCR product was then cloned into pCR2.1-TOPO according to manufacturer's instructions to produce pJLin170 (FIG. 19). Two µl of the reaction was used to transform *E. coli* TOP10 One Shot competent cells as described in Example 25. An *E. coli* transformant containing the pJLin170 plasmid was detected by restriction digestion and plasmid DNA was prepared using a QIAGEN BioRobot 9600.

*E. coli* TOP 10 One Shot cells containing pJLin170 were deposited with the Agricultural Research Service Patent Culture Collection, Northern Regional Research Center, 1815 University Street, Peoria, Ill., 61604, as NRRL B-30754, with a deposit date of Jul. 21, 2004.

Example 32

Characterization of the *Aspergillus nidulans* Genomic Sequence Encoding Lipase 2

DNA sequencing of the *Aspergillus nidulans* lipase 2 gene from pJLin170 was performed with an Applied Biosystems Model 377 XL DNA Sequencer using dye-terminator chemistry (Giesecke et al., 1992, supra) and primer walking strategy. Nucleotide sequence data were scrutinized for quality and sequences were compared to each other with assistance of PHRED/PHRAP software (University of Washington, Seattle, Wash.).

Gene models for the lipase gene were predicted based on homology to the *Thermomyces lanuginosus* lipase as well as conserved sequences present at the 5' and 3' ends of fungal introns. The nucleotide sequence (SEQ ID NO: 13) and deduced amino acid sequence (SEQ ID NO: 14) are shown in FIG. 20. The genomic fragment encodes a polypeptide of 308 amino acids, interrupted by 3 introns of 49, 73 and 70 bp. The % G+C content of the gene is 51.7% and the mature protein coding region (nucleotides 73 to 1116 of SEQ ID NO: 13) is 51.9%. Using the SignalP software program (Nielsen et al., 1997, supra), a signal peptide of 24 residues was predicted. The predicted mature protein contains 284 amino acids with a molecular mass of 30.5 kDa.

A comparative alignment of lipase sequences was made employing the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus nidulans* lipase 2 gene shares 37% identity to the deduced amino acid sequence of a *Thermomyces lanuginosus* lipase gene (accession number O59952).

Example 33

Cloning of the *Aspergillus nidulans* Lipase 3 Gene

Two synthetic oligonucleotide primers shown below were designed based on the predicted start and stop codons of the open reading frame to PCR amplify an *Aspergillus nidulans* lipase 3 gene from the genomic DNA prepared in Example 24.

```
Forward primer:
                                          (SEQ ID NO: 44)
5'-ACACAACTGGCCATGACGGTGTCTCTTGACAGTTTATTCC-3'

Reverse primer:
                                          (SEQ ID NO: 45)
5'-AGTCACCTCTAGTTAATTAATCACCCCCCTGACAAATCTCCC
TTGG-3'
```

Bold letters represent coding sequence. The remaining sequence is homologous to the insertion sites of pBM120a.

The fragment of interest was amplified by PCR using the Expand High Fidelity PCR System. Fifty picomoles of each of the primers above were used in a PCR reaction containing 25 ng of *Aspergillus nidulans* genomic DNA. The PCR amplification reaction mixture also contained 1× PCR buffer with 1.5 mM MgCl$_2$, 1 µl of a dATP, dTTP, dGTP, and dCTP mix (10 mM each), and 0.75 µl of DNA polymerase mix (3.5 U/µl) in a final volume of 50 µl. An Eppendorf Mastercycler thermocycler was used to amplify the fragment programmed for 1 cycle at 94° C. for 2 minutes; 10 cycles each at 94° C. for 15 seconds, 62° C. for 30 seconds, and 72° C. for 3 minutes; 15 cycles each at 94° C. for 15 seconds, 62° C. for 30 seconds, and 72° C. for 3 minutes plus a 5 second elongation at each successive cycle; 1 cycle at 72° C. for 7 minutes; and a 10° C. hold.

The reaction product was visualized on a 1.0% agarose gel using TBE buffer and the 1.3 kb product band was purified using a QIAquick PCR Purification Kit according to the manufacturer's instructions.

Example 34

Figure 21:
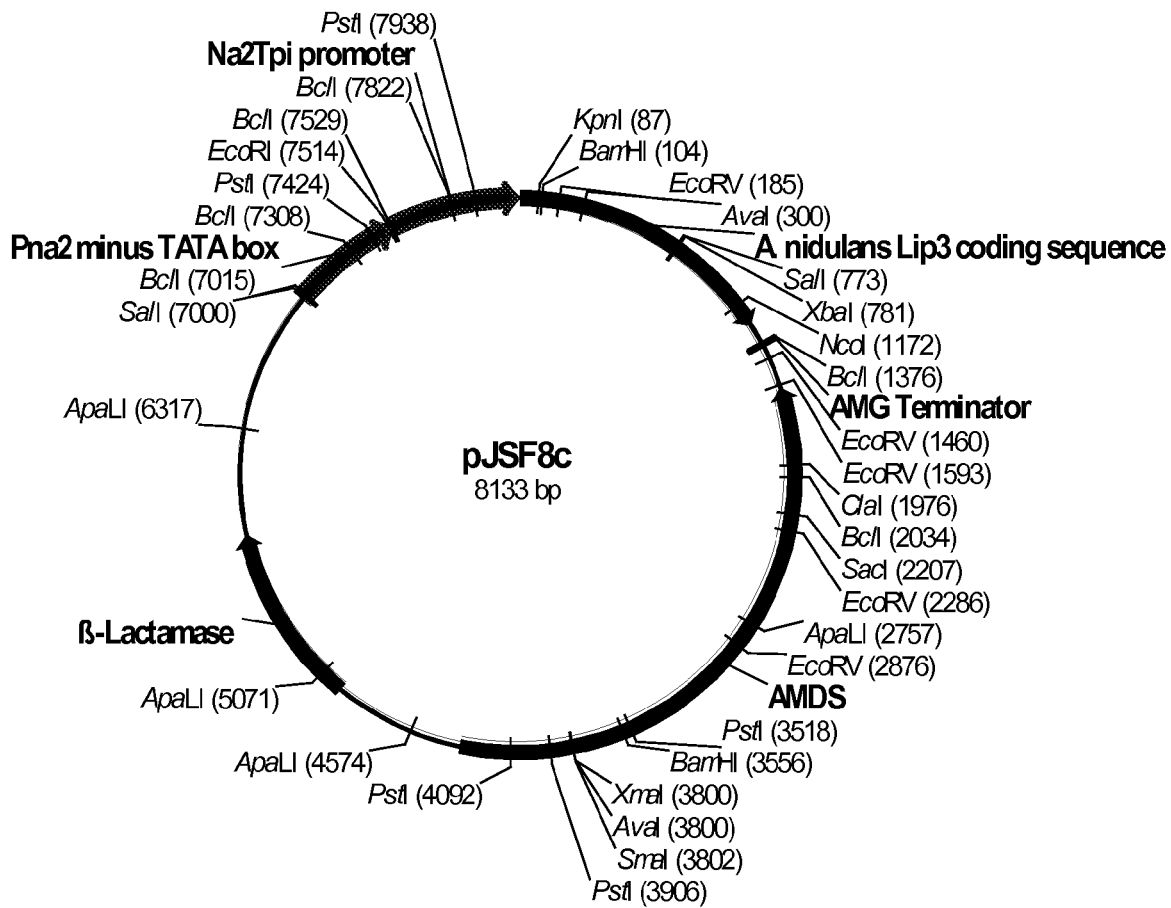
FIG. 21 shows a restriction map of pJSF8c.

Construction of an *Aspergillus oryzae* Expression Vector Expressing *Aspergillus nidulans* Lipase 3 Gene The PCR fragment containing the *Aspergillus nidulans* lipase 3 gene described in Example 33 was cloned into the pBM120a expression vector using an InFusion Cloning Kit. The vector was digested with restriction endonucleases Nco I and Pac I (using conditions specified by the manufacturer). The digested vector was purified by gel electrophoresis and extracted using a QIAquick Gel Extraction Kit, and the PCR fragment was purified using a QIAquick PCR Purification kit. The gene fragment and the digested vector were ligated together in a reaction resulting in the expression plasmid pJSF8c (FIG. 21). The ligation reaction (20 µl) was composed of 1× InFusion Buffer, 1×BSA, 1 µl of Infusion enzyme (diluted 1:10), 100 ng of pBM120a digested with Nco I and Pac I, and 50 ng of the Aspergillus nidulans lipase 3 gene purified PCR product. The reaction was incubated at room temperature for 30 minutes. Two µl of the reaction was used to transform E. coli SoloPack® Gold supercompetent cells. An E. coli transformant containing the pJSF8c plasmid was detected by restriction digestion and plasmid DNA was prepared using a QIAGEN BioRobot 9600.

Example 35

Construction of an *Aspergillus nidulans* Lipase 3 Gene Cloning Vector

The two synthetic oligonucleotide primers described in Example 33 were used to PCR amplify the genomic coding region of the Aspergillus nidulans lipase 3 gene from plasmid pJSF8c.

The fragment of interest was amplified by PCR using the Expand High Fidelity PCR System. Fifty picomoles of each of the primers above were used in a PCR reaction containing 1:10 dilution of plasmid, pJSF8c, mini DNA. The PCR amplification reaction mixture also contained 1×PCR buffer with 1.5 mM MgCl$_2$, 1 µl of a dATP, dTTP, dGTP, and dCTP mix (10 mM each), and 0.5 µl DNA polymerase mix (3.5 U/µl) in a final volume of 50 µl. An Eppendorf Mastercycler thermocycler was used to amplify the fragment programmed for 1 cycle at 94° C. for 2 minutes; 10 cycles each at 94° C. for 15 seconds, 62° C. for 30 seconds, and 72° C. for 1 minute, 15 seconds; 15 cycles each at 94° C. for 15 seconds, 62° C. for 30 seconds, and 72° C. for 1 minute, 15 seconds plus a 5 second elongation at each successive cycle; 1 cycle at 72° C. for 7 minutes; and a 10° C. hold.

Figure 22:
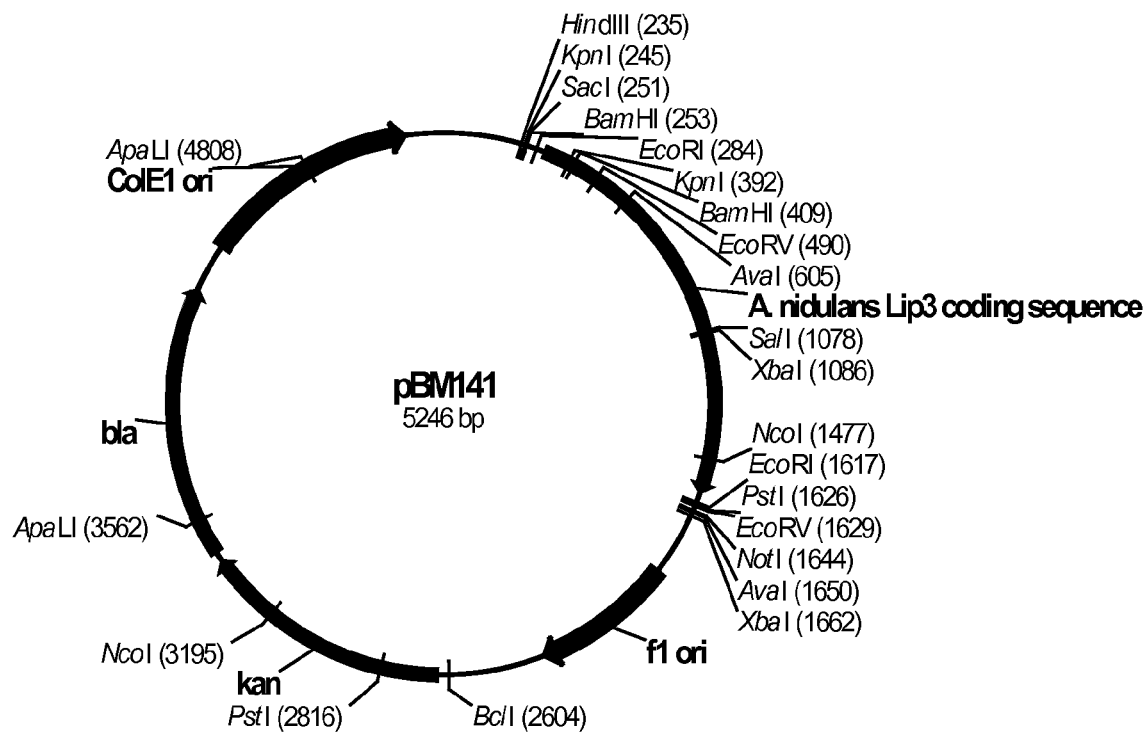
FIG. 22 shows a restriction map of pBM141.

The 1.3 kb PCR product was then cloned into pCR2.1-TOPO according to manufacturer's instructions to produce pBM141 (FIG. 22). Two µl of the reaction was used to transform E. coli TOP10 One Shot competent cells. An E. coli transformant containing pBM141 was detected by restriction digestion and plasmid DNA was prepared using a QIAGEN BioRobot 9600.

E. coli TOP 10 One Shot cells containing pBM141 were deposited with the Agricultural Research Service Patent Culture Collection, Northern Regional Research Center, 1815 University Street, Peoria, Ill., 61604, as NRRL B-30780, with a deposit date of Oct. 12, 2004.

Example 36

Characterization of the *Aspergillus nidulans* Genomic Sequence Encoding Lipase 3

DNA sequencing of the *Aspergillus nidulans* lipase 3 gene from pJSF8c and pBM141 was performed with a Perkin-Elmer Applied Biosystems Model 377 XL Automated DNA Sequencer (Perkin-Elmer/Applied Biosystems, Inc., Foster City, Calif.) using dye-terminator chemistry (Giesecke et al., 1992, supra) and primer walking strategy. Nucleotide sequence data were scrutinized for quality and all sequences were analyzed with assistance of ContigExpress software (Informax, Inc., Bethesda, Md.).

Gene models for the putative lipase genes were predicted based on homology to a *Thermomyces lanuginosus* lipase as well as conserved sequences present at the 5' and 3' ends of fungal introns. The genomic coding sequence (SEQ ID NO: 15) and deduced amino acid sequence (SEQ ID NO: 16) are identical for pJSF8c and pBM141 and are shown in FIG. 23. The genomic fragment encodes a polypeptide of 404 amino acids, interrupted by 1 intron of 68 bp. The % G+C content of the gene is 52.14% and the mature protein coding region (nucleotides 76 to 1280 of SEQ ID NO: 15) is 52.3%. Using the SignalP software program (Nielsen et al., 1997, supra), a signal peptide of 25 residues was predicted. The predicted mature protein contains 380 amino acids with a molecular mass of 42.4 kDa.

A comparative alignment of lipase sequences was determined using the Clustal W method (Higgins, 1989, supra) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5. The alignment showed that the deduced amino acid sequence of the *Aspergillus nidulans* lipase 3 gene shares 21.6% identity to the deduced amino acid sequence of a *Thermomyces lanuginosus* lipase gene (accession number O59952).

Deposit of Biological Material

The following biological materials have been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
| --- | --- | --- |
| E. coli (pSMO223) | NRRL B-30773 | Sep. 16, 2004 |
| E. coli (pSMO224) | NRRL B-30774 | Sep. 16, 2004 |
| E. coli pHyGe026 | NRRL B-30772 | Sep. 13, 2004 |
| E. coli pBM135g | NRRL B-30779 | Oct. 12, 2004 |
| E. coli pCrAm138 | NRRL B-30781 | Oct. 12, 2004 |
| E. coli pJLin170 | NRRL B-30754 | Jul. 21, 2004 |
| E. coli pJLin171 | NRRL B-30755 | Jul. 21, 2004 |
| E. coli pBM141 | NRRL B-30780 | Oct. 12, 2004 |

The strains have been deposited under conditions that assure that access to the cultures will be available during the pendency of this patent application to one determined by the Commissioner of Patents and Trademarks to be entitled thereto under 37 C.F.R. §1.14 and 35 U.S.C. §122. The deposits represent substantially pure cultures of the deposited strains. The deposits are available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifica-

What is claimed is:

1. A detergent composition comprising an isolated polypeptide having lipase activity, selected from the group consisting of:

(a) a polypeptide comprising an amino acid sequence having at least 95% identity with the mature polypeptide of SEQ ID NO: 8;

(b) a polypeptide encoded by a polynucleotide which hybridizes under at least high stringency conditions with (i) the mature polypeptide coding sequence of SEQ ID NO: 7, (ii) the cDNA sequence contained in the mature polypeptide coding sequence of SEQ ID NO: 7, or (iii) a full-length complementary strand of (i) or (ii), wherein the high stringency conditions are defined as prehybridization and hybridization at 42° C. in 5× SSPE, 0.3%

SDS, 200 μg/ml sheared and denatured salmon sperm DNA, and 50% formamide, and washing three times each for 15 minutes using 2× SSC, 0.2% SDS at 65° C.; and (c) a polypeptide encoded by a polynucleotide comprising a nucleotide sequence having at least 95% identity with the mature polypeptide coding sequence of SEQ ID NO: 7; a surfactant, and a stabilizing agent.

2. The detergent composition of claim 1, wherein the polypeptide includes the amino acid sequence of SEQ ID NO: 8; or a fragment thereof having lipase activity.

3. The detergent composition of claim 1, wherein the polypeptide includes the mature polypeptide of SEQ ID NO: 8.

4. The detergent composition of claim 1, wherein the polypeptide consists of SEQ ID NO: 8; or a fragment thereof having lipase activity.

5. The detergent composition of claim 1, wherein the polypeptide consists of the mature polypeptide of SEQ ID NO: 8.

6. The detergent composition of claim 1, wherein the mature polypeptide is amino acids 19 to 348 of SEQ ID NO: 8.

7. The detergent composition of claim 1, wherein the mature polypeptide coding sequence is nucleotides 55 to 1044 of SEQ ID NO: 7.

8. The detergent composition of claim 1, wherein the surfactant includes one or more non-ionic surfactants.

9. The detergent composition of claim 1, wherein the surfactant is present at a level of from 0.1% to 60% by weight.

10. The detergent composition of claim 1, wherein the surfactant includes one or more of linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, soap, alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, and N-acyl N-alkyl derivatives of glucosamine (glucamides).

11. The detergent composition of claim 1, additionally including one or more enzymes.

12. The detergent composition of claim 11, wherein the one or more enzymes include cellulases, proteases, lipases, amylases, and peroxidases/oxidases.

13. The detergent composition of claim 1, including a detergent builder or complexing agent.

14. The detergent composition of claim 1, including one or more polymers.

15. The detergent composition of claim 1, including a bleaching system.

16. The detergent composition of claim 1, which is a liquid.

17. The detergent of claim 1, wherein the stabilizing agent comprises a polyol, a sugar or sugar alcohol, lactic acid, boric acid, a boric acid derivative, or a phenyl boronic acid derivative.

18. The detergent of claim 1, wherein the stabilizing agent comprises propylene glycol or glycerol.

19. The detergent of claim 1, wherein the stabilizing agent comprises an aromatic borate ester or 4-formylphenyl boronic acid.

* * * * *

SEQUENCE LISTING

```
<160> NUMBER OF SEQ ID NOS: 45

<210> SEQ ID NO 1
<211> LENGTH: 1259
<212> TYPE: DNA
<213> ORGANISM: Aspergillus fumigatus

<400> SEQUENCE: 1
atgcttcaca agtatagcct gttctgtctc actattttct cctgcctctt cgttgtgagc     60
gtggatgggg caatactcgg tagggatgat gaaggccgac agcagatacc tgatgaactc    120
tttgaatcac tcgaagagct ctcacgtatc gttgatgttt cgtactgtgt tgggaccact    180
gaaattcgga agccattcaa gtgtctcagt cattgtagtg aattccaggg cttcgaactg    240
gtcaccgtat gttgaaagcc tctcacttat atgttgtctt tctgtccaag cttgatggct    300
tagatcgtct ccagacatgg aataccggtc ctttcctttc cgattcctgt ggctatgtaa    360
ccctctccca cgaaccatct ccgaagcgga tcatcgttgc ctttcgcggc acttactcga    420
tcgccaacac gatcatcgat ctatccgcct atcctcaggc ctatgtaccg tatcatcccg    480
aggatggaaa agtgtccgac catttacaat gtctgaactg cacagttcat gcggggtttt    540
tggcctcgtg gagcaatgct cgcgccatag tactcgagca cgtagctgtg gcaagggccc    600
ggtacccgga ttacagcttg gttttgaccg gccactcgct tggcggcgcc gtcgccgctc    660
ttgccggggt cgaaatgcaa ctgcgcgggt gggagccaca agtgaccact ttcggagagc    720
caagaatcgg aaacaaggct tttgtggaat ttcttgatcg gatctttgat ctagatggct    780
tgggagctga tgcccaggac accagatttc gaagagtcac acatatcaac gatccggtcc    840
ccctactccc attgtcagaa tggggttatg agatgcatgc gggagagatc tttatcgcta    900
aggaggagct ctcgcctcta ccccatgata tcagactgtg ccagggcgac aacgatgcgc    960
gatgcattgc aggaacggat ggagctgtaa cgcgcatgct gaacgagttg gatgataccg   1020
ttttgcccaa gcagcctcta gcgaaacgag tccagtcacc ccatcaggcc gttttggcag   1080
acgtggatcc tcatagtagt gcagatgtcg acgagcaagt acagacgcca ttcagcctgc   1140
cttggcatct tattccctcc agataccgac tgtgggagct gttcttcgct catcgtgatt   1200
atttctggcg gcttgggctt tgtgtaccag gcggtgatcc gactggcaag ataatctga    1259

<210> SEQ ID NO 2
<211> LENGTH: 396
<212> TYPE: PRT
<213> ORGANISM: Aspergillus fumigatus

<400> SEQUENCE: 2

Met Leu His Lys Tyr Ser Leu Phe Cys Leu Thr Ile Phe Ser Cys Leu
1               5                   10                  15

Phe Val Val Ser Val Asp Gly Ala Ile Leu Gly Arg Asp Asp Glu Gly
            20                  25                  30

Arg Gln Gln Ile Pro Asp Glu Leu Phe Glu Ser Leu Glu Glu Leu Ser
        35                  40                  45

Arg Ile Val Asp Val Ser Tyr Cys Val Gly Thr Thr Glu Ile Arg Lys
    50                  55                  60
```

```
Pro Phe Lys Cys Leu Ser His Cys Ser Glu Phe Gln Gly Phe Glu Leu
 65                  70                  75                  80
Val Thr Thr Trp Asn Thr Gly Pro Phe Leu Ser Asp Ser Cys Gly Tyr
                 85                  90                  95
Val Thr Leu Ser His Glu Pro Ser Pro Lys Arg Ile Ile Val Ala Phe
            100                 105                 110
Arg Gly Thr Tyr Ser Ile Ala Asn Thr Ile Ile Asp Leu Ser Ala Tyr
        115                 120                 125
Pro Gln Ala Tyr Val Pro Tyr His Pro Glu Asp Gly Lys Val Ser Asp
    130                 135                 140
His Leu Gln Cys Leu Asn Cys Thr Val His Ala Gly Phe Leu Ala Ser
145                 150                 155                 160
Trp Ser Asn Ala Arg Ala Ile Val Leu Glu His Val Ala Val Ala Arg
                165                 170                 175
Ala Arg Tyr Pro Asp Tyr Ser Leu Val Leu Thr Gly His Ser Leu Gly
            180                 185                 190
Gly Ala Val Ala Ala Leu Ala Gly Val Glu Met Gln Leu Arg Gly Trp
        195                 200                 205
Glu Pro Gln Val Thr Thr Phe Gly Glu Pro Arg Ile Gly Asn Lys Ala
    210                 215                 220
Phe Val Glu Phe Leu Asp Arg Ile Phe Asp Leu Asp Gly Leu Gly Ala
225                 230                 235                 240
Asp Ala Gln Asp Thr Arg Phe Arg Arg Val Thr His Ile Asn Asp Pro
                245                 250                 255
Val Pro Leu Leu Pro Leu Ser Glu Trp Gly Tyr Glu Met His Ala Gly
            260                 265                 270
Glu Ile Phe Ile Ala Lys Glu Glu Leu Ser Pro Leu Pro His Asp Ile
        275                 280                 285
Arg Leu Cys Gln Gly Asp Asn Asp Ala Arg Cys Ile Ala Gly Thr Asp
    290                 295                 300
Gly Ala Val Thr Arg Met Leu Asn Glu Leu Asp Asp Thr Val Leu Pro
305                 310                 315                 320
Lys Gln Pro Leu Ala Lys Arg Val Gln Ser Pro His Gln Ala Val Leu
                325                 330                 335
Ala Asp Val Asp Pro His Ser Ser Ala Asp Val Asp Glu Gln Val Gln
            340                 345                 350
Thr Pro Phe Ser Leu Pro Trp His Leu Ile Pro Ser Arg Tyr Arg Leu
        355                 360                 365
Trp Glu Leu Phe Phe Ala His Arg Asp Tyr Phe Trp Arg Leu Gly Leu
    370                 375                 380
Cys Val Pro Gly Gly Asp Pro Thr Gly Lys Ile Ile
385                 390                 395

<210> SEQ ID NO 3
<211> LENGTH: 947
<212> TYPE: DNA
<213> ORGANISM: Aspergillus fumigatus

<400> SEQUENCE: 3
atgtttcacc cagatatttc ggctgggctt ctagccaatc taacactatt ttctgaatat     60
gccgctgcct cgacgtgtgc agcaaacttc aactcacata cattatcgaa ggtagtgtgt    120
gatccaggtg tatgcccaac cctggagcag acagacacaa atgtcatggt tgggttcatg    180
gggtatgatt ccatcaacag gcatgaact gaaaagctaa cgccaagtat acatcatccg    240
```

```
ggtaacgtca ctggcttcgt ggcaattgac aacacaaatc aattgatcgt tctgtcattc    300
cgcggtagcc ggaccctagg caactatatc actgattcca aataccagca ggtgcctgct    360
atttgcccag gttgccaagt gcataaaggc tattactggg cctggggaaa cttttcagca    420
tttataatgc aacctataaa ccagcttgct gctatatatc caagctatca gattgtcttc    480
actggccaca gttttggagg tgcactagct acgcttgggg cagcacttga gggaggaaat    540
cctagcagac ctattgatct ggtaagtacc tcagtcaccg caaatgtttc cctagagaat    600
gcattaatca gatacagtac acttttggat gtccccaact gggcaatcat gattttgctg    660
agtttgtcac tgctgtaacg gcaggctctg gtacagagt cacacattcg gatgatccag     720
ttccaagggt cttttctact cagccttgga tcaacaagac ttggcagtat agcacaactt    780
ctcctgagtt ttggattacc acaggaaatg gcgtgccagt cacagccagt gatatacaag    840
tcatcgaggg cattgacaac aagagtggga accttggcac cactggttct gatacttcag    900
ctcatatttg gtatattggc aacatgagcg ggtgctcaac taactga                 947
```

<210> SEQ ID NO 4
<211> LENGTH: 283
<212> TYPE: PRT
<213> ORGANISM: Aspergillus fumigatus

<400> SEQUENCE: 4

```
Met Phe His Pro Asp Ile Ser Ala Gly Leu Leu Ala Asn Leu Thr Leu
1               5                   10                  15

Phe Ser Glu Tyr Ala Ala Ala Ser Thr Cys Ala Ala Asn Phe Asn Ser
            20                  25                  30

His Thr Leu Ser Lys Val Val Cys Asp Pro Gly Val Cys Pro Thr Leu
        35                  40                  45

Glu Gln Thr Asp Thr Asn Val Met Val Gly Phe Met Gly Ile His His
    50                  55                  60

Pro Gly Asn Val Thr Gly Phe Val Ala Ile Asp Asn Thr Asn Gln Leu
65                  70                  75                  80

Ile Val Leu Ser Phe Arg Gly Ser Arg Thr Leu Gly Asn Tyr Ile Thr
                85                  90                  95

Asp Ser Lys Tyr Gln Gln Val Pro Ala Ile Cys Pro Gly Cys Gln Val
            100                 105                 110

His Lys Gly Tyr Tyr Trp Ala Trp Gly Asn Phe Ser Ala Phe Ile Met
        115                 120                 125

Gln Pro Ile Asn Gln Leu Ala Ala Ile Tyr Pro Ser Tyr Gln Ile Val
    130                 135                 140

Phe Thr Gly His Ser Phe Gly Gly Ala Leu Ala Thr Leu Gly Ala Ala
145                 150                 155                 160

Leu Glu Gly Gly Asn Pro Ser Arg Pro Ile Asp Leu Ile Gln Tyr Thr
                165                 170                 175

Phe Gly Cys Pro Gln Leu Gly Asn His Asp Phe Ala Glu Phe Val Thr
            180                 185                 190

Ala Val Thr Ala Gly Ser Gly Tyr Arg Val Thr His Ser Asp Asp Pro
        195                 200                 205

Val Pro Arg Val Phe Ser Thr Gln Pro Trp Ile Asn Lys Thr Trp Gln
    210                 215                 220

Tyr Ser Thr Thr Ser Pro Glu Phe Trp Ile Thr Gly Asn Gly Val
225                 230                 235                 240

Pro Val Thr Ala Ser Asp Ile Gln Val Ile Glu Gly Ile Asp Asn Lys
                245                 250                 255
```

Ser Gly Asn Leu Gly Thr Thr Gly Ser Asp Thr Ser Ala His Ile Trp
          260                 265                 270

Tyr Ile Gly Asn Met Ser Gly Cys Ser Thr Asn
          275                 280

<210> SEQ ID NO 5
<211> LENGTH: 1088
<212> TYPE: DNA
<213> ORGANISM: Magnaporthe grisea

<400> SEQUENCE: 5

```
atgaaggtct cgttcgtgtc atcgctcctc gcgctcccgc tccttgcggc cgcggccccc    60
aagcccgagg ccgctgagct gtcgagccgc gacgtgaccg tgacgcagca ggagctcaac   120
ggcttcatgt acatgcggca gctcgccctc gccgcctact gcaactccaa ggacagcctg   180
gtcggccaaa aggtcacatg cagcaacaac gcctgcccgg acattggcgc cgctaacgtg   240
gtcaactttg cccatctcga gtatgttttt ttccctcttt tttcttgtga aactcttgtt   300
gtataaaaaa aaaggtcaaa tcatctaaca gataccccc acgatgggc caacagcacc   360
gacatcggca tcaaggccga cggcgctgtc ttcatcgacc acaccagggg cggcatcgtc   420
atgtccttca tgggctccaa gtcgtggcag tccttcatga ccgagtaagc aaaacaccccc  480
acttactcta gatttttttt tatcttgtca tccacatgac tcacatttca cctccaaaca   540
gcctcgactt caccggcagc gactcctccg agatctgcag cggctgcacg gtccactacg   600
gcatcaagct cacctacgac atcatcgagg gcgcgctgat caacgccctc aactcggccc   660
gcgcccagtg gccgtcgtac caggtcgtcg gacgggcca ctccatcgga gccggcgtcg   720
ccaccgtcgc cgccgcccgc ctgcgcaacc gcctcaacgt cgacatccag ctctacacct   780
ttggcagccc ccgcgtcggc aacgacgcct ttgccacctt tgtcaccaac cagaaccgcg   840
ccgcaacta ccgcatcacc cactacgacg acgtcgtcgc cgccttgccc ccgtcctggg   900
ccggcttcgc ccacgtcagc cccgagtact ggctgcgcag gaaggacgcc agcgacttca   960
actacccgct cagcgaggtc gtcgtctgcg agggcatcaa ccccaagggt tgcaggaaca  1020
gcatgggcac caccctcagc ggcaaggccc acggagagta ctttggcgcc attagcgctt  1080
gctactga                                                          1088
```

<210> SEQ ID NO 6
<211> LENGTH: 318
<212> TYPE: PRT
<213> ORGANISM: Magnaporthe grisea

<400> SEQUENCE: 6

Met Lys Val Ser Phe Val Ser Ser Leu Leu Ala Leu Pro Leu Leu Ala
1               5                   10                  15

Ala Ala Ala Pro Lys Pro Glu Ala Ala Glu Leu Ser Ser Arg Asp Val
20 25 30

Thr Val Thr Gln Gln Glu Leu Asn Gly Phe Met Tyr Met Arg Gln Leu
35 40 45

Ala Ser Ala Ala Tyr Cys Asn Ser Lys Asp Ser Leu Val Gly Gln Lys
50 55 60

Val Thr Cys Ser Asn Asn Ala Cys Pro Asp Ile Gly Ala Ala Asn Val
65 70 75 80

Val Asn Phe Ala His Leu Glu Ser Asn His Leu Thr Asp Thr Pro His
85 90 95

-continued

```
Asp Gly Ala Asn Ser Thr Asp Ile Gly Ile Lys Ala Asp Gly Ala Val
            100                 105                 110

Phe Ile Asp His Thr Arg Gly Gly Ile Val Met Ser Phe Met Gly Ser
        115                 120                 125

Lys Ser Trp Gln Ser Phe Met Thr Glu Leu Asp Phe Thr Gly Ser Asp
    130                 135                 140

Ser Ser Glu Ile Cys Ser Gly Cys Thr Val His Tyr Gly Ile Lys Leu
145                 150                 155                 160

Thr Tyr Asp Ile Ile Glu Gly Ala Leu Ile Asn Ala Leu Asn Ser Ala
                165                 170                 175

Arg Ala Gln Trp Pro Ser Tyr Gln Val Val Ala Thr Gly His Ser Ile
            180                 185                 190

Gly Ala Gly Val Ala Thr Val Ala Ala Ala Arg Leu Arg Asn Arg Leu
        195                 200                 205

Asn Val Asp Ile Gln Leu Tyr Thr Phe Gly Ser Pro Arg Val Gly Asn
    210                 215                 220

Asp Ala Phe Ala Thr Phe Val Thr Asn Gln Asn Arg Gly Arg Asn Tyr
225                 230                 235                 240

Arg Ile Thr His Tyr Asp Asp Val Val Ala Ala Leu Pro Pro Ser Trp
                245                 250                 255

Ala Gly Phe Ala His Val Ser Pro Glu Tyr Trp Leu Arg Arg Lys Asp
            260                 265                 270

Ala Ser Asp Phe Asn Tyr Pro Leu Ser Glu Val Val Val Cys Glu Gly
        275                 280                 285

Ile Asn Pro Lys Gly Cys Arg Asn Ser Met Gly Thr Thr Leu Ser Gly
    290                 295                 300

Lys Ala His Gly Glu Tyr Phe Gly Ala Ile Ser Ala Cys Tyr
305                 310                 315
```

<210> SEQ ID NO 7
<211> LENGTH: 1047
<212> TYPE: DNA
<213> ORGANISM: Magnaporthe grisea

<400> SEQUENCE: 7

```
atgaggttcc ccagcgtgct caccctttttg gccacagccc tcacctgctc ggcatcggtt     60
ctccctgccg gcctgaccta caccaagact gtcgagggcc gcgatgtgac cgtcagcgag    120
acagacctag acaacttccg tttctatgcg cagtacagcg cggcgaccta ctgcaacgat    180
gccgccgcct caggggccgc cgtcgcctgc agcaacgacg gatgtcccgc cgtcgtggcc    240
aacggagcca agatcatccg ttcgctgaac caagacacgt ccaccaacac tgccggctac    300
cttgcactcg accccaagcg gaagaacatc gtgctcgccc tccgtggctc cacgagcctc    360
cggaactgga tcaccaacct gactttcctg tggacccgct gcgactttgt ccaggactgc    420
aagctgcaca cgggctttgc cacagcctgg tcccaggtgc aggccgatgt tctggccgcc    480
atcgccgacg ccaaggccca gaaccccgac tacaccgtcg tcgtgacggg ccactccctc    540
ggcggcgccg tcgccaccgt cgcgggagtc tacctccgcc agctgggcta ccccgtcgag    600
gtttacacgt acggcagccc gcgcatcggc aatcaggagt ttgtgcagtg ggtttccacg    660
caggccggca acgtcgagta ccgcgtcacg cacatcgacg accccgtccc ccgcctgccg    720
cccatcttcc tcggctacag gcacgtcacc cccgagtact ggctcaactc tggcacctcc    780
aacacggtca actacaccgt cgccgacatc aaggtctgcg agggcttcgc caacatcaac    840
tgcaacggcg gcagcctcgg cctcgacaca aacgcccacc tctactacct caccgacatg    900
```

```
atcgcctgcg gctccaacaa gttcgtcttc cgccgcgacg acgccaacgc catcagtgac    960
gccgagctcg agcagaggct gaccatgtac gctcaaatgg atcgcgagtt tgttgctgcg   1020
cttgaagcca acaagaccgt ggcttaa                                       1047
```

<210> SEQ ID NO 8
<211> LENGTH: 348
<212> TYPE: PRT
<213> ORGANISM: Magnaporthe grisea

<400> SEQUENCE: 8

```
Met Arg Phe Pro Ser Val Leu Thr Leu Leu Ala Thr Ala Leu Thr Cys
1               5                   10                  15

Ser Ala Ser Val Leu Pro Ala Gly Leu Thr Tyr Thr Lys Thr Val Glu
            20                  25                  30

Gly Arg Asp Val Thr Val Ser Glu Thr Asp Leu Asp Asn Phe Arg Phe
        35                  40                  45

Tyr Ala Gln Tyr Ser Ala Ala Thr Tyr Cys Asn Asp Ala Ala Ala Ser
    50                  55                  60

Gly Ala Ala Val Ala Cys Ser Asn Asp Gly Cys Pro Ala Val Val Ala
65                  70                  75                  80

Asn Gly Ala Lys Ile Ile Arg Ser Leu Asn Gln Asp Thr Ser Thr Asn
                85                  90                  95

Thr Ala Gly Tyr Leu Ala Leu Asp Pro Lys Arg Lys Asn Ile Val Leu
            100                 105                 110

Ala Leu Arg Gly Ser Thr Ser Leu Arg Asn Trp Ile Thr Asn Leu Thr
        115                 120                 125

Phe Leu Trp Thr Arg Cys Asp Phe Val Gln Asp Cys Lys Leu His Thr
    130                 135                 140

Gly Phe Ala Thr Ala Trp Ser Gln Val Gln Ala Asp Val Leu Ala Ala
145                 150                 155                 160

Ile Ala Asp Ala Lys Ala Gln Asn Pro Asp Tyr Thr Val Val Val Thr
                165                 170                 175

Gly His Ser Leu Gly Gly Ala Val Ala Thr Val Ala Gly Val Tyr Leu
            180                 185                 190

Arg Gln Leu Gly Tyr Pro Val Glu Val Tyr Thr Tyr Gly Ser Pro Arg
        195                 200                 205

Ile Gly Asn Gln Glu Phe Val Gln Trp Val Ser Thr Gln Ala Gly Asn
    210                 215                 220

Val Glu Tyr Arg Val Thr His Ile Asp Asp Pro Val Pro Arg Leu Pro
225                 230                 235                 240

Pro Ile Phe Leu Gly Tyr Arg His Val Thr Pro Glu Tyr Trp Leu Asn
                245                 250                 255

Ser Gly Thr Ser Asn Thr Val Asn Tyr Thr Val Ala Asp Ile Lys Val
            260                 265                 270

Cys Glu Gly Phe Ala Asn Ile Asn Cys Asn Gly Gly Ser Leu Gly Leu
        275                 280                 285

Asp Thr Asn Ala His Leu Tyr Tyr Leu Thr Asp Met Ile Ala Cys Gly
    290                 295                 300

Ser Asn Lys Phe Val Phe Arg Arg Asp Asp Ala Asn Ala Ile Ser Asp
305                 310                 315                 320

Ala Glu Leu Glu Gln Arg Leu Thr Met Tyr Ala Gln Met Asp Arg Glu
                325                 330                 335

Phe Val Ala Ala Leu Glu Ala Asn Lys Thr Val Ala
            340                 345
```

<210> SEQ ID NO 9
<211> LENGTH: 1182
<212> TYPE: DNA
<213> ORGANISM: Magnaporthe grisea

<400> SEQUENCE: 9

```
atgttgtggc gtcgggcggg tggcctctgt ctgttgctgt gttgggcctg ggcaacaccg      60
gcacaagctg cagcatttag tcatgacatc acccagctga gctacacgga tgtcgactcg     120
cctctccaaa aacacctaca atcacaacaa caacaaaaac aagaacacaa acaaaaacct     180
atcaccacca caaccatttc ttcaatactc ttcacgtctc tagagcgcct ggcccgcctc     240
gtagacatag cctactgcgt gggaagtctg cccggcatct cgcggccctt cacctgcgcc     300
tcgcgctgcg ccgatttccc ccacgtttca ctcgtcaaca cctgggacac gggcccactc     360
ctgacagaca gctgcggcta cgtcgccatc gaccacgccg atgaagccat agtggtcgcc     420
tttcggggca cctacagcat cgccaacacc gtgattgacc tcagcacggt gccgcaggag     480
tacgtgccct atccggagcc cgacgacgat ggcgacaggg agcgctgcga caactgcacc     540
gtgcacctag gattcctagc cagctggaag gtcgccagga atctggtcct gcccgccatc     600
gaggaggcga ggcagaagca ccccggcttc agcatcaacc tcgtcggcca cagcctcggc     660
ggtgccgtcg ctgcgctggc ggcgctcgag ctgaagctca tcagcggcta cgatgtcgta     720
gtcacgactt ttggtgagcc gagggttggc aacagcgggc tggcaaagtt cattgatcgc     780
gtgttcggct tagaccagga agcaaaagag gacatggcgt accgcagggt cacgcacgcc     840
gaggatccgg taccgttgct gccgctcgag gagtggggat acaggtcaca cgccggcgag     900
attcacattg agaagccggc gctaccacca gcaccgactg acataaagtt gtgcaaaggc     960
gaaagggatc ccgattgcag caacgggaac tctgacgcgg cgctgactac cttgctgctt    1020
ggagaggaac attatctaaa gaaacagcat ctgaagctgt ggcagctgtt ctttgcccat    1080
cgagactact tttggaggct tgggctttgc gttcccggtg gtgatccggc tgattggggt    1140
agagacaagt atgatgtggc tcctggccag gatgagctct aa                       1182
```

<210> SEQ ID NO 10
<211> LENGTH: 393
<212> TYPE: PRT
<213> ORGANISM: Magnaporthe grisea

<400> SEQUENCE: 10

```
Met Leu Trp Arg Arg Ala Gly Gly Leu Cys Leu Leu Leu Cys Trp Ala
1               5                   10                  15

Trp Ala Thr Pro Ala Gln Ala Ala Ala Phe Ser His Asp Ile Thr Gln
            20                  25                  30

Leu Ser Tyr Thr Asp Val Asp Ser Pro Leu Gln Lys His Leu Gln Ser
        35                  40                  45

Gln Gln Gln Gln Lys Gln Glu His Lys Gln Lys Pro Ile Thr Thr Thr
    50                  55                  60

Thr Ile Ser Ser Ile Leu Phe Thr Ser Leu Glu Arg Leu Ala Arg Leu
65                  70                  75                  80

Val Asp Ile Ala Tyr Cys Val Gly Ser Leu Pro Gly Ile Ser Arg Pro
                85                  90                  95

Phe Thr Cys Ala Ser Arg Cys Ala Asp Phe Pro His Val Ser Leu Val
            100                 105                 110

Asn Thr Trp Asp Thr Gly Pro Leu Leu Thr Asp Ser Cys Gly Tyr Val
        115                 120                 125
```

```
Ala Ile Asp His Ala Asp Glu Ala Ile Val Val Ala Phe Arg Gly Thr
130                 135                 140
Tyr Ser Ile Ala Asn Thr Val Ile Asp Leu Ser Thr Val Pro Gln Glu
145                 150                 155                 160
Tyr Val Pro Tyr Pro Glu Pro Asp Asp Gly Asp Arg Glu Arg Cys
            165                 170                 175
Asp Asn Cys Thr Val His Leu Gly Phe Leu Ala Ser Trp Lys Val Ala
            180                 185                 190
Arg Asn Leu Val Leu Pro Ala Ile Glu Glu Ala Arg Gln Lys His Pro
            195                 200                 205
Gly Phe Ser Ile Asn Leu Val Gly His Ser Leu Gly Gly Ala Val Ala
210                 215                 220
Ala Leu Ala Ala Leu Glu Leu Lys Leu Ile Ser Gly Tyr Asp Val Val
225                 230                 235                 240
Val Thr Thr Phe Gly Glu Pro Arg Val Gly Asn Ser Gly Leu Ala Lys
                245                 250                 255
Phe Ile Asp Arg Val Phe Gly Leu Asp Gln Glu Ala Lys Glu Asp Met
                260                 265                 270
Ala Tyr Arg Arg Val Thr His Ala Glu Asp Pro Val Pro Leu Leu Pro
            275                 280                 285
Leu Glu Glu Trp Gly Tyr Arg Ser His Ala Gly Glu Ile His Ile Glu
290                 295                 300
Lys Pro Ala Leu Pro Pro Ala Pro Thr Asp Ile Lys Leu Cys Lys Gly
305                 310                 315                 320
Glu Arg Asp Pro Asp Cys Ser Asn Gly Asn Ser Asp Ala Ala Leu Thr
                325                 330                 335
Thr Leu Leu Leu Gly Glu Glu His Tyr Leu Lys Lys Gln His Leu Lys
            340                 345                 350
Leu Trp Gln Leu Phe Phe Ala His Arg Asp Tyr Phe Trp Arg Leu Gly
            355                 360                 365
Leu Cys Val Pro Gly Gly Asp Pro Ala Asp Trp Gly Arg Asp Lys Tyr
370                 375                 380
Asp Val Ala Pro Gly Gln Asp Glu Leu
385                 390

<210> SEQ ID NO 11
<211> LENGTH: 1041
<212> TYPE: DNA
<213> ORGANISM: Aspergillus nidulans

<400> SEQUENCE: 11
atgatccgtt tggggtattc tgccatcttc gtagcccttg ctgggttagc cgttgccgct      60
ccagcgccgc tgaatcgtcg tggtatgtca ccttgcatgg ggatatggta caggactaac     120
gttgtgtaga cgtttcgacg gaggccctaa atcaactgac cctgttcgcg gagtattctg     180
cggcatcgta ctgcacaccc aatattgggt cagtcgggga caagctgact tgcgcatctg     240
gaaactgccc gacagttgag gcagcagaca cgacaacgct ggctgaattc tatcagtgcg     300
ttaagccctg cattcggggt tccaaacaga tccaactagt ctgacgagtc acagggagaa     360
cgaatacggg gatgtagcag gcttccttgc cgcagataca accaacgagt tactcgtctt     420
gtccttccgt gggagccgga cgattgacac gtggattgca aacctcgact ttggcctgga     480
gtcggtcgag gagatctgta gcggatgcaa agcccacggc gggttctgga aggcatggca     540
ggttgttgca gactcgttga cctcagcaat tgagtctgct actgccacat atcccggcta     600
```

```
cgccattgtc ttcacaggcc acagctttgg aggagcattg gctactctag gcgcagcgca    660
gctgcgaaaa gcaggttatg ccatcgaact tgtaagaatc cagtgtccag ctggtggcta    720
gctgtctgct gacgagcgta gtaccctat ggtagcccgc gtgttggcaa cgaagctttg     780
gcgcaataca tcacagacca gggggcaaac tatcgagtga cgcacactaa cgatatcgtt    840
cccagacttc ctcccatgtt gttgggcttc agccacttga gccctgagta ttggattacc    900
agcgacaatg aggttacccc gacgacgaca gatatccagg tgattgaagg cgttgggtcg    960
agggacggaa atgcgggtga ggctgcccag tcagtggagg cacacagttg gtatctgata   1020
gatatcactg cctgccagta a                                             1041
```

```
<210> SEQ ID NO 12
<211> LENGTH: 294
<212> TYPE: PRT
<213> ORGANISM: Aspergillus nidulans

<400> SEQUENCE: 12
```

Met Ile Arg Leu Gly Tyr Ser Ala Ile Phe Val Ala Leu Ala Gly Leu
1               5                   10                  15

Ala Val Ala Ala Pro Ala Pro Leu Asn Arg Arg Asp Val Ser Thr Glu
            20                  25                  30

Ala Leu Asn Gln Leu Thr Leu Phe Ala Glu Tyr Ser Ala Ala Ser Tyr
        35                  40                  45

Cys Thr Pro Asn Ile Gly Ser Val Gly Asp Lys Leu Thr Cys Ala Ser
    50                  55                  60

Gly Asn Cys Pro Thr Val Glu Ala Ala Asp Thr Thr Leu Ala Glu
65                  70                  75                  80

Phe Tyr Gln Glu Asn Glu Tyr Gly Asp Val Ala Gly Phe Leu Ala Ala
                85                  90                  95

Asp Thr Thr Asn Glu Leu Leu Val Leu Ser Phe Arg Gly Ser Arg Thr
            100                 105                 110

Ile Asp Thr Trp Ile Ala Asn Leu Asp Phe Gly Leu Glu Ser Val Glu
        115                 120                 125

Glu Ile Cys Ser Gly Cys Lys Ala His Gly Gly Phe Trp Lys Ala Trp
    130                 135                 140

Gln Val Val Ala Asp Ser Leu Thr Ser Ala Ile Glu Ser Ala Thr Ala
145                 150                 155                 160

Thr Tyr Pro Gly Tyr Ala Ile Val Phe Thr Gly His Ser Phe Gly Gly
                165                 170                 175

Ala Leu Ala Thr Leu Gly Ala Ala Gln Leu Arg Lys Ala Gly Tyr Ala
            180                 185                 190

Ile Glu Leu Tyr Pro Tyr Gly Ser Pro Arg Val Gly Asn Glu Ala Leu
        195                 200                 205

Ala Gln Tyr Ile Thr Asp Gln Gly Ala Asn Tyr Arg Val Thr His Thr
    210                 215                 220

Asn Asp Ile Val Pro Arg Leu Pro Pro Met Leu Leu Gly Phe Ser His
225                 230                 235                 240

Leu Ser Pro Glu Tyr Trp Ile Thr Ser Asp Asn Glu Val Thr Pro Thr
                245                 250                 255

Thr Thr Asp Ile Gln Val Ile Glu Gly Val Gly Ser Arg Asp Gly Asn
            260                 265                 270

Ala Gly Glu Ala Ala Gln Ser Val Glu Ala His Ser Trp Tyr Leu Ile
            275                 280                 285
Asp Ile Thr Ala Cys Gln
        290

<210> SEQ ID NO 13
<211> LENGTH: 1119
<212> TYPE: DNA
<213> ORGANISM: Aspergillus nidulans

<400> SEQUENCE: 13

```
atgtatttcc ttctctccgt catcttccac tttcctgtct tctgtgccgg ctttccacct     60
gccgtatcca gaggtacgtg attcaatgtg ctcagtaatc cggcttgaac caaccgcaat    120
agaaatatcc acaactctcc tcaccaaact cacccctcatg tctcaatact ctgctgcttc   180
aggttgcagc gaaaacaata actcttctgt agggagttct gtttattgcg gggctgaaat   240
gtgtccgctt atcgacagtg ccaatacaga actcctttat gcattctcag agtattcccc   300
tttcgatatc tcattggatt accatactca atagacgcta actctttact ttctcattac   360
acaggattta ccccggcgat acggctggct acattgccgc cgaccacaca aacgcccttc   420
tgatcatctc gtttcgcaat agcgtgaccc ccacaaactt catcaccgat gggcattcc    480
ttcaagtcag cgcgcctacc gcgtgctccg gatgccgagc acataaaggg ttctggtcgg   540
cggccgtggc cgccgacaag gctttagatg gttccatcag ggaggcaaag gccagatacc   600
cagagtacga actgacgttg actgggcata gtttgggagg tgcacttgca acgcttcatg   660
caattttcct gaggaataga ggagttgctg ttgattctgt aagttgaggc tttgccgcaa   720
tgacgacccg agcaacttga tggctgctga tgctgactgg actgctagta taccttcggc   780
gcgccatcgg ttggtgacta cgcaatggcc gattacatca cgaacgggcc cggtagcgac   840
aatgggagga actatcgcgt tacgcacctg aatgacgtct ttccaaaaat gctctaccgt   900
gcgtctagga tgccggttgc agatcggctg gtacaagagt acagccagtc cgggccagag   960
tactggatta cgtctggctt cggcgagcct gttacaactg cggatgtgca catccttgag  1020
ggcgtggata atgagcaggg caatctggga agagaacctg gcagtctgag ggaccatatg  1080
tggtatttgg gggcgacaga tgcttgccca ctaggctga                          1119
```

<210> SEQ ID NO 14
<211> LENGTH: 308
<212> TYPE: PRT
<213> ORGANISM: Aspergillus nidulans

<400> SEQUENCE: 14

Met Tyr Phe Leu Leu Ser Val Ile Phe His Phe Pro Val Phe Cys Ala
1               5                   10                  15

Gly Phe Pro Pro Ala Val Ser Arg Glu Ile Ser Thr Thr Leu Leu Thr
            20                  25                  30

Lys Leu Thr Leu Met Ser Gln Tyr Ser Ala Ala Ser Gly Cys Ser Glu
        35                  40                  45

Asn Asn Asn Ser Ser Val Gly Ser Val Tyr Cys Gly Ala Glu Met
    50                  55                  60

Cys Pro Leu Ile Asp Ser Ala Asn Thr Glu Leu Leu Tyr Ala Phe Ser
65                  70                  75                  80

Glu Ile Tyr Pro Gly Asp Thr Ala Gly Tyr Ile Ala Ala Asp His Thr
                85                  90                  95

```
Asn Ala Leu Leu Ile Ile Ser Phe Arg Asn Ser Val Thr Pro Thr Asn
                100                 105                 110

Phe Ile Thr Asp Trp Ala Phe Leu Gln Val Ser Ala Pro Thr Ala Cys
            115                 120                 125

Ser Gly Cys Arg Ala His Lys Gly Phe Trp Ser Ala Ala Val Ala Ala
        130                 135                 140

Asp Lys Ala Leu Asp Gly Ser Ile Arg Glu Ala Lys Ala Arg Tyr Pro
145                 150                 155                 160

Glu Tyr Glu Leu Thr Leu Thr Gly His Ser Leu Gly Gly Ala Leu Ala
                165                 170                 175

Thr Leu His Ala Ile Phe Leu Arg Asn Arg Gly Val Ala Val Asp Ser
            180                 185                 190

Tyr Thr Phe Gly Ala Pro Ser Val Gly Asp Tyr Ala Met Ala Asp Tyr
        195                 200                 205

Ile Thr Asn Gly Pro Gly Ser Asp Asn Gly Arg Asn Tyr Arg Val Thr
210                 215                 220

His Leu Asn Asp Val Phe Pro Lys Met Leu Tyr Arg Ala Ser Arg Met
225                 230                 235                 240

Pro Val Ala Asp Arg Leu Val Gln Glu Tyr Ser Gln Ser Gly Pro Glu
                245                 250                 255

Tyr Trp Ile Thr Ser Gly Phe Gly Glu Pro Val Thr Thr Ala Asp Val
            260                 265                 270

His Ile Leu Glu Gly Val Asp Asn Glu Gln Gly Asn Leu Gly Arg Glu
        275                 280                 285

Pro Gly Ser Leu Arg Asp His Met Trp Tyr Leu Gly Ala Thr Asp Ala
290                 295                 300

Cys Pro Leu Gly
305

<210> SEQ ID NO 15
<211> LENGTH: 1283
<212> TYPE: DNA
<213> ORGANISM: Aspergillus nidulans

<400> SEQUENCE: 15
atgacggtgt ctcttgacag tttattcctt acacttatta tattcctcac gaggctatgc      60
agcgtctcga ccgctcacgt ggtaccccct gaggccagca aggatcccga aaatatcacg     120
ccagggaggc aaatctccca ggaactattt gactctattg aggagctggc tcatattgtc     180
gatatcgcct actgcattgg gactactggc attagaaagc cgttccaatg cctcagtcac     240
tgtgatgagc taaagggtt tgaactaatc aacgtgcgct tttccacaga cgatctaccc      300
gagccgtttg agagatagta gctgactaga tagaaactca gacatggcat acaggtccct     360
ttctctctga ttcctgcggc tacatcgccc tctcgcatcc ccctcaccg aagcgaatca      420
tagtcgcttt ccgcggtaca tactcaatcc gaacgcaat agttgacctt tccatgtatc      480
cccaggaata cataccgttt tccccaggca acgatactga cggcgatgca ccgaagtgcg     540
aggactgttg ggtccattta ggcttcatga acgcatggcg tttaacccgc gcaacaatcc     600
tagacaccat ctccgcagca agagaccaat accctgatta cgctctaacc ctagtaggcc     660
actctctcgg cggcgcagtt gccgctctcg caggaacaga aatgcagctc gcggatgggg     720
aacccgtcgt gacgactttc ggggaaccaa gggtagggaa taaggcgttt gtcgactatc     780
tagacaccgt gttccgcctg aatctggca atgagcgggt gtggaaattc cgccgggtga     840
cgcatgtgaa tgaccctgta ccctaatcc cgcttacaga atggggctac gagatgcaca     900
```

```
gcggagagat ttatattgac cgcgttgagc ttccattttc tgttgacgat gtcaggtact    960
gccagggcgg gtccgatcca aactgcattt cagacgcgga ggggaagagc acaactttct   1020
ccccatatag ctcgcagggc tttgatctct ccgaatccaa catggagcag caagtccttt   1080
cgcgctcgcc gcaccagtcg aaggatcagc aacaggagaa tgagaaggga gcttttccat   1140
atctggaatc ccagagtacc tcgtgtctgc catggggtat acttccacct aggtttcgac   1200
tgtgggagct attctactct catcgtgact actttattcg tttggggctt tgcgttccca   1260
agggagattt gtcagggggg tga                                           1283
```

<210> SEQ ID NO 16
<211> LENGTH: 404
<212> TYPE: PRT
<213> ORGANISM: Aspergillus nidulans

<400> SEQUENCE: 16

```
Met Thr Val Ser Leu Asp Ser Leu Phe Leu Thr Leu Ile Ile Phe Leu
1               5                   10                  15

Thr Arg Leu Cys Ser Val Ser Thr Ala His Val Pro Leu Glu Ala
            20                  25                  30

Ser Lys Asp Pro Glu Asn Ile Thr Pro Gly Arg Gln Ile Ser Gln Glu
        35                  40                  45

Leu Phe Asp Ser Ile Glu Glu Leu Ala His Ile Val Asp Ile Ala Tyr
    50                  55                  60

Cys Ile Gly Thr Thr Gly Ile Arg Lys Pro Phe Gln Cys Leu Ser His
65                  70                  75                  80

Cys Asp Glu Leu Lys Gly Phe Glu Leu Ile Asn Thr Trp His Thr Gly
                85                  90                  95

Pro Phe Leu Ser Asp Ser Cys Gly Tyr Ile Ala Leu Ser His Pro Pro
            100                 105                 110

Ser Pro Lys Arg Ile Ile Val Ala Phe Arg Gly Thr Tyr Ser Ile Pro
        115                 120                 125

Asn Ala Ile Val Asp Leu Ser Met Tyr Pro Gln Glu Tyr Ile Pro Phe
    130                 135                 140

Ser Pro Gly Asn Asp Thr Asp Gly Asp Ala Pro Lys Cys Glu Asp Cys
145                 150                 155                 160

Trp Val His Leu Gly Phe Met Asn Ala Trp Arg Leu Thr Arg Ala Thr
                165                 170                 175

Ile Leu Asp Thr Ile Ser Ala Ala Arg Asp Gln Tyr Pro Asp Tyr Ala
            180                 185                 190

Leu Thr Leu Val Gly His Ser Leu Gly Gly Ala Val Ala Ala Leu Ala
        195                 200                 205

Gly Thr Glu Met Gln Leu Arg Gly Trp Glu Pro Val Val Thr Thr Phe
    210                 215                 220

Gly Glu Pro Arg Val Gly Asn Lys Ala Phe Val Asp Tyr Leu Asp Thr
225                 230                 235                 240

Val Phe Arg Leu Glu Ser Gly Asn Glu Arg Gly Trp Lys Phe Arg Arg
                245                 250                 255

Val Thr His Val Asn Asp Pro Val Pro Leu Ile Pro Leu Thr Glu Trp
            260                 265                 270

Gly Tyr Glu Met His Ser Gly Glu Ile Tyr Ile Asp Arg Val Glu Leu
        275                 280                 285

Pro Phe Ser Val Asp Asp Val Arg Tyr Cys Gln Gly Gly Ser Asp Pro
    290                 295                 300
```

```
Asn Cys Ile Ser Asp Ala Glu Gly Lys Ser Thr Thr Phe Ser Pro Tyr
305                 310                 315                 320

Ser Ser Gln Gly Phe Asp Leu Ser Glu Ser Asn Met Glu Gln Gln Val
            325                 330                 335

Leu Ser Arg Ser Pro His Gln Ser Lys Asp Gln Gln Gln Glu Asn Glu
        340                 345                 350

Lys Gly Ala Phe Pro Tyr Leu Glu Ser Gln Ser Thr Ser Cys Leu Pro
            355                 360                 365

Trp Gly Ile Leu Pro Pro Arg Phe Arg Leu Trp Glu Leu Phe Tyr Ser
        370                 375                 380

His Arg Asp Tyr Phe Ile Arg Leu Gly Leu Cys Val Pro Lys Gly Asp
385                 390                 395                 400

Leu Ser Gly Gly

<210> SEQ ID NO 17
<211> LENGTH: 24
<212> TYPE: DNA
<213> ORGANISM: Aspergillus fumigatus

<400> SEQUENCE: 17
gagacgcatg cttcacaagt atag                                          24

<210> SEQ ID NO 18
<211> LENGTH: 33
<212> TYPE: DNA
<213> ORGANISM: Aspergillus fumigatus

<400> SEQUENCE: 18
gtcacctcta gttaattaat cagattatct tgc                                33

<210> SEQ ID NO 19
<211> LENGTH: 22
<212> TYPE: DNA
<213> ORGANISM: Aspergillus fumigatus

<400> SEQUENCE: 19
gtgccccatg atacgcctcc gg                                            22

<210> SEQ ID NO 20
<211> LENGTH: 26
<212> TYPE: DNA
<213> ORGANISM: Aspergillus fumigatus

<400> SEQUENCE: 20
gagtcgtatt tccaaggctc ctgacc                                        26

<210> SEQ ID NO 21
<211> LENGTH: 24
<212> TYPE: DNA
<213> ORGANISM: Aspergillus fumigatus

<400> SEQUENCE: 21
ggaggccatg aagtggacca acgg                                          24

<210> SEQ ID NO 22
<211> LENGTH: 45
<212> TYPE: DNA
<213> ORGANISM: Aspergillus fumigatus

<400> SEQUENCE: 22
caccgtgaaa gccatgctct ttccttcgtg tagaagacca gacag                   45
```

```
<210> SEQ ID NO 23
<211> LENGTH: 45
<212> TYPE: DNA
<213> ORGANISM: Aspergillus fumigatus

<400> SEQUENCE: 23
ctggtcttct acacgaagga aagagcatgg ctttcacggt gtctg              45

<210> SEQ ID NO 24
<211> LENGTH: 44
<212> TYPE: DNA
<213> ORGANISM: Aspergillus fumigatus

<400> SEQUENCE: 24
ctatatacac aactggattt accatgggcc cgcggccgca gatc               44

<210> SEQ ID NO 25
<211> LENGTH: 44
<212> TYPE: DNA
<213> ORGANISM: Aspergillus fumigatus

<400> SEQUENCE: 25
gatctgcggc cgcgggccca tggtaaatcc agttgtgtat atag               44

<210> SEQ ID NO 26
<211> LENGTH: 26
<212> TYPE: DNA
<213> ORGANISM: Aspergillus fumigatus

<400> SEQUENCE: 26
gtcgacatgg tgttttgatc atttta                                   26

<210> SEQ ID NO 27
<211> LENGTH: 26
<212> TYPE: DNA
<213> ORGANISM: Aspergillus fumigatus

<400> SEQUENCE: 27
ccatggccag ttgtgtatat agagga                                   26

<210> SEQ ID NO 28
<211> LENGTH: 30
<212> TYPE: DNA
<213> ORGANISM: Aspergillus fumigatus

<400> SEQUENCE: 28
tacacaactg gccatgcttc acaagtatag                               30

<210> SEQ ID NO 29
<211> LENGTH: 33
<212> TYPE: DNA
<213> ORGANISM: Aspergillus fumigatus

<400> SEQUENCE: 29
gtcacctcta gttaattaat cagattatct tgc                           33

<210> SEQ ID NO 30
<211> LENGTH: 20
<212> TYPE: DNA
<213> ORGANISM: Aspergillus fumigatus

<400> SEQUENCE: 30
gagacacatg tttcacccag                                          20
```

```
<210> SEQ ID NO 31
<211> LENGTH: 33
<212> TYPE: DNA
<213> ORGANISM: Aspergillus fumigatus

<400> SEQUENCE: 31
gtcacctcta gttaattaat cagttagttg agc                                33

<210> SEQ ID NO 32
<211> LENGTH: 21
<212> TYPE: DNA
<213> ORGANISM: Magnaporthe grisea

<400> SEQUENCE: 32
ccttgcccac gcctttggtt c                                             21

<210> SEQ ID NO 33
<211> LENGTH: 21
<212> TYPE: DNA
<213> ORGANISM: Magnaporthe grisea

<400> SEQUENCE: 33
ctcatagcag caggcgaagc c                                             21

<210> SEQ ID NO 34
<211> LENGTH: 36
<212> TYPE: DNA
<213> ORGANISM: Magnaporthe grisea

<400> SEQUENCE: 34
acacaactgg ccatgaaggt ctcgttcgtg tcatcg                             36

<210> SEQ ID NO 35
<211> LENGTH: 35
<212> TYPE: DNA
<213> ORGANISM: Magnaporthe grisea

<400> SEQUENCE: 35
agtcacctct agttatcagt agcaagcgct aatgg                              35

<210> SEQ ID NO 36
<211> LENGTH: 33
<212> TYPE: DNA
<213> ORGANISM: Magnaporthe grisea

<400> SEQUENCE: 36
ccatggccat gatgaggttc cccagcgtgc tca                                33

<210> SEQ ID NO 37
<211> LENGTH: 29
<212> TYPE: DNA
<213> ORGANISM: Magnaporthe grisea

<400> SEQUENCE: 37
tttaattaag ccacggtctt gttggcttc                                     29

<210> SEQ ID NO 38
<211> LENGTH: 40
<212> TYPE: DNA
<213> ORGANISM: Magnaporthe grisea

<400> SEQUENCE: 38
acacaactgg ccatgttgtg gcgtcgggcg ggtggcctct                         40
```

```
<210> SEQ ID NO 39
<211> LENGTH: 47
<212> TYPE: DNA
<213> ORGANISM: Magnaporthe grisea

<400> SEQUENCE: 39
agtcacctct agttaattaa ttagagctca tcctggccag gagccac          47

<210> SEQ ID NO 40
<211> LENGTH: 36
<212> TYPE: DNA
<213> ORGANISM: Aspergillus nidulans

<400> SEQUENCE: 40
acacaactgg ccatgatccg tttggggtat tctgcc                      36

<210> SEQ ID NO 41
<211> LENGTH: 40
<212> TYPE: DNA
<213> ORGANISM: Aspergillus nidulans

<400> SEQUENCE: 41
agtcacctct agttaattaa ttactggcag gcagtgatat                  40

<210> SEQ ID NO 42
<211> LENGTH: 36
<212> TYPE: DNA
<213> ORGANISM: Aspergillus nidulans

<400> SEQUENCE: 42
acacaactgg ccatgtattt ccttctctcc gtcatc                      36

<210> SEQ ID NO 43
<211> LENGTH: 40
<212> TYPE: DNA
<213> ORGANISM: Aspergillus nidulans

<400> SEQUENCE: 43
agtcacctct agttaattaa tcagcctagt gggcaagcat                  40

<210> SEQ ID NO 44
<211> LENGTH: 40
<212> TYPE: DNA
<213> ORGANISM: Aspergillus nidulans

<400> SEQUENCE: 44
acacaactgg ccatgacggt gtctcttgac agtttattcc                  40

<210> SEQ ID NO 45
<211> LENGTH: 46
<212> TYPE: DNA
<213> ORGANISM: Aspergillus nidulans

<400> SEQUENCE: 45
agtcacctct agttaattaa tcaccccct gacaaatctc ccttgg            46
```